United States Patent [19]

Campbell et al.

[11] Patent Number: 5,840,698
[45] Date of Patent: Nov. 24, 1998

[54] INHIBITORS OF COLLAGENASE-1 AND STORMELYSIN-I METALLOPROTEASES, PHARMACEUTICAL COMPOSITIONS COMPRISING SAME AND METHODS OF THEIR USE

[75] Inventors: David A. Campbell, San Mateo; Dinesh V. Patel, Fremont; Xiao-Yi Xiao, San Diego, all of Calif.

[73] Assignee: Affymax Technologies N.V., Greenford, England

[21] Appl. No.: 549,346

[22] Filed: Oct. 27, 1995

Related U.S. Application Data

[63] Continuation-in-part of Ser. No. 482,211, Jun. 7, 1995, abandoned, which is a continuation-in-part of Ser. No. 329,420, Oct. 27, 1994, abandoned.

[51] Int. Cl.$^6$ .......................... A61K 38/00; A61K 38/06
[52] U.S. Cl. .............................. 514/18; 514/19; 530/331; 564/154
[58] Field of Search ....................... 530/331; 514/18–19; 564/154

[56] References Cited

U.S. PATENT DOCUMENTS

| | | | |
|---|---|---|---|
| 4,235,885 | 11/1980 | Sundeen et al. | 514/562 |
| 4,327,111 | 4/1982 | Sundeen et al. | 514/467 |
| 4,371,466 | 2/1983 | McGregor | 530/329 |
| 4,424,354 | 1/1984 | Sundeen et al. | 544/299 |
| 4,511,504 | 4/1985 | McCullagh et al. | 260/1 |
| 4,568,666 | 2/1986 | McCullagh et al. | 514/20 |
| 4,595,700 | 6/1986 | Donald et al. | 514/616 |
| 4,599,361 | 7/1986 | Dickens et al. | 514/575 |
| 4,681,966 | 7/1987 | Donald et al. | 297/452.1 |
| 4,720,486 | 1/1988 | Spilburg et al. | 514/18 |
| 4,743,587 | 5/1988 | Dickens et al. | 514/575 |
| 4,771,038 | 9/1988 | Wolanin et al. | 514/18 |
| 4,857,507 | 8/1989 | Rosenberg et al. | 514/18 |
| 4,891,356 | 1/1990 | Szabo | 514/2 |
| 4,918,105 | 4/1990 | Cartwright et al. | 514/575 |
| 4,935,404 | 6/1990 | Hunter et al. | 514/7 |
| 4,937,243 | 6/1990 | Markwell et al. | 514/237.8 |
| 4,996,358 | 2/1991 | Handa et al. | 562/621 |
| 5,006,651 | 4/1991 | Broadhurst et al. | 540/463 |
| 5,010,097 | 4/1991 | Markwell et al. | 514/419 |
| 5,100,874 | 3/1992 | Odake et al. | 514/18 |
| 5,387,610 | 2/1995 | Gray et al. | 514/575 |

FOREIGN PATENT DOCUMENTS

| | | |
|---|---|---|
| 0 001 989 | 5/1979 | European Pat. Off. |
| 0 185 380 | 6/1986 | European Pat. Off. |
| 0 236 872 | 9/1987 | European Pat. Off. |
| 0 273 689 | 7/1988 | European Pat. Off. |
| 0 322 184 | 6/1989 | European Pat. Off. |
| 0 345 104 | 12/1989 | European Pat. Off. |
| 0 358 305 | 3/1990 | European Pat. Off. |
| 0 401 963 | 12/1990 | European Pat. Off. |
| 0 423 943 A2 | 4/1991 | European Pat. Off. |
| 0 489 577 | 6/1992 | European Pat. Off. |
| 0 489 579 | 6/1992 | European Pat. Off. |
| 0 575 844 | 12/1993 | European Pat. Off. |
| 0 623 676 | 11/1994 | European Pat. Off. |
| 56-077296 | 11/1979 | Japan. |
| 1146896 | 12/1987 | Japan. |
| WO 87/04349 | 7/1987 | WIPO. |
| WO88/06890 | 9/1988 | WIPO. |
| WO 89/05819 | 6/1989 | WIPO. |
| WO 90/05141 | 5/1990 | WIPO. |
| WO 90/05716 | 5/1990 | WIPO. |
| WO 90/05719 | 5/1990 | WIPO. |
| WO 91/02716 | 3/1991 | WIPO. |
| WO 91/12287 | 8/1991 | WIPO. |
| WO 91/15506 | 10/1991 | WIPO. |
| WO 91/15507 | 10/1991 | WIPO. |
| WO 93/09136 | 5/1993 | WIPO. |
| WO 93/13741 | 7/1993 | WIPO. |
| WO 93/14096 | 7/1993 | WIPO. |
| WO 93/18173 | 9/1993 | WIPO. |
| WO 93/20447 | 10/1993 | WIPO. |
| WO 93/21942 | 11/1993 | WIPO. |
| WO 93/23075 | 11/1993 | WIPO. |
| WO 93/24475 | 12/1993 | WIPO. |
| WO93/24449 | 12/1993 | WIPO. |
| WO 95/07481 | 4/1994 | WIPO. |
| 95/12603 | 5/1995 | WIPO .............................. C07F 9/30 |

OTHER PUBLICATIONS

Llorens et al., 1980, Biochem. Biophys. Res. Commu., 96(4):1710–1716 Rational design of enkephalinase inhibitors: substrate specificity of enkephalinase studies from inhibitory potency of various dipeptides.
Bailie et al., Am. J. Vet. Res., 47:2604–2611 (1986).
Baricos et al., Biochem. J., 254:609–612 (1988).
Bezant et al, "Synthesis of Novel Modified Dipeptide Inhibitors of Human Collagenase: β–Mercapo Carboxylic Acid Derivatives," J. Med. Chem., 1993, vol. 36, No. 25, pp. 4030–4039.
Bird et al, "Synthesis of Novel N–Phosphonalkyl Dipeptide Inhibitors of Human Collagenase," J. Med. Chem., 1994, vol. 37, No. 1, pp. 158–169.
Blanckaert et al., Clin. Chim. Acta, 185:73–80 (1989).
Bode et al, "Structure of Astacin and Implications for Activation of Astacins and Zinc–Ligation of Colagenases," Letters to Nature, 1992, vol. 358, pp. 164–167.
Borenfreund et al., J. Natl. Cancer Inst., 32:667–679 (1964).
Brenner et al., Genes & Develop., 3:848–859 (1989).
Brown et al., Arch. Ophthalmol., 81:370–373 (1969).

(List continued on next page.)

Primary Examiner—Ponnathapura Achutamurthy
Assistant Examiner—P. Ponnaluri
Attorney, Agent, or Firm—Gerald F. Swiss; Lauren L. Stevens

[57] ABSTRACT

Disclosed are novel inhibitors of collagenase-1 and stromelysin-I metalloproteases. The disclosed inhibitors are mercaptoketone and mercaptoalcohol compounds which are useful in pharmaceutical compositions and methods for treating or controlling disease states or conditions which involve tissue breakdown, for example, arthropathy, dermatological conditions, bone resorption, inflammatory diseases, and tumor invasion and in the promotion of wound healing.

14 Claims, 13 Drawing Sheets

OTHER PUBLICATIONS

Brown et al, "Matrix Metalloproteinase Inhibitors Containing a (Carboxyalkyl)amino Zinc Ligand: Modification of the P1 and P2' Residues," *J. Med. Chem.,* 1994, vol. 37, No. 5, pp. 674–688.

Burns et al., *Invest. Ophthalmol.,* 30:1569–1575 (1989).

Caputo et al., *J. Orthopedic Res.,* 6:103–108 (1988).

Case et al., *J. Clin Invest.,* 84:1731–1740 (1989).

Chapman et al, "Inhibition of Matrix Metalloproteinases by N–Carboxyalkyl Peptides," *J. Med. Chem.,* 1993, vol. 36, pp. 4293–4301.

Clark et al, "A Novel Inhibitor of Mammalian Collagenase," *Life Sciences,* 1985, vol. 37, pp. 575–578.

Darlak et al, "Thiol–based Inhibitors of Mammalian Collagenase," *J. of Biol. Chem.,* 1990, vol. 265, No. 9, pp. 5199–5205.

Delaisse et al., *Biochem. Biophys. Res. Commun.,* 133:483–90 (1985).

Docherty et al, "The Matrix Metalloproteinases and Their Natural Inhibitors: Prospects for Treating Degenerative Tissue Diseases," *TIBTECH,* Jun. 1992, vol. 10.

Fishbein et al., *Science,* 142:1069–1070 (1963).

Galardy et al, "Inhibition of Human Skin Fibroblast Collagenase by Phosphorous–Containing Peptides," *MATRIX,* 1992, Supplement No. 1, pp. 259–262.

Gearing et al, "Processing of Tumor Necrosis Factor–α Precursor by Metalloproteinases," *Letters to Nature,* 1994, vol. 370, pp. 555–557.

Gilissen et al., *Carcinogenesis,* 15:39–45 (1994).

Gilissen et al., *Carcinogenesis,* 13:1699–1703 (1992).

Goulet et al, "Inhibition of Stromeylsin–1 (MMP–3) by Peptidyl Phosphinic Acids," *Bioorganic & Medicinal Chem. Letters,* 1994, vol. 4, No. 10, pp. 1221–1224.

Gray et al, "Design and Synthesis of Inhibitors of Porcine Synovial Collagnease and Gelatinase," *MATRIX,* 1992, Supplement No. 1, pp. 307–308.

Gray et al, "Inhibition of Mammalian Collagenases by Thiol–Containing Peptides," *J. Cell. Biochem.,* 1986, vol. 32, pp. 71–77.

Gray et al, "Metal Binding Peptide Inhibitors of Vertebrate Collagenase," *Biochem. and Biophy. Res. Comm.,* 1981, vol. 101, No. 4, pp. 1251–1258.

Grobelny et al, "Inhibition of Human Skin Fibroblast Collagenase, Thermolysin, and *Pseudomonas aeruginosa* elastase by Peptide Hydroxamic Acids," *Biochemistry,* 1992, vol. 31, pp. 7152–7154.

Hasty et al., *Arthr. Rheum.,* 33:388–397 (1990).

Henney et al., *Proc. Natl. Acad. Sci. USA,* 88:8154–8158 (1991).

Ito et al., *Arch. Biochem. Biophys.,* 267:211–216 (1988).

Johnson et al., *J. Enzym. Inhib.,* 2:1–22 (1978).

Knight et al, "A Novel Coumarin–labelled Peptide for Sensitive Continuous Assays of the Matrix Metalloproteinases," *FEBS 10610,* Jan. 1992, vol. 296, No. 3, pp. 263–266.

Kortylewicz et al, "Phosphoramidate Peptide Inhibitors of Human Skin Fibroblast Collagenase," *J. Med. Chem.,* 1990, vol. 33, pp. 263–273.

Kortylewicz et al, "Phthaloyl–Glycyl$^P$–Isoleucyl– Tryptophan Benzylamide is a Potent Inhibitor of Human Skin Fibroblast Collagenase with A $K_i$ of 25 nM," *J. Enzyme Inhibition,* 1989, vol. 3, pp. 159–162.

Krane et al., In *The Control of Tissue Damage,* A.B. Glauert (ed.), Elsevier Sci. Publ.., Amsterdam, 1988,Ch. 14, pp. 179–195.

Kronberger et al., *J. Invest. Dermatol.,* 79:208–211 (1982).

Lewis, Peter Dr., "Metalloprotease Inhibitors", *Company Report — British Biotech,* pp. 10–11.

Lin et al, "Inhibition of Human Fibroblast Collaenase by Phthaloyl–glycl$^P$–Glycyl$^P$–Isoleucyl–Tryptophan Benzylamide", *MATRIX,* 1992, Supplement No. 1, pp. 311–312.

Liotta et al., *Lab. Invest.,* 49:636–649 (1983).

Lovejoy et al, "Structure of the Catalytic Domain of Fibroblast Collagenase Complexed With an Inhibitor," *SCIENCE,* 1994, vol. 263, pp. 375–377.

Martin et al, "Cyclopropanes as Conformationally Restricted Peptide Isosteres. Design and Synthesis of Novel Collagenase Inhibitors," *Tetrahedron,* 1993, vol. 49, No. 17, pp. 3521–3532.

Matrisian et al., *Proc. Natl. Acad. Sci. USA,* 83:9413–9417 (1986).

McGeehan et al, "Regulation of Tumour Necrosis Factor–α Processing by a Metalloproteinase Inhibitor," *Letters to Nature,* 1994, vol. 370, pp. 558–561.

Mookhtiar et al, "Phosphonamidate Inhibitors of Human Neutrophil Collagenase," *Biochemisry,* 1987, vol. 26, pp. 1962–1965.

Moore et al, "Peptide Hydroxamic Acids Inhibit Skin Collagenase," *Biochem. and Biophysical Res. Comms.,* 1986, vol. 136, No. 1, pp. 390–395.

Murphy et al, *Biochem. J.,* 248:265–268 (1987).

Musser et al., *J. Med. Chem.,* 29:1429–1435 (1986).

Odake et al, "Vertebrate Collagenase Inhibitor. I. Tripeptidyl Hydroxamic Acids," *Chem. Pharm. Bull.,* 1990, vol. 38, No. 4, pp. 1007–1011.

Ogata et al., *J. Biol. Chem.,* 267:3581–3584 (1992).

Okada et al., *Eur. J. Biochem.,* 194:721–730 (1990).

Overall et al., *J. Periodontal Res.,* 22:81–88 (1987).

Pegoraro et al, "Conformationally Constrained Peptide Inhibitors of Collagenase and Gelatinase," *MEDI,* No. 126.

Peltonen et al, "Enzymes Converting Procollagens to Collagens," *J. of Cell. Biochem.,* 1985, vol. 28, pp. 15–21.

Reich et al., "Inhibitors of collagenase IV and cell adhesion reduce the invasive activity of malignant tumor cells", in *Metastasis: Ciba Foundation Symposium;* Wiley, Chichester, 1988, pp. 193–210.

Rodman et al., *R.L. Clin. Pharmacol. Ther.,* 42:346–350 (1987).

Sawamura et al., *Biochem. Biophys. Res. Commun.,* 174:1003–1008 (1991).

Schwartz et al, "Inhibition of Human Collagenases by Sulfur–Based Substrate Analogs," *Biochem. and Biophys. Res. Comms.,* 1991, vol. 176, No. 1, pp. 173–179.

Schwartz et al, "8 Synthetic Inhibitors of Bacterial and Mammalian Interstitial Collagenases," *Progress in Med. Chem.,* 1992, vol. 29, pp. 271–333, Elsevier Science Publishers B.V.

Shaw et al., *Adv. Inflam. Res.,* 12: 67–79 (1988).

Too et al., *Endocrin.,* 115:1043–1050 (1984).

Uitto et al., *J. Periodontal Res.,* 16:417–424 (1981).

Vencill et al, "*Clostridium histolyticum* Collagenase: Development of New Thio Ester, Fluorogenic, and Depsipeptide Substrates and New Inhibitors," *Biochemistry,* 1985, vol. 24, No. 13, pp. 3149–3157.

Vine et al., *Clin Sci.,* 81:233–239 (1991).

Weingarten et al, "Synthetic Substrates of Vertebrate Collagenase," *Biochemistry,* 1985, vol. 24, No. 23, pp. 6730–6734.

Whitham et al, *Biochem. J.,* 240:913–916 (1986).

Wilhelm et al, *Proc. Natl. Acad. Sci. USA*, 84:6725–6729 (1987).
Williams et al, *Arthr. Rheum.*, 33:533–541 (1990).
Williams et al, *N. Engl. J. Med.*, 311:760–764 (1984).
Winyard et al, *FEBS Lett.*, 279(1):91–94 (1991).
Woessner et al., *Steroids*, 54:491–499 (1989).

Yankeelov, Jr. et al, "Mercaptoimidazolylpropionic Acid Hydrobromide, Inhibition of Tadpole Collagenase and Related Properties," *J. of Med. Chem.*, 1978, vol. 21, No. 7, pp. 701–704.

Yoshioka et al., *Mutat. Res.*, 170:93–102 (1986).

INHIBITORS OF COLLAGENASE-1 AND STORMELYSIN-I METALLOPROTEASES, PHARMACEUTICAL COMPOSITIONS COMPRISING SAME AND METHODS OF THEIR USE

CROSS-REFERENCE TO RELATED APPLICATIONS

This application is a continuation-in-part of U.S. patent application Ser. No. 08/482,211 filed Jun. 7, 1995 which, in turn, is a continuation-in-part of U.S. patent application Ser. No. 08/329,420, filed Oct. 27, 1994, which disclosures are incorporated herein by reference in their entirety.

BACKGROUND OF THE INVENTION

1. Field of the Invention

This invention relates to novel compounds, which are inhibitors of collagenase-1 and stromelysin-I metalloproteases. Pharmaceutical compositions comprising these metalloprotease inhibitors as well as methods of their use for treating or controlling disease states or conditions associated with such enzymes are also described.

2. State of the Art

Metalloproteases are involved in a large number of disease states and other conditions in human and other animals. The metalloproteases are a family of enzymes containing zinc at the active site, which facilitates the catalytic hydrolysis of various protein substrates. A subfamily of the metalloprotease family is known as the matrix metalloproteases because these enzymes are capable of degrading the major components of articular cartilage and basement membranes. The matrix metalloproteases include stromelysin, collagenase, matrilysin and gelatinase, among others.

Stromelysin (aka. proteoglycanase, matrix metalloproteinase-3, MMP-3, procollagenase activator, "transin"), collagenase (aka. interstitial collagenase, matrix metalloproteinase-1, MMP-1, type II collagenase), and gelatinase (aka. type IV collagenase, matrix metalloproteinase-2, MMP-2, 72 kda-gelatinase or type V collagenase, matrix metalloproteinase-9, MMP-9, 95 kDa-gelatinase) are metalloendoproteinases secreted by fibroblasts and chondrocytes, and are capable of degrading the major connective tissue components of articular cartilage or basement membranes. Human rheumatoid synovial collagenase is approximately 50% identical to human stromelysin (Whitham et al., Biochem. J., 240:913–916 (1986)). Gelatinase (MR ~72,000) has been isolated from rheumatoid fibroblasts (Okada et al., Eur. J. Biochem., 194:721–730 (1990)). A higher molecular weight gelatinase (MR ~95,000; aka. type-V collagenase, matrix metalloproteinase-9, MMP-9) is also secreted by fibroblasts and monocytes and may be involved in cartilage degradation.

Metalloproteases are apparently involved in several arthritis conditions, including osteoarthritis (OA) and rheumatoid arthritis (RA). These diseases are largely due to the loss of articular cartilage. Elevated levels of stromelysin and collagenase have been detected in joints of arthritic humans and animals (Hasty et al., Arthr. Rheum., 33:388–397 (1990); Krane et al., In The Control of Tissue Damage, A. B. Glauert (ed.), Elsevier Sci. Publ., Amsterdam, 1988, Ch. 14, pp. 179–195; Blanckaert et al., Clin. Chim. Acta, 185:73–80 (1989)). Each enzyme is secreted from these cells as an inactive proenzyme which is subsequently activated. There is evidence that stromelysin may be the in vivo activator for collagenase and gelatinase, implying a cascade for degradative enzyme activity (Fo et al., Arch. Biochem. Biophys., 267:211–216 (1988); Murphy et al., Biochem. J., 248:265–268 (1987); Ogata et al., J. Biol. Chem., 267:3581–3584 (1992)). The synthesis of the gelatinase proenzyme is not coordinately regulated with the other two metalloproteinases. The role of gelatinase in the tissue destruction of articular cartilage appears different from the other two enzymes.

Stromelysin and collagenase are also implicated in the articular cartilage damage associated with septic arthritis. Bacterial infections of the joints can elicit an inflammatory response that may then be perpetuated beyond what is needed for removal of the infective agent, resulting in permanent damage to structural components. Bacterial agents have been used in animal models to elicit an arthritic response with the appearance of proteolytic activities (Case et al., J. Clin Invest., 84:1731–1740 (1989); Williams et al., Arthr. Rheum., 33:533–541 (1990)).

Secreted proteinases such as stromelysin, collagenase, and gelatinase play an important role in processes involved in the movement of cells during metastatic tumor invasion. Indeed, there is also evidence that the matrix metalloproteinases are overexpressed in certain metastatic tumor cell lines. In this context, the enzyme functions to penetrate underlying basement membranes and allow the tumor cell to escape from the site of primary tumor formation and enter circulation. After adhering to blood vessel walls, the tumor cells use these same metalloendoproteinases to pierce underlying basement membranes and penetrate other tissues, thereby leading to tumor metastasis.

Periodontal diseases such as gingivitis are also characterized by metalloprotease expression. Both collagenase and stromelysin activities have been isolated from fibroblasts isolated from inflamed gingiva (Uitto et al., J. Periodontal Res., 16:417–424 (1981)). Enzyme levels have been correlated to the severity of gum disease (Overall et al., J. Periodontal Res., 22:81–88 (1987)).

Stromelysin has been implicated in the degradation of structural components of the glomerular basement membrane (GBM) of the kidney, the major function of which is to restrict passage of plasma proteins into the urine (Baricos et al., Biochem. J., 254:609–612 (1988)). Proteinuria, a result of glomerular disease, is excess protein in the urine caused by increased permeability of the GBM to plasma proteins. The underlying causes of this increased GBM permeability are unknown, but proteinases including stromelysin may play an important role in glomerular diseases.

Metalloproteases may also be involved in the rupturing of atherosclerotic plaques leading to coronary thrombosis. The tearing or rupturing of atherosclerotic plaques is the most common event initiating coronary thrombosis. Destabilization and degradation of the connection tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin messenger RNA have been found to be localized to individual cells in atherosclerotic plaques removed from heart transplant patients at the time of surgery (Henney et al., Proc. Natl. Acad. Sci. USA, 88:8154–8158 (1991)).

Degenerative aortic disease associated with thinning of the medial aortic wall is another condition in which matrix metalloproteases may play a role. Aneurysms are often associated with atherosclerosis in this tissue. Increased levels of the matrix metalloproteinases have been identified in patients with aortic aneurysms and aortic stenosis (Vine et al., Clin. Sci., 81:233–239 (1991)).

Expression of metalloproteinases, including stromelysin and collagenase, is observed in unfertilized eggs and zygotes and at further cleavage stages and increased at the blastocyst stage of fetal development and with endoderm differentiation (Brenner et al., *Genes & Develop.*, 3:848–859 (1989)). By analogy to tumor invasion, a blastocyst may express metalloproteinases in order to penetrate the extracellular matrix of the uterine wall during implantation. In addition, evidence exists that collagenase is important in ovulation processes. Collagenase apparently facilitates penetration of a covering of collagen over the apical region of the follicle, allowing the ovum to escape. There may also be a role for stromelysin activity during ovulation (Too et al., *Endocrin.* 115:1043–1050(1984)).

Proteolytic processes have also been observed in the ulceration of the cornea following alkali burns (Brown et al., *Arch. Ophthalmol.*, 81:370–373 (1969)). Collagenolytic and stromelysin activity have also been observed in dystrophobic epidermolysis bullosa (Kronberger et al., *J. Invest. Dermatol.*, 79:208–211 (1982); Sawamura et al., *Biochem. Biophys. Res. Commun.*, 174:1003–1008 (1991)).

In addition to degrading structural components of the extracellular matrix, stromelysin can degrade other in vivo substrates, including the $\alpha_1$-proteinase inhibitor, and may therefore influence the activities of other proteinases such as elastase (Winyard et al., *FEBS Lett.*, 279(1):91–94 (1991)).

Because metalloproteases play a role in so many diseases and other conditions, inhibitors of these enzymes have been studied as possible therapeutic agents. In vitro experiments measuring the effect of matrix metalloendoproteinase inhibitors on proteoglycan release from rabbit cartilage explants suggest that stromelysin inhibition may be effective in preventing articular cartilage degradation (Caputo et al., *J. Orthopedic Res.*, 6:103–108 (1988)). Evidence also suggests that inhibitors of stromelysin, collagenase, and gelatinase will be useful to control tumor metastasis (Matrisian et al., *Proc. Natl. Acad. Sci. USA*, 83:9413–9417 (1986); Wilhelm et al., *Proc. Natl. Acad. Sci. USA*, 84:6725–6729 (1987); Liotta, et al., *Lab. Invest.*, 49:636–649 (1983); Reich et al., "Inhibitors of collagenase IV and cell adhesion reduce the invasive activity of malignant tumor cells", in Metastasis: *Ciba Foundation Symposium*; Wiley, Chichester, 1988, pp. 193–210). An inhibitor of collagenase has been shown to be effective in preventing ovulation (Woessner et al., *Steroids*, 54:491–499 (1989)). Mercapto-containing peptides inhibit the collagenase isolated from alkali-burned rabbit cornea (Burns et al., *Invest. Ophthalmol.*, 30:1569–1575 (1989)).

Thiol carboxylic acid derivatives that inhibit collagenase are disclosed in U.S. Pat. Nos. 5,109,000; 4,595,700; 4,371,466. Additional collagenase inhibitor compounds are disclosed in European Patent Application Publication Nos. 0 423 943; 0 273 689; 0 322 184; and 0 185 380, and in International Patent Application Publication Nos. WO 88/06890 and WO 94/07481.

Collagenase inhibitors have also been designed around the cleavage site of the a-chain sequence of Type II collagen (Johnson et al., *J. Enzym. Inhib.*, 2:1–22 (1987)). One such inhibitor, N-[3-(benzyloxycarbonyl)amino-1-carboxy-n-propyl]-L-leucyl-O-methyl-L-tyrosine, N-methylamide, prepared at G. D. Searle, Inc., is a potent inhibitor of human rheumatoid synovial collagenase ($IC_{50}$=0–8 $\mu$M). This compound also inhibits rabbit bone proteoglycanase ($IC_{50}$=0.5 $\mu$M) (Delaisse et al., *Biochem. Biophys. Res. Commun.*, 133:483–90 (1985)).

However, significant obstacles continue to stand in the way of clinical exploitation of metalloprotease inhibitors.

First, there is very little to guide one in developing a specific inhibitor for each enzyme. In preliminary studies of rabbit proteoglycanase with substrates and inhibitors, little was found to indicate the enzyme's requirements for hydrolysis or inhibition beyond a preference for hydrophobic residues at the $P_1'$ position (Shaw et al., *Adv. Inflam. Res.*, 12: 67–79 (1988)). More extensive studies with a series of substrates revealed that stromelysin will tolerate nearly every amino acid residue around the scissile bond (Fields et al., unpublished results presented at the Matrix Metalloproteinase Conference, Sept. 1989, Sandestin, Fla.).

Toxicity is a second obstacle to therapeutic use of previously known metalloprotease inhibitors. For example, certain hydroxamic acids have been suggested as collagenase inhibitors as in U.S. Pat. No. 4,599,361 and European Patent Application Publication No. 0 236 872. U.S. Pat. Nos. 5,304,604, 5,240,958 and 5,310,763 also disclose hydroxamic acid derivatives which act as inhibitors of metalloproteases involved in tissue degradation, such as collagenase, stromelysin (proteoglycanase), gelatinase and collagenase (IV).

Although these hydroxamic acid compounds are effective inhibitors of matrix metalloproteases, the hydroxamic acid moiety is potentially toxic. See, for example, Musser et al., *J. Med. Chem.*, 29:1429–1435 (1986); Baililien et al., *Am. J. Vet. Res.*, 74:2604–2611 (1986); Rodman et al., *R. L. Clin. Pharmacol. Ther.*, 42:346–350 (1987); Williams et al., *N. Engl. J. Med.*, 311:760–764 (1984); Yoshioka et al., *Mutat. Res.*, 170:93–102 (1986); Gillissen et al., *Carcinogenesis*, 15:39–45 (1994); Gillissen et al., *Carcinogenesis*, 13:1699–1703 (1992); Fishbein et al., *Science*, 142:1069–1070 (1963); and Borenfreund et al., *J. Nat. Cancer Inst.*, 32:667–679 (1964). As a result, there are few, if any, hydroxamic acid based drugs in use.

The wide spectrum of clinical indications for collagenase-1 and stromelysin-I metalloprotease inhibitors establishes a clear need for such matrix metalloprotease inhibitors that have satisfactory inhibition activity. It is not a simple matter, however, to predict what variations in known compounds would retain or even increase activity. The present invention fulfills this need for novel effective inhibitors of collagenase-1 and stromelysin-I.

SUMMARY OF THE INVENTION

The invention provides novel inhibitors of collagenase-1 and stromolysin-I metalloproteases that are highly active. The claimed mercaptoketone and mercaptoalcohol compounds are preferably of the following formulas I, II and III:

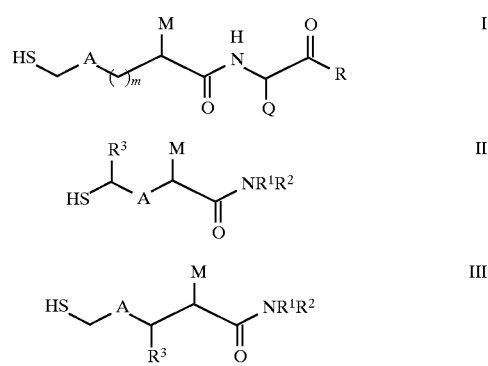

wherein
A is selected from the group consisting of >C=O and >CHOH;

M and Q are each independently selected from the group consisting of hydrogen, alkyl, substituted alkyl, aryl, heteroaryl;

R is selected from the group consisting of $-NR^1R^2$ and $-NHCH(Q')C(O)NR^1R^2$;

$R^1$ is selected from the group consisting of hydrogen, alkyl, substituted alkyl, aryl, heteroaryl, arylalkyl, heteroarylalkyl, heterocyclic and heterocyclicalkyl;

$R^2$ is hydrogen, or $R^1$ and $R^2$ together with the nitrogen atom to which they are attached, form a heterocyclic or heteroaryl ring;

Q' is selected from the group consisting of hydrogen, alkyl, substituted alkyl, aryl, and heteroaryl;

$R^3$ is $-(CH_2)_n-V$ wherein n is a whole number from 0 to 4 and V is selected from the group consisting of hydrogen, alkyl, substituted alkyl, $-OR^{13}$, $-NR^{12}R^{13}$, and $-SR^3$, wherein $R^{12}$ and $R^{13}$ are each independently hydrogen, alkyl, substituted alkyl, alkenyl, aryl, arylalkyl, $-C(O)-$alkyl, $-C(O)-$substituted alkyl, $-C(O)-$aryl, $-C(O)-$heteroaryl, heteroaryl, heterocyclic, heterocyclicalkyl or heteroarylalkyl wherein, in the case of $-NR^{12}R^{13}$, the nitrogen atom is optionally incorporated into the heteroaryl or heterocyclic ring structure; and m is an integer from 0 to 2.

Also provided are pharmaceutical compositions that include these collagenase-1 and stromelysin-I metalloprotease inhibitor compounds in an amount effective for treating or controlling disease states associated with these metalloproteases in patients in need of such treatment and a pharmaceutically acceptable carrier. Methods for treating or controlling disease states or conditions involving tissue breakdown or inflammatory conditions are also provided. These methods involve administering to a patient in need of such treatment an effective amount of the collagenase-1 and/or stromelysin-I metalloprotease inhibitor compounds, generally as a pharmaceutical composition.

BRIEF DESCRIPTION OF THE DRAWINGS

FIGS. 1–16 illustrate various compounds of the present invention and reaction schemes for preparing these compounds.

FIG. 1 illustrates the synthesis of mercaptoketone dipeptides [(S)2-isobutyl-4-oxo-5-mercapto-pentanoyl]-(L)-β-cyclohexylalanine-(2-phenylethyl) amide and [(R)-2-isobutyl-4-oxo-5-mercapto-pentanoyl]-(L)-β-cyclohexylalanine-(2-phenylethyl) amide.

FIG. 2 illustrates an experimental procedure for the synthesis of 2-isobutyl-3-oxo-4-mercapto-butanoyl-(L)-β-cyclohexylalanine-(2-phenylethyl) amide.

FIG. 3 illustrates the synthesis of 2-n-heptyl-3-hydroxy-4-mercapto-butanoyl-(L)-Leu-Leu-ethylamide, 2-n-heptyl-3-oxo-mercapto-butanol-(L)-Leu-(L)-Leu-ethylamide and related compounds.

FIG. 4 illustrates the synthesis of 2-isobutyl-3-oxo-4-mercapto-butanoyl-(—L—)-Leu-Leu-ethylamide through PNP-ester.

FIG. 5 illustrates a strategy for efficient synthesis of γ-mercapto-β-hydroxy building blocks.

FIG. 6 illustrates various protecting groups that were used in experiments to determine an optimal protecting group to block ketones during solid-support synthesis.

FIG. 7 illustrates a strategy for synthesizing a mercapto-malonyl metalloprotease inhibitor using the MOM-enol blocking group shown in FIG. 6.

FIG. 8 illustrates a variety of malonyl mercaptoalcohol and mercaptoketones that were synthesized using the synthesis strategies taught herein.

FIG. 9 illustrates a strategy for synthesizing succinyl mercaptoalcohols using diphenyl acetonides as protecting groups.

FIG. 10 illustrates a strategy for synthesizing succinyl mercaptoalcohols (8) and mercaptoketones (9).

FIG. 11 is a comparison of the stromelysin-inhibiting activity of succinyl mercaptoketones and succinyl mercaptoalcohols.

FIG. 12 illustrates a series of deoxy mercaptanes with different chain lengths between the thiol and the $P_1'$ substituent group.

FIG. 13 illustrates a strategy for synthesizing β-mercapto-α-heptyl-proprionyl-Leu-Leu-NHEt, a β-mercaptan of the type shown in FIG. 12. The dashed arrow indicates a synthesis step not yet completed.

FIG. 14 shows a hydroxymate metalloprotease inhibitor (1). Compound (2) is a mercapto derivatives of the hydroxymate.

FIG. 16 illustrates a strategy for racemic synthesis of building blocks for mercapto derivatives of hydroxymate metalloprotease inhibitor compounds. The dashed arrows indicate synthesis steps not yet completed.

DETAILED DESCRIPTION OF THE INVENTION

Figure 1:
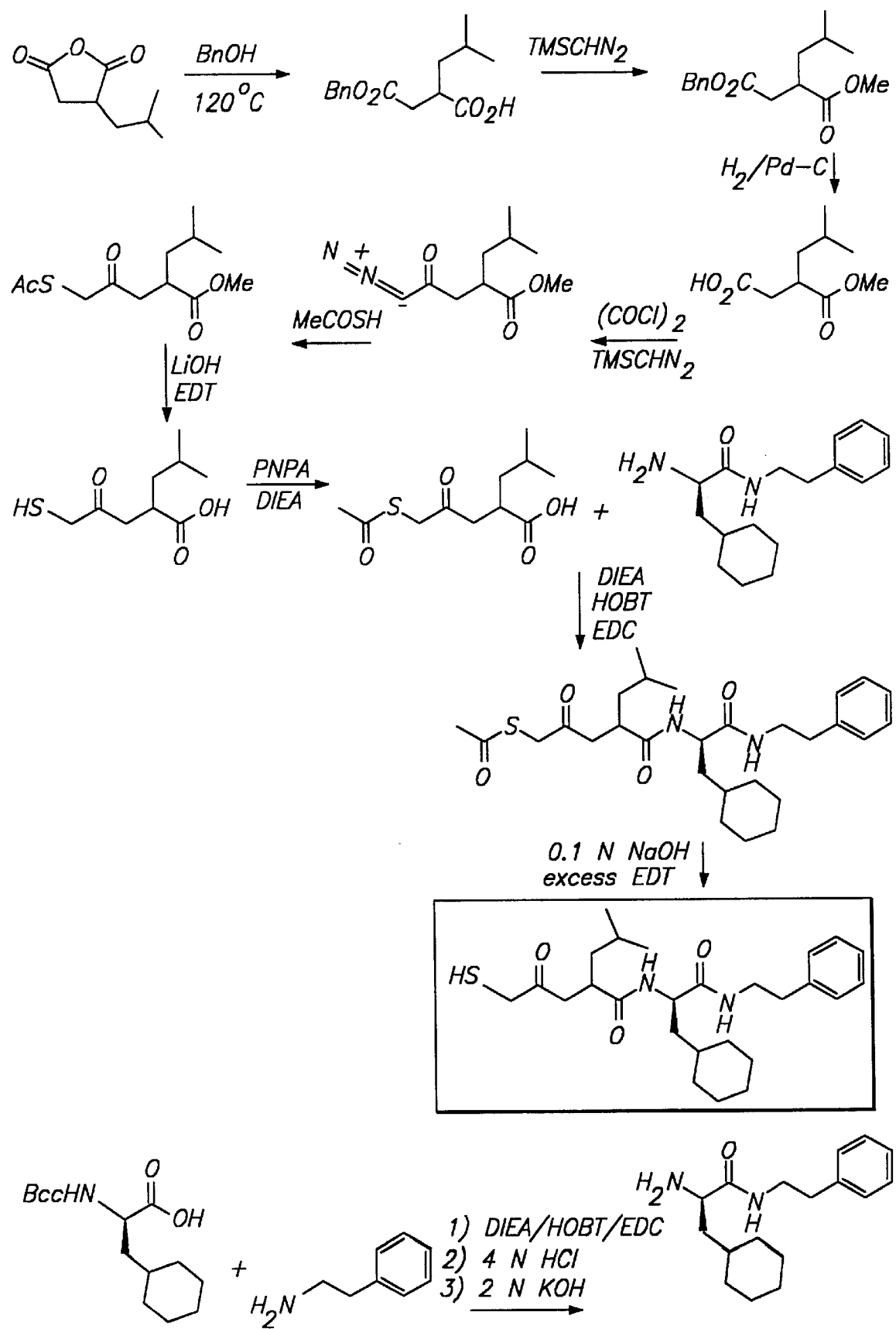

This invention provides inhibitors of collagenase-1 and stromelysin-I metalloproteases, that are useful in treating various diseases and conditions that involve tissue breakdown.

However, prior to addressing this invention in further detail, the following terms will first be defined.

As used herein, "alkyl" refers to a cyclic, branched, or straight chain alkyl group containing only carbon and hydrogen, preferably having from 1 to 12 carbon atoms and preferably 1 to 6 carbon atoms. This term is further exemplified by groups such as methyl, heptyl, $-(CH_2)_2-$, adamantyl, $-CH_2-$cyclohexyl and the like.

"Substituted alkyl" refers to a cyclic, branched, or straight chain alkyl group of from 1 to 12 carbon atoms having from 1 to 3 substituents selected from the group consisting of halogen, alkoxy, substituted alkoxy, thioalkoxy, substituted thioalkoxy (optionally wherein the sulfur atom of the thioalkoxy or substituted thioalkoxy group is oxidized to the sulfinyl or sulfonyl derivative), acyl, acyloxy, amino, N-alkylamino, N,N-dialkylamino, aminotosyl, t-butoxycarbonylamino, hydroxyl, mercapto, carboxy, carboxyalkyl, carboxamide, benzyloxy, heterocyclic, aryl, heteroaryl, and aryl substituted with from 1 to 3 substituents selected from hydroxy, alkyl, alkoxy, halo, mercapto, $-SO_2NH_2$.

"Alkoxy" refers to the group alkyl—O— which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group substituted alkyl—O—.

"Thioalkoxy" refers to the group alkyl—S— which includes, by way of example, thiomethoxy, thioethoxy, thio-n-propoxy, thio-iso-propoxy, and the like.

"Substituted thioalkoxy" refers to the group substituted alkyl—S—.

"Acyl" refers to the group alkyl—C(O)—.

"Acyloxy" refers to the group alkyl—C(O)O—.

"Alkenyl" refers to a cyclic, branched, or straight chain alkenyl groups containing only carbon and hydrogen, having at least one site of unsaturation, preferably having from 2 to 12 carbon atoms and preferably 2 to 6 carbon atoms.

"Aryl" or "Ar" refers to an unsaturated aromatic carbocyclic group of from 6 to 14 carbon atoms having a single ring (e.g., phenyl) or multiple condensed rings (e.g., naphthyl or anthryl) carbon atoms, which can optionally be unsubstituted or substituted with from 1 to 3 substituents selected from hydroxy, alkyl, alkoxy, aryloxy, halo, mercapto, nitro, —SO$_2$NH$_2$ and the like. Preferred aryls include phenyl and alkyl substituted phenyl.

"Aryloxy" refers to the group aryl—O— which includes, by way of example, phenoxy, naphthoxy, and the like.

"Arylalkyl" refers to the group -alkyl-Ar, where Ar is an aryl group. Examples of arylalkyl groups include benzyl, —CH$_2$CH$_2$φ, and the like.

"Halo" or "halogen" refers to fluoro, chloro, bromo and iodo and preferably is either chloro or bromo.

"Heteroaryl" or "HetAr" refers to a monovalent aromatic carbocyclic group of from 2 to 12 carbon atoms and 1 to 4 heteroatoms selected from oxygen, nitrogen and sulfur within the ring. Such heteroaryl groups can have a single ring (e.g., pyridyl or furyl) or multiple condensed rings (e.g., indolizinyl or benzothienyl), which can optionally be unsubstituted or substituted with hydroxy, alkyl, alkoxy, halo, mercapto, and the like. Preferred heteroaryls include pyridyl and furyl.

"Heteroarylalkyl" refers to the group -alkyl-HetAr, where HetAr is a heteroaryl group. Examples of heteroarylalkyl groups include furfuryl.

"Heterocycle" or "heterocyclic" refers to a monovalent saturated or unsaturated group having a single ring or multiple condensed rings, from 1 to 12 carbon atoms and from 1 to 4 heteroatoms selected from nitrogen, sulfur or oxygen within the ring, which can optionally be unsubstituted or substituted with hydroxy, alkyl, alkoxy, halo, mercapto, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, and indoline. Preferred heteroaryls include pyrrole and pyridine.

"Heterocyclicalkyl" refers to the group -alkyl-heterocyclic, where heterocyclic is a heterocyclic group. Examples of heterocyclicalkyl groups include —CH$_2$CH$_2$— (N-morpholine).

"Amino acid" refers to any of the naturally occurring amino acids, as well as synthetic analogs and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). See, e.g., Harper et al (1977) *Review of Physiological Chemistry*, 16th Ed., Lange Medical Publications, pp. 21–24. One of skill in the art will appreciate that the term "amino acid" also includes β-, γ-, δ-, and ω-amino acids, and the like. Unnatural amino acids are also known in the art, as set forth in, for example, Williams (ed.), *Synthesis of Optically Active α-Amino Acids*, Pergamon Press (1989); Evans et al., *J. Amer. Chem. Soc.*, 112:4011–4030 (1990); Pu et al., *J. Amer. Chem. Soc.*, 56:1280–1283 (1991); Williams et al., *J. Amer. Chem. Soc.*, 113:9276–9286 (1991); and all references cited therein.

As used herein, the twenty conventional amino acids and their abbreviations follow conventional usage (see IMMUNOLOGY-A SYNTHESIS, 2nd Edition, E. S. Golub and D. R. Gren, Eds., Sinauer Associates, Sunderland, Mass. (1991), which is incorporated herein by reference). Amino acid residues are abbreviated as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Stereoisomers (e.g., D-amino acids) of the twenty conventional amino acids, unnatural amino acids such as α,α-disubstituted amino acids, N-alkyl amino acids, and other unconventional amino acids may also be suitable components for compounds of the present invention. Examples of unconventional amino acids include: 4-hydroxyproline, O-phosphoserine, N-acetylserine, N-formylmethionine, 3-methylhistidine, 5-hydroxylysine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

The preferred compounds of the present invention comprise a pharmacophore mercaptoketone or mercaptoalcohol group. Such compounds may serve as zinc chelators and/or transition state analogs of a substrate for the active site of collagenase-1 and stromelysin-I metalloproteases. In one preferred embodiment, the compounds of this invention have formulas I and II as set forth below:

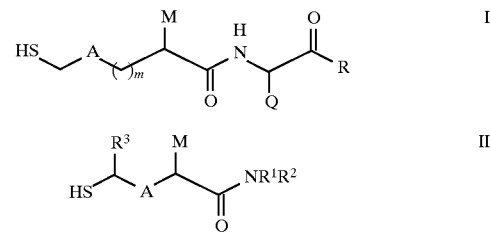

wherein A, M, Q, R, R$^1$, R$^2$, R$^3$ and m are as previously defined.

In a particularly preferred embodiment, M is iso-butyl, n-pentyl, cyclohexylpropyl, cyclohexylbutyl, cyclohexylpentyl, phenylpropyl, phenylbutyl, phenylpentyl, n-heptyl, iso-pentyl, n-hexyl, ethyl, optionally substituted phenylpropyl, optionally substituted phenylethyl, n-butyl, sec-butyl, n-propyl, 2-[4-(C$_{1-3}$)phenyl]ethyl, methyl, benzyl, 3-indolylmethyl, phenyl, 2-carboxamide ethyl, 2-carboxy ethyl, 3-(4-methoxyphenyl)propyl or 2-methylbutyl.

In another preferred embodiment, Q is cyclohexylmethyl, benzyl, 4-methoxybenzyl, 4-aminobutyl, 3-indolylmethyl, 2-napthylmethyl, iso-propyl, iso-butyl, substituted benzyl, benzyloxybenzyl, 4-hydroxybenzyl, 4-t-butoxycarbonylaminobutyl, p-chlorobenzyl, 2-benzimidazoylmethyl, t-butyl, or amino acid side chains of Arg, Leu, Gln, Ala, Gly, Glu, Pro, Tyr, Lys, Thr, Ile, Val, or Asn.

As above, R is selected from the group consisting of —NR$^1$R$^2$ and —NHCH(Q')C(O)NR$^1$R$^2$. Preferably, R$^1$ is hydrogen, methyl, 2-aminoethyl, ethyl, 2-hydroxyethyl, cyclohexyl, pentyl, 2-phenylethyl, 2-(N,N-dimethylamino) ethyl, p-sulphonamidophenylmethyl, 2-(p-sulphoamidophenyl)ethyl, 2-(2'-pyridyl)ethyl, 3-(4'-N-morpholinyl)propyl, 2-(O-benzylcarbonyl)ethyl, 2-methoxyethyl, prolinol, 2-2-ethylthioethyl, 3-(2'-N-pyrrolidonyl)propyl, 2-acetoxyethyl, phenyl, benzyl, 4-nitrobenzyl, 2-(1'-N-piperidinyl)ethyl, 2-(1'-N-pyrrolidinyl)ethyl, 3-[1'-N-(2'-(R, S)-methylpiperidinyl)] propyl, 2-[2'-(1'-N-methylpyrrolyl)]ethyl, 3-pyridylmethyl, 2-pyridylmethyl, 4-pyridylmethyl, 3-(1'-N-imidazolyl) propyl, 2-benzimidazolylmethyl, 2-(4'-N-morpholinyl) ethyl, 3-(2'-pyridyl)propyl, 2-[1'-N-(4'-N-methyl-piperazyl) ]ethyl, or β-alanine amide, and R$^2$ is hydrogen; or R$^1$ and R$^2$ and the nitrogen to which they are attached form a morpholine or a 4-N-methylpiperazine ring.

Q' is preferably phenylethyl, hydrogen, methyl, i-butyl, benzyl, or ethylthiomethyl.

R$^3$ is preferably hydrogen, methyl, 4-phthaloylaminobutyl, phthaloylamino, phthaloylaminomethyl, 2-oxypropyl, carbomethoxymethyl, 2,3-naphthaloyl-amino, 2-bromo-3-hydroxy-1,8-naphthaloylamino, phenyl-thiomethyl, thiophenylthiomethyl, benzylthiomethyl, acetylthiomethyl, thiomethyl, benzoylthiomethyl, pivaloylthiomethyl, 4-methoxyphenylthiomethyl, 4-hydroxyphenylthiomethyl, 2-thiophenethiomethyl, 4-t-butyl-phenylthiomethyl, 2,4-di-methylphenylthiomethyl, 3-bromophenylthiomethyl, 3-chloro-phenylthiomethyl, 3-methylphenylthiomethyl, 4-(N-acetyl)-aminophenylthiomethyl, phenylsulphinylmethyl, phenylsulphonylmethyl, thiophenylsulphinylmethyl, thiophenylsulphonylmethyl, benzyl, or phenyl.

More preferred compounds of the present invention are of the above formulas I and II, wherein M is iso-butyl, phenylpropyl, optionally substituted phenylethyl, or n-heptyl;

Q is cyclohexylmethyl, benzyl, 4-methoxybenzyl, 3-indolylmethyl, 2-napthylmethyl, iso-butyl, or t-butyl;

Q' is phenylethyl;

R$^1$ is methyl, ethyl, 2-phenylethyl, p-sulphonamidophenylmethyl, 2-(p-sulphonamidophenyl)ethyl, phenyl, benzyl, 2-(4'-N-morpholinyl)ethyl, 2-[1'-N-(4'-N-methylpiperazyl)] ethyl or 2-pyridyl, and R$^2$ is hydrogen; or R$^1$ and R$^2$ and the nitrogen to which they are attached form a morpholine or a 4-N-methylpiperazine ring.

Additional preferred compounds of the invention are of formula III:

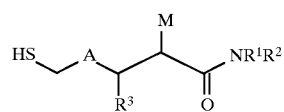

wherein M, A, R$^1$, R$^2$ and R$^3$ are as defined above.

In a preferred embodiment, the V substituent of R$^3$ is selected from the group consisting of:
—OR$^4$, wherein R$^4$ is hydrogen, alkyl, aryl, or arylalkyl;
—NR$^4$R$^5$, wherein R$^4$ and R$^5$ are each independently hydrogen, alkyl, heteroalkyl, aryl, or arylalkyl. These compounds include those in which R$^4$ and/or R$^5$ is —C(O)R$^{4'}$ where R$^{4'}$ is hydrogen, alkyl, aryl or arylalkyl.

In another preferred embodiment of compounds of formula III, R$^3$ is

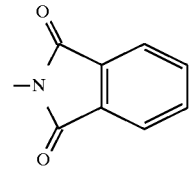

As used herein, compounds of the present invention include derivatives of the above formulas I, II and III having any substitutions which do not eliminate or significantly reduce their ability to bind to collagenase-1 and stromelysin-I metalloproteases. For example, as previously stated, the compounds of the present invention are optionally substituted with a functional group. Any art-recognized functional group which does not eliminate or significantly reduce the compound's ability to bind these metalloproteases are contemplated, including, but not limited to ester, amide, acid, amine, alcohol, ether, and thioether, etc. Symmetrical and asymmetrical disulfides are also specifically included in the compounds of the present invention.

In addition, compounds of this invention can, depending on the nature of the functional groups, form addition salts with various inorganic and organic acids and bases. Salts of these compounds include, for example, salts of inorganic acids such as hydrogen halide acids (e.g., hydrochloric acid and hydrobromic acid), sulfuric acid, nitric acid, and phosphoric acid, salts of organic acids such as acetic acid, propionic acid, glycolic acid, pyruvic acid, oxalic acid, malic acid, malonic acid, succinic acid, maleic acid, fumaric acid, tartaric acid, citric acid, cinnamic acid, mandelic acid, methanesulfonic acid, ethanesulfonic acid, p-toluenesulfonic acid, salicylic acid and benzoic acid, and salts of alkali metals such as lithium, sodium and potassium. Salts can also be formed from a carboxylic acid and an organic base, such as trimethylamine, diethylamine, ethanolamine, piperidine, isopropylamine, choline, caffeine, and the like.

Solvates, e.g., hydrates, of the compounds of the present invention are also included within the scope of the present invention. Methods of solvation to produce such solvates are generally known in the art.

There are several chiral centers in the compounds of the present invention because of the presence of asymmetric carbon atoms. The presence of several asymmetric carbon atoms gives rise to a number of diastereomers with the appropriate R or S stereochemistry at each chiral center. It is understood that the compounds of this invention include all possible stereoisomers and combinations of stereoisomers for the compounds of formula I, II and III above.

Particularly preferred compounds include the following:
2-iso-butyl-4-oxo-5-mercapto-pentanoyl-(L)-β-cyclohexylalanine-phenethylamide;
2-iso-butyl-3-oxo-4-mercapto-butanoyl]-(L)-β-cyclohexylalanine-phenethyl-amide;
2-iso-butyl-3-hydroxy-4-mercapto-butanoyl-(L)-β-cyclohexylalanine-phenethylamide;
2-iso-butyl-3-oxo-4-mercapto-butanoyl]-(L)-Leu-(L)-Leu-ethylamide;
2-n-heptyl-3-hydroxy-4-mercapto-butanoyl-(L)-Leu-(L)-Leu ethylamide;
2-n-heptyl-3-oxo-4-mercapto-butanoyl-(L)-Leu-(L)-Leu-ethylamide;
2-n-heptyl-3-hydroxy-4-mercapto-butanoyl-(L)-β-cyclohexylalanine-phenethylamide;
2-n-heptyl-3-oxo-4-mercapto-butanoyl-(L)-β-cyclohexylalanine-phenethylamide;
2-(3-phenylpropyl)-3-hydroxy-4-mercapto-butanoyl-(L)-Leu-(L)-Leu-ethylamide;
2-(3-phenylpropyl)-3-oxo-4-mercapto-butanoyl-(L)-Leu-(L)-Leu-ethylamide;
2-(3-phenylpropyl)-3-hydroxy-4-mercapto-butanoyl-(L)-β-cyclohexylalanine-phenethylamide;
2-(3-phenylpropyl)-3-oxo-4-mercapto-butanoyl-(L)-β-cyclohexylalanine-phenethylamide;
2-iso-butyl-4-oxo-5-mercapto-pentanoyl-(L)-β-t-butylglycine-(2-pyridyl)amide;
2-iso-butyl-4-hydroxy-5-mercapto-pentanoyl-(L)-β-t-butylglycine(2-pyridyl)amide (including both the D and the L isomers of the 4 hydroxy substituent);
2-iso-butyl-4-hydroxy-5-mercapto-pentanoyl-(L)-β-cyclohexylalanine-phenethylamide;
2-iso-butyl-3-hydroxy-4-mercapto-butanoyl-(L)-t-butylglycine-methylamide;
2-iso-butyl-3-oxo-4-mercapto-butanoyl-(L)-t-butylglycine-methylamide;
2-iso-butyl-4-hydroxy-5-mercapto-pentanoyl-(L)-t-butylglycine-methylamide;
2-n-heptyl-4-hydroxy-5-mercapto-pentanoyl-(L)-Leu-(L)-Leu-ethylamide;
2-n-heptyl-4-oxo-5-mercapto-pentanoyl-(L)-Leu-(L)-Leu-ethylamide;
2-n-heptyl-3-hydroxy-4-mercapto-butanoyl-(L)-t-butylglycine-methylamide;
2-n-heptyl-3-oxo-4-mercapto-butanoyl-(L)-t-butylglycine-methylamide;
2-n-heptyl-4-hydroxy-5-mercapto-pentanoyl-(L)-t-butylglycine-methylamide;
2-n-heptyl-4-oxo-5-mercapto-pentanoyl-(L)-t-butylglycine-methylamide;
2-n-heptyl-3-hydroxy-4-mercapto-butanoyl-(L)-Leu-phenethylamide;
2-n-heptyl-3-oxo-4-mercapto-butanoyl-(L)-Leu-phenethylamide;
2-n-heptyl-3-oxo-4-mercapto-butanoyl-(L)-Leu-2-N-morpholino-ethylamide;
2-n-heptyl-3-hydroxy-4-mercapto-butanoyl-(L)-Leu-2-N-morpholino-ethylamide;
2-n-heptyl-3-hydroxy-4-mercapto-butanoyl-(L)-β-cyclohexylalanine-2-(4-sulphonamide-phenyl)ethylamide; and
2-n-heptyl-3-hydroxy-4-mercapto-butanoyl-(L)-ε-N-tosyl-Lysine-(L)Leu-ethylamide.

Compounds of the present invention are prepared by several reaction schemes such as those set forth in the attached Figures. In general, compounds of the present invention are prepared by the following reaction schemes.

For example, the compounds according to the invention may be prepared by the following processes. In the description and the formula's below the groups $R^1$, $R^2$, $R^3$, and M are defined as above, except where otherwise indicated.

A compound of formula (1)

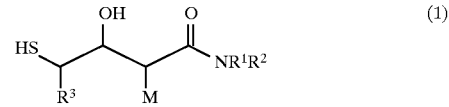

may be prepared by the deprotection of a compound of formula (2)

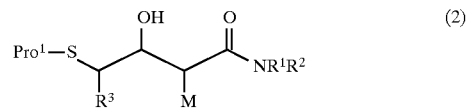

for example, when the protecting group $Pro^1$ is trityl, deprotection can be effected by acid treatment (e.g., trifluoroacetic acid (TFA)) under reducing conditions (triethylsilane (TES)), or when $Pro^1$ is an acetyl group, deprotection can be effected by hydrolysis with an alkali metal base (e.g., sodium hydroxide) in the presence of a reducing agent (e.g., 1,2-ethanedithiol (EDT)) in organic or mixed aqueous/organic solvents (e.g., methanol, dioxane/water, and the like).

A compound of formula (2) may be prepared by coupling an acid of formula (3)

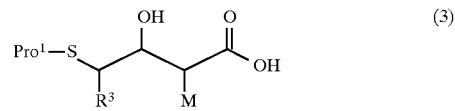

or an active derivative thereof, with an amine of formula (4)

Amines of formula (4) are either known compounds or can be prepared by methods analogous to those used for the preparation of the known compounds.

A variety of coupling agents may be used for this coupling, including 1-(3-dimethylaminopropyl)-3-ethylcarbodiimide hydrochloride (EDC) with 1-hydroxybenzotriazole (HOBt); dicyclohexylcarbodiimide (DCC) with HOBt; benzotriazol-1-yloxytris(dimethylamino)phosphonium hexafluorophosphate(BOP) with or without HOBt; carbonyldiimidazole (CDI). Active derivatives of (3) include, for example, acid anhydrides, acid halides (e.g., acid chlorides), or active esters (e.g., esters of pentafluorophenol, 4-nitrophenol, and the like).

An acid of formula (3) may be prepared by the hydrolysis of an ester of formula (5)

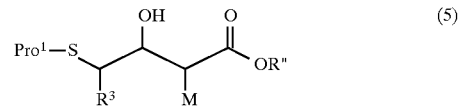

using methods known in the art. For example, when R" is methyl, hydrolysis can be carried out using an alkali metal base (e.g., lithium hydroxide) in organic or mixed aqueous/organic solvents (e.g., methanol, dioxane/water, and the like).

An ester of formula (5) can be prepared by alkylation of an α-mercapto-aldehyde of formula (6)

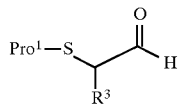

wherein $Pro^1$ is a sulfur-protecting group (e.g., trityl) with an anion generated from an ester of formula (7)

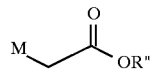

wherein R" may be any common ester forming group (e.g., lower alkyl, benzyl, and the like). The alkylation is effected by treatment of the ester (7) dissolved in an organic solvent (e.g., tetrahydrofuran(THF)) at a low temperature (e.g., −78° C.) with a base (e.g., lithium diisopropylamide (LDA)) followed by addition of the aldehyde (6).

An aldehyde of formula (6) may be prepared from a compound of formula (8)

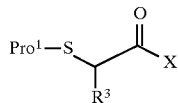

A variety of reducing agents may be used for this reduction depending on the compound used (i.e., nature of substituents). For example, when X is a methoxide, the reaction may be achieved in an organic solvent (e.g., toluene) at a low temperature (e.g., −78° C.) in the presence of a reducing agent (e.g., diisobutylaluminum hydride, (DIBAL)).

Compounds of formula (9)

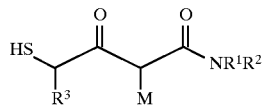

may be prepared by the deprotection of compounds of formula (10)

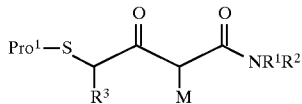

using conditions described for the deprotection of (2).

Compounds of formula (10) may be prepared by treatment of the active ester (11)

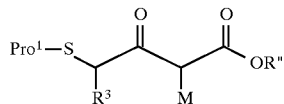

with an amine of formula (4). The condensation may be effected by treatment of the ester (11) (R"=4-nitrophenyl, 2,4, dinitrophenyl, pentafluorophenyl, and the like) with an amine of formula (4) in an organic solvent (e.g., dioxane, dichoromethane (DCM), dimethylformamide (DMF) and the like) in the presence of an organic base (e.g., diisopropylethylamine DIEA)).

Esters of formula (11) may be prepared by treatment of an alcohol of formula (5)

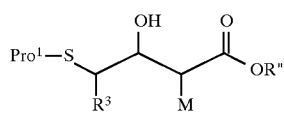

with a suitable oxidizing agent. For example, when R" is 4-nitrophenyl, the oxidation is effected in an organic solvent (DCM) with an oxidant (e.g., Dess-Martin reagent) in the presence of an organic base (e.g., pyridine).

According to a further aspect of this invention compounds of formula (12)

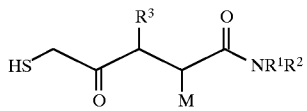

may be prepared by the deprotection of compounds of formula (13)

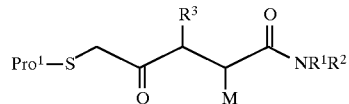

using conditions described for the deprotection of (2).

Compounds of formula (8) may be prepared by coupling an acid of formula (14)

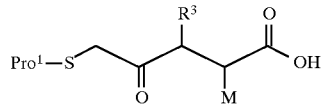

with an amine of formula (4) using conditions described for the synthesis of (2).

Acids of formula (14) may be prepared from acids of formula (15)

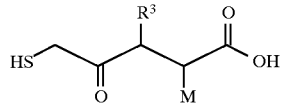

by treatment of the sulfhydryl group with an appropriate protecting group (e.g., trityl, acetyl, and the like). For example, treatment of the mercapto-acid (15) with an acetylating reagent (e.g., p-nitrophenyl acetate), in the presence of an organic base (e.g., DIEA) at room temperature in an organic solvent (e.g. DCM) yields the protected mercapto-acid (14).

Acids of formula (15) may be prepared by hydrolysing a corresponding ester of formula (16)

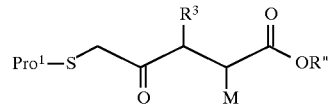

where R' is an alkyl group, for example a methyl group, hydrolysis can be effected by treatment with an alkali metal base (e.g., lithium hydroxide) in the presence of a reducing agent (e.g., EDT) at room temperature in a degassed organic solvent (e.g., methanol).

Esters of formula (16) may be prepared from succinates of formula (17)

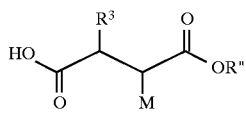

by a two step process in which the acid is first converted to a diazoketone of formula (18)

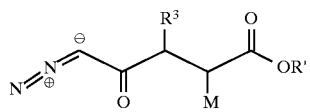

followed by treatment with thioacetic acid to yield compounds of formula (16). The diazoketone (18) is formed by treatment of the acid (17) with oxalyl chloride, catalytic DNF, in an organic solvent (e.g., ether) at room temperature, followed by the addition of (trimethylsilyl) diazomethane. Treatment of the diazoketone (18) with a sulfhydryl compound (e.g., thioacetic acid) at room temperature provides the esters of formula (4).

Intermediates of formula (17) are either known compounds or can be prepared by methods analogous to those used for the preparation of the known compounds.

Sidechain protecting groups may be used in this process for the amines of formula (4) having reactive functionalities, such as hydroxyl, carboxyl, amino, mercapto, guanidino, imidazolyl, indolyl and the like. The particular protecting groups used for any functional group requiring protection are generally known in the art. Exemplary sidechain protecting groups are acetyl, benzoyl, benzyl, t-butyl, and the like for hydroxyl; cyclohexyl, benzyl, methyl, ethyl, t-butyl, and the like for carboxyl; benzyl, 4-methylbenzyl, 4-methoxybenzyl, acetyl, acetamidomethyl, trephenylmethyl (trityl) and the like for mercapto; t-butyoxycarbonyl (Boc), benzyloxycarbonyl (Cbz), 9-fluroenylmethoxycarbonyl (Fmoc), phthaloyl (Pht), P-toluenesulfonyl (Tos), trifluoroacetyl, 2-(trimethylsilyl)-ethoxycarbonyl (TEOC), and the like for amino; 2,4-dinitrophenyl, benzyloxymethyl, Tos, Boc, Trityl, and the like for imidazolyl; formyl, Cbz, TEOC, 2,2,2-trichloroethyl carvamate (TROC), and the like for indolyl; and tosyl, nitro, bis(1-adamantyloxycarbonyl) and the like for guanidino.

Functional group protecting groups may be removed, if desired, by treatment with one or more deprotecting agents in an inert solvent of solvent mixture. For examples of protecting groups and suitable deprotecting agents, see Bodansky, M. and Bodansky, A., *The Practice of Peptide Synthesis*, Springer-Verlag, Inc. (1984); and Greene, T. W. and Wuts, P., *Protective Groups in Organic Synthesis* (2d ed.), John Wiley & Sons, Inc. (1991).

Utility

As previously stated, the compounds of the present invention have been found to be inhibitors of collagenase-1 and stromelysin-I.

Appropriate assay conditions for collagenase-1 and stromelysin-I metalloprotease inhibition activity of the compounds of the present invention can be found, for example, in Knight et al., *FEBS Letters* 296(3):263–266(1992), and U.S. Pat. Nos. 4,743,587 and 5,240,958, which reference Cawston et al., *Anal. Biochem*, 99:340–345 (1979), Cawston et al., *Methods in Enzymology* 80:771 et seq. (1981); Cawston et al., *Biochem. J.*, 195:159–165 (1981) and Weingarten et al., *Biochem. Biophys. Res. Comm.*, 139:1184–1187 (1984), which references are hereby incorporated by reference. Any standard method for analyzing the breakdown of these structural proteins can, of course, be used.

More specifically, the ability of candidate compounds to inhibit collagenease-1 and stromelysin-I metalloprotease activity can be tested in the assays described above. Isolated collagenease-1 and stromelysin-I metalloprotease enzymes can be used to confirm the inhibiting activity of the invention compounds, or crude extracts which contain these enzymes can be used.

For example, assays of in vitro inhibition activity against a carboxyl terminal truncated form of human stromelysin-I were conducted as follows. The buffer was prepared from 50 mM of N-[2-hydroxyethyl]piperazine-N'-[2-ethanesulfonic acid] (HEPES) (pH 7.0) containing 5 mM calcium, 0.02% of 23 lauryl ether (Brij) and 0.5 mM cysteine and was degassed by vacuum for more than 30 minutes. The methanol (MeOH), which is used for dilution of the inhibitor to the desired concentration, was degassed by bubbling argon for more than 30 minutes. For dilution, a sufficient amount of MeOH was then added to the compounds of the present invention to obtain a 10 mmol solution. For the assay, 20 μL of the MeOH/inhibitor solution was added to 460 μL of buffer, to which 20 μL of 100 nM of stromelysin was then added. The resulting solution was left for three minutes, after which time 5 μL of 100 μM of (7-methoxycoumarin-4-yl) acetyl-Pro-Leu-Gly-Leu-[3-(2',4'-dinitrophenyl)-L-2,3-diaminopropionyl]-Ala-Arg-NH$_2$ (Mca-peptide)(in dimethyl sulfoxide (DMSO)) was added. The fluorescence intensity increase was measured using a fluoremeter, with excitation wavelength centered around 328 nm (slit of 5 nm) and emission wavelength centered around 393 nm (slit of 10 nM). The slope at each inhibitor concentration was then measured. The slope versus inhibition concentration was next fit into the IC$_{50}$ equation of $$y = y_0(1 + [In]/IC_{50}) + B$$

ENZFIT or GRAFIT computer programs can be used to these calculations. Measurable activities were obtained for all inhibitors at concentrations less than or equal to 100 micromolar.

Activities for particularly preferred compounds of the following formulas were measured and determined to be as follows:

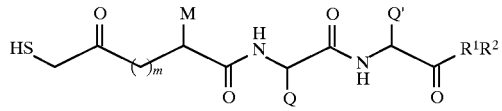

wherein M is phenylpropyl, heptyl or isobutyl, Q is isobutyl, Q' is isobutyl, R$^1$ is H, R$^2$ is ethyl and m is 0 were less than 1000 nM;

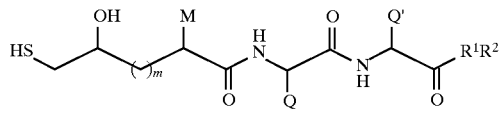

wherein M is phenylpropyl or isobutyl, Q is isobutyl, Q' is isobutyl, R$^1$ is H, R$^2$ is ethyl and m is 0 were less than 1000 nM;

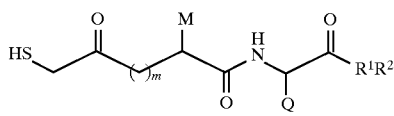

wherein M is heptyl, isobutyl or phenylpropyl, Q is cyclohexyl, $R^1$ is H, $R^2$ is phenylpropyl and m is 0 or 1 were less than 500 nM;

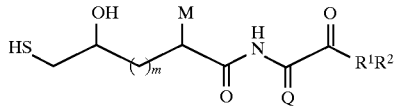

wherein M is isobutyl, Q is cyclohexylmethyl, $R^1$ is H, $R^2$ is phenylpropyl and m is 1 were less than 500 nM; and wherein M is phenylpropyl or isobutyl, Q is cyclohexylmethyl, $R^1$ is H, $R^2$ is phenylpropyl and m is 0 were generally greater than 1000 nM and in some cases greater than 10,000 nM.

Pharmaceutical Compositions

The invention also provides pharmaceutical compositions that include the collagenase-1 and/or stromelysin-I metalloprotease inhibitors described herein. The pharmaceutical compositions comprise the compounds of the present invention in an amount effective to treat or control disease states associated with such metalloproteases in humans or other animals in need of such treatment. Such disease states involve, for example, tissue degradation and inflammatory conditions. Conditions treatable with the pharmaceutical compositions include, for example, osteoarthritis, rheumatoid arthritis, septic arthritis, articular cartilage degradation, tumor invasion in certain cancers, periodontal disease, dermatological conditions, bone resorption, arthropathy, corneal ulcerations, proteinuria, dystrophobic epidermolysis bullosa, coronary thrombosis associated with atherosclerotic plaque rupture, aneurysmal aortic disease, Crohn's disease, multiple sclerosis and the cachexia associated with cancer or human immunodeficiency virus infection. The collagenase-1 and stromelysin-I metalloprotease inhibitors also promote wound healing. The present compounds are also designed to be effective birth control agents.

Pharmaceutical salts of the compounds of the present invention suitable for administration by a variety of routes are known in the art and need not be described herein in detail. Examples of pharmaceutically-acceptable salts of the compounds and derivatives thereof according to the invention, include base salts, e.g., derived from an appropriate base, such as alkali metal (e.g., sodium), alkaline earth metal (e.g., magnesium, ammonium, and $NW_nH_m$ bases and salts wherein each of n and m are 0 to 4 and n+m is 4, and wherein W is a $(C_1-C_{18})$alkyl. Pharmaceutically acceptable salts of an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-toluylsulfonic acids, and inorganic acids such as hydrochloric, sulfuric, phosphoric and sulfamic acids. Pharmaceutically-acceptable salts of a compound with a hydroxy group include, but are not limited to, the anion of the compound in combination with a suitable cation such as sodium ($Na^+$), and $NW_nH_m$, wherein W is a $(C_1-C_{18})$alkyl group, and n and m are 0 to 4, and n+m is 4.

Also part of this invention is a pharmaceutical composition of matter for treating or controlling disease states or conditions involving tissue breakdown or inflammatory conditions comprising at least one compound of the invention described above, mixtures thereof, and/or pharmaceutical salts thereof; and a pharmaceutically-acceptable carrier therefore. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

For therapeutic use in a method of treating or controlling disease states or conditions involving tissue breakdown or inflammatory conditions, a compound of the present invention or its salt can be conveniently administered in the form of a pharmaceutical composition comprising at least one of the compounds of the present invention or a salt thereof; and a pharmaceutically acceptable carrier therefor. Suitable carriers are well known in the art and vary with the desired form and mode of administration of the pharmaceutical composition. For example, they may include diluents or excipients such as filler, binder, wetting agents, disintegrators, surface-active agents, lubricants and the like. Typically, the carrier may be a solid, liquid or vaporizable carrier, or combinations thereof. In one preferred embodiment, the composition is a therapeutic composition and the carrier is a pharmaceutically-acceptable carrier.

The compounds of the invention or salts thereof may be formulated together with the carrier into any desired unit dosage form. Typical unit dosage forms include tablets, pills, powders, solutions, suspensions, emulsions, granules, capsules, suppositories.

Each carrier must be "acceptable" in the sense of being compatible with the other ingredients in the formulation and not injurious to the patient. The carrier must be biologically acceptable and inert, i.e., it must permit the cell to conduct its metabolic reactions so that the compound of this invention may effect its inhibitory activity.

Formulations include those suitable for oral, rectal, nasal, topical (including buccal and sublingual), vaginal and parenteral (including subcutaneous, intramuscular, intravenous and intradermal) administration, with parenteral formulations being preferred.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further comprise oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation. The compound of the invention may be present in the composition in a broad proportion to the carrier, so long as an effective amount of the collagenase-1 and/or stromelysin-I inhibitor reaches the site of tissue breakdown. For instance, the compound may be present in the amount of 0.01 to 99.9 wt %, and more preferably in about 0.1 to 99 wt %. Still more preferably, the compound may be present in an amount of about 1 to 70 wt % of the composition.

The invention also provides a method of treating or controlling disease states involving tissue breakdown or inflammatory conditions in a patient comprising administering to a patient a therapeutically effective amount of the composition of this invention comprising any of the compounds of the present invention, pharmaceutically-acceptable salts thereof, or mixtures thereof.

An "effective amount" of a collagenase-1 and/or stromelysin-I metalloprotease inhibitor is that dosage which is sufficient to partially or completely arrest the tissue breakdown or inflammation. The dosage of the collagenase-1 and/or stromelysin-I metalloprotease inhibitor compounds, pharmaceutically-acceptable salts or mixtures thereof, in the compositions of the invention administered to a patient will vary depending upon several factors, including, but not limited to, the age and weight of the patient, the type of disease state treated, how advanced the disease state is, the general health of the patient, the severity of the symptoms, whether the collagenase-1 and/or stromelysin-I metalloprotease inhibitor is being administered alone or in combination with other therapies or other active ingredients, the incidence of side effects and the like.

In general, a dose suitable for application in the treatment of the above-mentioned conditions is about 0.001 to 100 mg/kg body weight/dose, preferably about 0.01 to 60 mg/kg body weight/dose, and still more preferably of about 0.1 to 40 mg/kg body weight/dose per day. The desired dose may be administered as 1 to 6 or more subdoses administered at appropriate intervals throughout the day. The compounds may be administered repeatedly over a period of months or years, or it may be slowly and constantly infused to the patient. Higher and lower doses may also be administered. The daily dose may be adjusted taking into account, for example, the above identified variety of parameters. Typically, the present compound may be administered in an amount of about 0.001 to 100 mg/kg body weight/day. However, other amounts may also be administered. To achieve good plasma concentrations, the active compounds may be administered, for instance, by intravenous injection of an approximate 0.1 to 5% solution of the active ingredient, optionally in saline, or orally administered as a bolus.

The compound according to the invention, also referred to herein as the active ingredient, may be administered for therapy by any suitable routes, including oral, rectal, nasal, vaginal and parenteral (including intraperitoneal, subcutaneous, intramuscular, intravenous and intradermal) routes. It will be appreciated that the preferred route will vary with the condition and age of the patient, the nature of the disorder and the chosen active ingredient including other therapeutic agents. Preferred is the oral or intravenous route. However, other routes may also be utilized depending on the conditions of the patient and how long-lasting the treatment is.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents. The disease state may be treated by administration of the collagenase-1 and/or stromelysin-I metalloprotease inhibitors by themselves or in a combination with other active ingredients in a pharmaceutical composition. Other therapeutic agents suitable for use herein are any compatible drugs that are effective by the same or other mechanisms for the intended purpose, or drugs that are complementary to those of the present agents. These include agents that are effective for the treatment of disease states involving tissue breakdown or inflammatory conditions in humans. Examples include any of those known in the art, such as PMN elastase inhibitors such as those described in European Patent Application 337 549, glucagon, dextrose, diazoxide, phenytoin, thiazide diuretics and somatostatin, among others.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained.

The present invention also includes prodrugs of the compounds of formulas I, II and III above. Various forms of prodrugs are well known in the art, for example, as set discussed in Bundgaard (ed.), *Design of Prodrugs*, Elsevier (1985); Widder et al. (ed.), *Methods in Enzymology*, vol. 42, Academic Press, 309–396 (1985); Krogsgaard-Larsen et al. (ed.), "Design and Application of Prodrugs, *Textbook of Drug Design and Development*, Chapter 5, 113–191 (1991); Bundgaard, *Advanced Drug Delivery Reviews*, 8:1–38 (1992); Bundgaard et al., *Journal of Pharmaceutical Sciences*, 77:285 et seq. (1988); and Kakeya et al., *Chem. Pharm. Bull.*, 32:692 et seq. (1984).

In order to further illustrate the present invention and the advantages thereof, the following specific examples are given, it being understood that the same is intended only as illustrative and in nowise limitative. In the examples below as well as elsewhere in this specification, all temperatures are in degrees Celcuis (°C.). Also, in the examples below as well as elsewhere in the specification, the following abbreviations are intended to have the meanings set forth below. If not defined, the abbreviation has its generally accepted meaning:

| | | |
|---|---|---|
| atm | = | atmosphere |
| BnOH | = | benzyl alcohol |
| Boc | = | butyloxycarbonyl |
| BOP | = | benzotriazol-1-yloxytris(dimethylamino) phosphonium hexafluorophosphate |
| br d | = | broad doublet |
| br dd | = | broad doublet of doublets |
| br m | = | broad multiplet |
| br s | = | broad singlet |
| br t | = | broad triplet |
| CSA | = | camphorsulfonic acid |
| $^{13}$C—NMR | = | carbon 13 nuclear magnetic resonance spectroscopy |
| d | = | doublet |
| DBU | = | 1,8-diazabicyclo[5.4.0]undec-7-ene |
| DCC | = | 1,3-dicyclohexylcarbodiimide |
| DCM | = | dichloromethane |
| dd | = | doublet of doublets |
| ddd | = | doublet of doublets of doublets |
| dt | = | doublet of triplets |
| Dess-Martin Reagent | = | oxidizing agent described by Ireland, et al., J. Org. Chem., 58:2899 (1993) |
| DIBAL | = | di(iso-butyl)aluminum hydride |
| DIC | = | diisopropylcarbodiimide |
| DIEA | = | diisopropylethylamine |

-continued

| | | |
|---|---|---|
| DMAP | = | 4-dimethylaminopyridine |
| DMF | = | dimethyl formamide |
| EDC=EDCI | = | 1-(3-dimethylaminopropyl)-3-ethylcarbodiimide |
| EDT | = | ethanedithiol (1,2-ethanedithiol) |
| EE | = | ethoxyethyl |
| equiv. | = | equivalents |
| g | = | gram |
| $^1$H—NMR | = | proton nuclear magnetic resonance spectroscopy |
| HOBt | = | 1-hydroxybenzotriazole |
| LDA | = | lithium diisopropylamide |
| LiHMDS | = | lithium bis(trimethylsilyl)amide |
| m | = | multiplet |
| M | = | molar |
| mg | = | milligram |
| mL | = | milliliter |
| mm | = | millimeter |
| mmol | = | millimol |
| MOM | = | methoxymethyl |
| m.p. | = | melting point |
| N | = | normal |
| PNP | = | p-nitrophenol |
| PNPA | = | p-nitrophenyl acetate |
| s | = | singlet |
| t | = | triplet |
| TBAF | = | tetrabutylammonium fluoride |
| TES | = | triethylsilane |
| TFA | = | trifluoroacetic acid |
| TF$_2$O | = | trifluoromethane sulfonic anhydride |
| THF | = | tetrahydrofuran |
| TLC | = | thin layer chromatography |
| TMSethanol | = | trimethylsilylethanol |
| TMSCHN$_2$ | = | (trimethylsilyl)diazomethane |
| trityl-SH | = | triphenylmethyl mercaptan |
| TrOH | = | triphenylmethyl alcohol |
| TS$^{-+}$NBu$_4$ | = | triphenylmethylmercaptan tetrabutylammonium salt |
| TsOH | = | p-toluene sulfonic acid |
| μL | = | microliter |

EXAMPLES

Example 1

Synthesis of Mercaptoketone Dipeptides [(S)-2-Isobutyl-4-Oxo-5-Mercapto-Pentanoyl]-(L)-β-Cyclohexylalanine-Phenethylamide and [(R)-2-Isobutyl-4-Oxo-5-MercaptoPentanoyl-(L)-β-Cyclohexylalanine-Phenethylamide The synthesis of the title compound is illustrated in the attached FIG. 1.

A. 4-Benzyloxy-2-Isobutyl Succinic Acid

BnOH (2.80 g, 25.9 mmol, 2 equiv.) was added to 3-isobutyl-succinic anhydride (2.00 g, 12.8 mmol) and the mixture was heated overnight at 120° C. The majority of excess BnOH was distilled away at the same temperature under vacuum. The residue was then dissolved in 5% sodium bicarbonate aqueous solution (200 mL). This aqueous solution was washed with petroleum ether (30 mL×4) and the organic extracts were discarded. The aqueous solution was acidified with 10% hydrogen chloride (HCl) to pH 3 and extracted with ethyl acetate (40 mL×4). The combined extracts were then dried over sodium sulfate and concentrated to dryness, yielding a colorless oil as the desired mono benzylester (3.10 g, 91%) as a colorless oil. $^1$H NMR (400 MHz, CDCl$_3$) δ=0.90 (3 H, d, J =6.4 Hz), 0.93 (3 H, d, J=6.3 Hz), 1.25–1.39 (1 H, m), 1.55–1.70 (2 H, m), 2.50 (1 H, dd, J=5.1, 16.8 Hz), 2.75 (1 H, dd, J=9.1, 16.8 Hz), 2.90–2.99 (1 H, m), 5.11 (1 H, d, J=13.3 Hz), 5.16 (1 H, d, J=13.3 Hz), 5.09–5.18 (5 H, m); LRMS calculated for C$_{15}$H$_{21}$O$_4$(M+H) 265.3, found 265.3.

B. Methyl-Benzyl-2-Isobutyl Succinate

The mono acid (0.79 g, 3.0 mmol) from A above was dissolved in 10 mL MeOH and 4 mL benzene. The solution was then cooled to 0° C. and TMSCHN$_2$ (4 mL, 2.0M/hexane) was added dropwise. The bright yellow solution was stirred at room temperature for 30 minutes. Volatiles were evaporated under vacuum and the residue was column chromatographed on silica gel with 10–20% ether/petroleum ether to yield 714 mg (86%) of the desired methyl ester as an oil. $^1$H NMR (400 MHz, CDCl$_3$) δ=0.88 (3 H, d, J=6.2 Hz), 0.91 (3 H, d, J=6.2 Hz), 1.22–1.35 (1 H, m), 1.51–1.63 (2 H, m), 2.48 (1 H, dd, J=5.0, 16.5 Hz), 2.74 (1 H, dd, J=9.5, 16.5 Hz), 2.88–2.98 (1 H, m), 3.64 (3 H, s), 5.10–5.16 (2 H, m), 7.30–7.40 (5 H, m); $^{13}$C NMR (100 MHz, CDCl$_3$) δ=22.20, 22.55, 25.80, 36.57, 39.42, 41.22, 51.72, 66.46, 128.14, 128.28, 128.53, 135.74, 171.73, 175.73; LRMS calculated for C$_{16}$H$_{22}$O$_4$Na (M+Na) 301.3, found 301.0.

C. Methyl-2-Isobutyl-4-Oxo-5-Acetylthio-Pentyrate

The benzyl ester (2.28 g, 8.19 mmol) from B above was dissolved in 16 mL absolute ethanol. Palladium on carbon (Pd—C) (10%, 200 mg) was added and the reaction was stirred under hydrogen (H$_2$) (1 atm) at room temperature for 1.5 hours. Filtration through celite and evaporation yielded 1.55 g (quantitative) of the mono acid.

DMF (6 drops) was added to a solution of the above mono acid (8.1 mmol) in 20 mL of anhydrous ether, followed by slow addition of oxalyl chloride ((COCl)$_2$) (1.1 mL, 12.6 mmol, 1.5 equiv.) at room temperature. After being stirred for 1.5 hours at room temperature, the reaction was concentrated under vacuum. The resulting acid chloride (oil) was re-dissolved in acetonitrile (15 mL) and THF (15 mL), cooled to 0° C., shielded from light, treated with TMSCHN$_2$ (10.1 mL, 2.0M/hexane), and stirred at room temperature overnight. Volatiles were evaporated under vacuum. The residue was re-dissolved in ether (100 mL), washed with saturated sodium bicarbonate (40 mL×2) and brine (40 mL), dried over sodium sulfate, and concentrated to dryness to yield the crude diazoketone.

The above crude diazoketone was dissolved in 15 mL of thioacetic acid and stirred in dark at room temperature for 48 hours. Excess thioacetic acid was evaporated and the residue was column chromatographed on silica gel with 10–30% ether/petroleum ether to give 1.70 g (81% overall) of the desired acetylthioketone as a pale oil. $^1$H NMR (400 MHz, CDCl$_3$) δ=0.86 (3 H, d, J=6.3 Hz), 0.91 (3 H, d, J=6.5 Hz), 1.21–1.30 (1 H, m), 1.49–1.58 (2 H, m), 2.37 (3 H, s), 2.62 (1 H, dd, J=8.8, 22.0 Hz), 2.90–3.00 (2 H, m), 3.65 (3 H, s), 3.68 (1 H, d, J=16.3 Hz), 3.80 (1 H, d, J=16.3 Hz); $^{13}$C NMR (100 MHz, CDCl$_3$) δ=22.28, 22.44, 25.83, 30.12, 38.41, 39.00, 41.09, 43.50, 51.81, 175.98, 194.29, 202.39; LRMS calculated for C$_{12}$H$_{12}$O$_4$S (M+H) 261.3, found 261.1.

D. 2-Isobutyl-4-Oxo-5-Acetylthio-Pentanoic Acid

The above methyl ester (1.00 g, 3.84 mmol) was dissolved in 10 mL de-gassed methanol and treated with EDT (1.6 mL, 19.11 mmol, 5 equiv.) and aqueous lithium hydroxide (LiOH·H$_2$O) (1.60 g, 38 mmol, dissolved in 3 mL de-gassed water). The reaction was stirred under argon at room temperature for 2 hours. Methanol was evaporated. The resulting aqueous solution was diluted with more de-gassed water (20 mL), washed with petroleum ether (20 mL×3), acidified with 5% HCl to pH 3, and extracted with ethyl acetate (20 mL×4). The extracts were combined, dried over sodium sulfate, and concentrated to yield the crude fully de-protected thiol-acid (1.0 g) as an oil.

The above thiol (220 mg, 1.07 mmol) was dissolved in 2 mL DCM and treated with DIEA (0.37 mL, 2.14 mmol, 2 equiv.) and PNPA (194 mg, 1.07 mmol, 1 equiv.). The reaction was stirred at room temperature for 20 hours. Acidification with 1% HCl to pH 3, extraction with ethyl acetate (20 mL×3), drying over sodium sulfate, concentration under vacuum, and column chromatography on silica gel with 0–10% MeOH/CH$_2$Cl$_2$ yielded 210 mg (80%) of the desired acetylthio carboxylic acid as an oil. $^1$H NMR (400 MHz, CDCl$_3$) δ=0.90 (3 H, d, J=6.3 Hz), 0.94 (3 H, d, J=6.5 Hz), 1.27–1.37 (1 H, m), 1.55–1.70 (2 H, m), 2.40 (3 H, s), 2.60–2.71 (1 H, m), 2.88–3.10 (2 H, m), 3.70 (1 H, d, J=16.3 Hz), 3.81 (1 H, d, J=16.3 Hz); $^{13}$C NMR (100 MHz, CDCl$_3$) δ=22.15, 25.58, 29.92, 38.17, 38.69, 40.52, 42.75, 180.98, 194.35, 220.00; LRMS calculated for C$_{11}$H$_{18}$O$_4$SNa (M+Na) 269.2, found 268.9.

E. (L)-β-Cyclohexylalanine-Phenethylamide

To a solution of N-Boc-L-cyclohexylalanine (4.16 g, 15.30 mmol) in DCM (70 mL) at 0° C. was added DIEA (3.46 mL, 19.9 mmol, 1.3 equiv.), phenylethyl amine (2.02 mL, 16.09 mmol, 1.05 equiv.), HOBt (2.18 g, 16.10 mmol, 1.05 equiv.), and EDC (3.08 g, 16.10 mmol, 1.05 equiv.). The reaction was warmed to room temperature and stirred for 2 hours. DCM was evaporated and the residue was re-dissolved in 200 mL ether, washed with pH 4 phosphate buffer (0.5M, 100 mL×3), saturated sodium bicarbonate (100 mL×3), and brine (100 mL×2), dried over sodium sulfate, and concentrated under vacuum to dryness to afford the amide as an oil (4.37 g, 77%). $^1$H NMR (400 MHz, CDCl$_3$) δ=0.80–1.00 (2 H, m), 1.10–1.35 (4 H, m), 1.44 (9 H, s), 1.58–1.78 (7 H, m), 2.81 (2 H, t, J=7.2 Hz), 3.41–3.58 (2 H, m), 4.01–4.10 (1 H, m), 4.80–4.85 (1 H, br), 6.10–6.16 (1 H, br), 7.17–7.32 (5 H, m).

The above N-Boc protected amide was treated with anhydrous HCl in dioxane (4.0M, Aldrich) at room temperature for 0.5 hour. Volatiles were evaporated. The residue was re-dissolved in ethyl acetate (200 mL), washed with 0.1 N potassium hydroxide (KOH) (200 mL×2) and brine (200 mL), dried over sodium sulfate, and concentrated under vacuum to yield a pale solid as the desired amine (3.00 g, 94%). $^1$H NMR (400 MHz, CDCl$_3$) δ=0.92–1.11 (2 H, m), 1.17–1.38 (4 H, m), 1.38–1.55 (1 H, m), 1.68–1.85 (6 H, m), 2.89 (2 H, t, J=6.9 Hz), 3.41–3.49 (1 H, br), 3.52–3.63 (2 H, m); $^{13}$C NMR (100 MHz, CDCl$_3$) δ=26.10, 26.31, 26.45, 32.09, 34.14, 34.31, 35.80, 40.14, 42.73, 52.75, 126.38, 128.51, 128.74, 139.04, 175.60.

F. (2-Isobutyl-4-Oxo-5-Acetylthio-Pentanoyl)-(L)-β-Cyclohexylalanine-Phenethylamide DIEA (0.16 mL, 0.92 mmol, 1.05 equiv.) and HOBt (125 mg, 0.92 mmol, 1.05 equiv.) were sequentially added to a solution of the above acetylthio carboxylic acid (210 mg, 0.85 mmol) and the above amine in DCM (4 mL) at 0° C. A solution of EDC (176 mg, 0.92 mmol, 1.05 equiv.) in 8 mL DCM was then slowly added to the stirring reaction mixture within 2 hours. After stirring at room temperature for another 6 hours, the reaction was diluted with ethyl acetate (100 mL), washed sequentially with pH 4 phosphate buffer (0.5M, 50 mL×4) and brine (50 mL×2), dried over sodium sulfate, concentrated under vacuum, and column chromatographed on silica gel with 20–40% ethyl acetate/DCM to yield two diastereomers: A, 75 mg, as the faster-moving spot, and B, 105 mg, as the slower-moving spot on TLC developed with 40% ethyl acetate/DCM. Both isomers were white solid. Combined yield is 42%. $^1$H NMR (400 MHz, CDCl$_3$) for isomer A δ=0.86 (3 H, d, J=6.2 Hz), 0.90 (3 H, d, J=6.3 Hz), 0.80–0.98 (2 H, m), 1.10–1.32 (6 H, m), 1.45–1.58 (2 H, m), 1.60–1.78 (6 H, m), 2.38 (3 H, s), 2.60 (1 H, dd, J=3.6, 18.0 Hz), 2.66–2.86 (3 H, m), 2.96 (1 H, dd, J=9.6, 18.0 Hz), 3.38–3.59 (2 H, m), 3.63 (1 H, d, J=16.3 Hz), 3.78 (1 H, d, J=16.3 Hz), 4.32 (1 H, ddd, J=6.0, 8.4, 8.4 Hz), 6.03 (1 H, br d, J=80 Hz), 6.18 (1 H, br t, J=5.7 Hz), 7.15–7.32 (5 H, m); LRMS calculated for C$_{28}$H$_{42}$O$_4$N$_2$SNa (M+Na) 525.7, found 525.3.

$^1$H NMR (400 MHz, CDCl$_3$) for isomer B δ=0.90 (3 H, d, J=6.5 Hz), 0.93 (3 H, d, J=6.3 Hz), 0.82–1.30 (5 H, m), 1.43 (1 H, d, J=4.4, 11.1, 14.3 Hz), 1.48–1.76 (9 H, m), 1.91 (1 H, ddd, J=4.4, 9.9, 14.3 Hz), 2.33 (3 H, s), 2.56–2.65 (1 H, m), 2.66 (1 H, dd, J=3.0, 18.4 Hz), 2.83 (2 H, t, J=7.5 Hz), 3.01 (1 H, dd, J=10.5, 18.4 Hz), 3.45 (1 H, dt, J=2.1, 7.5 Hz), 3.46 (1 H, dt, J=2.2, 7.4 Hz), 3.53 (1 H, d, J=16.5 Hz), 3.78 (1 H, d, J=16.5 Hz), 4.46 (1 H, ddd, J=4.2, 8.5, 11.0 Hz), 5.83 (1 H, br d, J=8.5 Hz), 6.87 (1 H, br t, J=5.4 Hz), 7.15–7.30 (5 H, m); $^{13}$C NMR (100 MHz, CDCl$_3$) δ=21.94, 23.24, 25.54, 25.99, 26.35, 26.42, 30.06, 31.63, 33.98, 34.30, 35.35, 38.76, 38.89, 40.26, 40.95, 41.57, 45.01, 51.03, 126.18, 128.36, 128.82, 139.24, 171.94, 174.67, 194.39, 204.68; LRMS calculated for C$_{28}$H$_{42}$O$_4$N$_2$SNa (M+Na) 525.7, found 525.3.

G. [(S)-2-Isobutyl-4-Oxo-5-Mercapto-Pentanoyl]-(L)-β-Cyclohexylalanine-Phenethylamide The above acetylthioketone (53 mg, 0.11 mmol) was dissolved in 15 mL of degassed dioxane. EDT (1 mL, 100 equiv.) was added, followed by addition of 0.1N NaOH aqueous solution (5.0 mL, 0.5 mmol, 5 equiv.). The reaction was stirred under argon at room temperature for 2 hours. The reaction was quenched with dilute HCl (0.5%, 5 mL, degassed) and extracted with DCM (20 mL×4, degassed). The extracts were combined, dried over sodium sulfate, concentrated under vacuum, and column chromatographed under argon on silica gel with 0–35% ethyl acetate/DCM (degassed) to yield 34 mg (70%) of the desired free thiol as a white solid. Positive Ellman test clearly showed the presence of free thiol on the molecule. m.p. 144°–145° C.; $^1$H NMR (400 MHz, CDCl$_3$) δ=0.91 (3 H, d, J=6.4 Hz), 0.95 (3 H, d, J=6.5 Hz), 0.85–1.35 (7 H, m), 1.45 (1 H, ddd, J=4.6, 10.9, 15.4 Hz), 1.50–1.78 (6 H, m), 1.81 (1 H, t, J=7.6 Hz), 1.92 (1 H, ddd, J=4.3, 9.6, 14.2 Hz), 2.57–2.64 (1 H, m), 2.69 (1 H, dd, J=3.3, 18.6 Hz), 2.85 (2 H, t, J=7.3 Hz), 3.02 (1 H, dd, J=10.5, 18.6 Hz), 3.29 (2 H, d, J=7.9 Hz), 3.49 (2 H, dt, J=5.9, 7.3 Hz), 4.47 (1 H, ddd, J=4.4, 8.7, 13.2 Hz), 5.72 (1 H, br d, J=8.7 Hz), 6.79 (1 H, br t, J=5.4 Hz), 7.18–7.31 (5 H, m); $^{13}$C NMR (100 MHz, CDCl$_3$) δ=22.05, 23.19, 25.62, 26.03, 26.39, 26.43, 31.77, 33.99, 34.20, 34.38, 35.53, 38.94, 40.43, 40.99, 41.61, 44.16, 51.11, 126.25, 128.44, 128.88, 139.20, 171.87, 174.68, 206.21; LRMS calculated for C$_{28}$H$_{40}$O$_3$N$_2$Na (M+Na) 483.6, found 483.2.

H. [(R)-2-Isobutyl-4-Oxo-5-Mercapto-Pentanoyl]-(L)-β-Cyclohexylalanine-Phenethylamide The acetylthio-ketone isomer A (20 mg) was treated with the same conditions as above to yield the free-thiol as a white solid (10 mg, 55%). This mercapto-ketone appears to easily equilibrate with the corresponding enol. A relatively pure fraction of the ketone form was separated from the enol by column chromatography on silica gel and a proton NMR was quickly taken. $^1$H NMR (400 MHz, CDCl$_3$) δ=0.88 (3 H, d, J=6.3 Hz), 0.91 (3 H, d, J=6.3 Hz), 0.8–2.0 (22 H, m), 2.62 (1 H, dd, J=3.7, 17.9 Hz), 2.6–2.9 (3 H, m), 2.99 (1 H, dd, J=9.7, 17.9 Hz), 3.33 (1 H, d, J=7.7 Hz), 3.4–3.7 (3 H, m), 4.32 (1 H, m), 5.97 (1 H, br d, J=8.1 Hz), 6.06 (1 H, br t, J=5.5 Hz), 7.1–7.3 (5 H, m); LRMS calculated for $C_{26}H_{40}O_3N_2SNa$ (M+Na) 483.6, found 483.2.

Example 2

Experimental Procedure for the Synthesis of 2-Isobutyl-4- -Mercapto-Butanoyl-(L)-β-Cyclohexylalanine-Phenethylamide.

Figure 2:
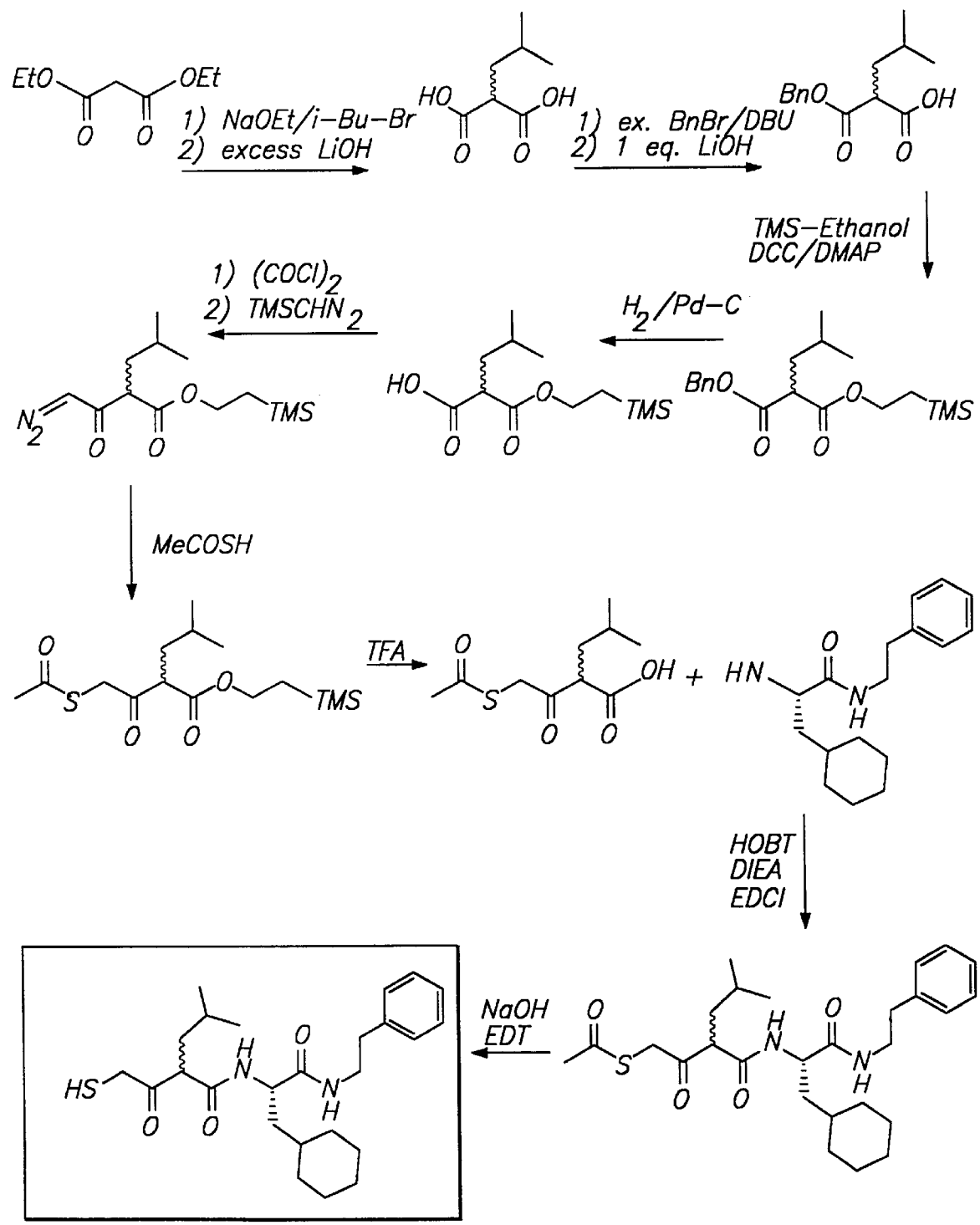

The synthesis of the title compound is illustrated in the attached FIG. 2.

A. Isobutylmalonic Acid

Diethyl malonate (10.00 g, 62.40 mmol) was added to a solution of sodium ethoxide (NaOEt) in anhydrous ethanol (EtOH) (68.7 mmol, 120 mL, 1.1 equiv.) and stirred for 20 minutes at room temperature. Isobutyl bromide (7.20 mL, 66.20 mmol, 1.06 equiv.) was then added, and the reaction was refluxed overnight. Ethanol was evaporated, and ether (100 mL) was added to the residue. The mixture was washed with 5% HCl (50 mL×1), water, (50 mL×2), and brine (50 mL×1), dried over sodium sulfate, and concentrated to yield crude ester (12.20 g, 90%). $R_f$=0.8 (20% ether/petroleum ether). A portion of this ester (11.10 g, 51.3 mmol) was then hydrolyzed with LiOH (22.0 g, 524 mmol, 10 equiv.) in aqueous methanol (methanol, 75 mL; water, 25 mL) overnight at room temperature. After aqueous work-up, the reaction yielded 8.15 g (quantitative) of the desired di-acid. $^1$H NMR (400 MHz, CDCl$_3$) δ=0.93 (6 H, d, J=6.6 Hz), 1.59–1.70 (1 H, m), 1.81 (2 H, m), 3.46 (1 H, t, J=7.6 Hz), 5.10 (2 H, br s). $^{13}$C NMR (100 MHz, CDCl$_3$) δ=22.13, 26.08, 37.70, 49.69, 173.34.

B. Benzyl Isobutylmalonic Mono-Ester

The above di-acid (4.00 g, 25.00 mmol) was dissolved in 50 mL acetonitrile and treated with benzyl bromide (6.00 mL, 50.00 mmol, 2.0 equiv.) and DBU (9.50 mL, 63.5 mmol, 2.4 equiv.) for 60 hours at room temperature. The reaction was acidified to pH 3 with concentrated HCl. Acetonitrile was evaporated under vacuum. The residue was taken into ether (200 mL), and washed with water (100 mL×2) and brine (100 mL×1), dried over sodium sulfate, and concentrated to yield an oil (7.2 g). This oil was dissolved in 40 mL THF. Aqueous KOH (2.20 g, 39.3 mmol, 2.0 equiv., in 20 mL water) was slowly added at room temperature within 1 hour. The reaction was stirred 24 hours and concentrated under vacuum. The residue was taken into water (50 mL), washed with 30% ether/petroleum ether (50 mL×3), acidified with 10% HCl to pH 3, extracted with ethyl acetate (EtOAc) (50 mL×4). The extracts were combined, dried over magnesium sulfate (MgSO$_4$), and concentrated to yield 5.10 g of the desired product (82%). $R_f$=0.2 (20% ether/petroleum), which was used in the next reaction without further purification.

C. Benzyl-(2-Trimethylsilylethyl)-Isobutylmalonic Ester

The above mono-ester (5.10 g, 20.40 mmol) was dissolved in 40 mL acetonitrile and cooled to 0° C. 2-Trimethylsilylethanol (3.10 mL, 21.60 mmol, 1.06 equiv.), pyridine (1.80 mL, 22.20 mmol, 1.1 equiv.), and DCC (4.60 g, 22.30 m mol, 1.1 equiv.) were added sequentially. The reaction was stirred for 2 hours at room temperature and concentrated under vacuum. The residue was taken into ether (200 mL) and the white precipitate was filtered. The clear filtrate was then washed with 0.5% HCl (50 mL×2) and brine (50 mL×1), dried over MgSO$_4$, purified by flash column chromatography on silica gel with 5% ether/petroleum ether to yield 6.20 g desired product (87%). $R_f$=0.3 (5% ether/petroleum ether). $^1$H NMR (400 MHz, CDCl$_3$) δ=0.02 (9 H, s), 0.90 (8 H, m), 1.50–1.60 (1 H, m), 1.79–1.83 (2 H, m), 3.46 (1 H, t, J=7.7 Hz), 4.15–4.22 (2 H, m), 5.16 (1 H, d, J=12.3 Hz), 5.20 (1 H, d, J=12.3 Hz), 7.30–7.37 (5 H, m). $^{13}$C NMR (100 MHz, CDCl$_3$) δ=17.16, 22.21, 26.09, 37.48, 50.41, 63.72, 66.87, 128.16, 128.26, 128.48, 135.55, 169.58, 169.63.

D. (2-Trimethylsilylethyl)-Isobutylmalonic Mono-Ester

The above benzyl ester (6.13 g, 17.50 mmol) was hydrogenated with H$_2$ (balloon) in the presence of 10% Pd—C (600 mg, 10% wt) in ethanol at room temperature (2 hours). Filtration and evaporation yielded 4.10 g (90%) of pure product. $R_f$=0.1 (10% ether/petroleum ether). $^1$H NMR (400 MHz, CDCl$_3$) δ=−0.04 (9 H, s), 0.84 (6 H, d, J=6.6 Hz), 0.89–0.95 (2 H, m), 1.43–1.58 (1 H, m), 1.65–1.78 (2 H, m), 3.35 (1 H, t, J=7.6 Hz), 4.12–4.18 (2 H, m). $^{13}$C NMR (100 MHz, CDCl$_3$) δ=17.15, 22.15, 26.08, 37.64, 50.13, 64.00, 169.84, 174.39.

E. (2-Trimethylsilylethyl) 2-Isobutyl-4-Acetylthiol-3-oxo-Butyrate

The above mono ester (1.49 g, 5.70 mmol) was treated with oxalyl chloride (1.00 mL, 11.50 mmol, 2 equiv.) and DMF (5 drops) in benzene at room temperature. After 2 hours, the reaction was concentrated under vacuum to give the corresponding acid chloride as an oil. The acid chloride was dissolved in 30 mL anhydrous THF and treated with TMS-CHN$_2$ (6.30 mL, 2.0M/hexane, 12.60 mmol, 2.2 equiv.) at room temperature for 20 hours in the dark. THF was evaporated and the residue was dissolved in ether (200 mL), washed with saturated sodium bicarbonate (50 mL×2) and brine (50 mL×1), dried over MgSO$_4$, and concentrated to yield the crude diazoketone as a yellow oil (1.72 g). The diazoketone was then treated with thioacetic acid (MeCOSH) (10 mL) under argon at room temperature for 70 hours in the dark. Volatiles were evaporated and the residue was purified by flash column chromatography on silica gel with 20% ether/petroleum ether, yielding 300 mg (16%—3 steps from the mono-ester) pure desired product. $R_f$=0.4 (50% ether/petroleum ether). $^1$H NMR (400 MHz, CDCl$_3$) δ=0.04 (9 H, s) 0.91 (3 H, d, J=6.6 Hz), 0.92 (3 H, d, J=6.6 Hz), 0.98–1.03 (2 H, m), 1.49–1.60 (1 H, m), 1.72–1.84 (2 H, m), 2.38 (3 H, s), 3.70 (1 H, t, J=7.3 Hz), 3.86 (1 H, d, J =16.7 Hz), 3.93 (1 H, d, J=16.7 Hz), 4.19–4.26 (2 H, m). $^{13}$C NMR (100 MHz, CDCl$_3$) δ=18.84, 23.81, 23.91, 27.65, 31.64, 38.54, 40.13, 57.99, 65.57, 171.13, 195.52, 200.37.

F. 2-Isobutyl-4-Acetylthiol-3-oxo-Butyric Acid

The above 2-trimethylsilylethyl ester (300 mg, 0.90 mmol) was treated with 50% TFA/DCM (3 mL) at room temperature for 30 minutes. Evaporation and purification by flash column chromatography on silica gel with DCM-EtOAc yielded 210 mg (quantitative) of the pure acid. $R_f$=0.1 (60% ether/petroleum ether). $^1$H NMR (400 MHz, CDCl$_3$) δ=0.93 (3 H, d, J=6.6 Hz), 0.94 (3 H, d, J=6.6 Hz), 1.56–1.65 (1 H, m), 1.81 (2 H, t, J=1.81 Hz), 2.39 (3 H, s), 3.75–3.82 (1 H, m), 3.90 (1 H, d, J=16.7 Hz), 4.00 (1 H, d, J=16.7 Hz). $^{13}$C NMR (100 MHz, CDCl$_3$) δ=22.28, 26.09, 30.06, 37.05, 38.74, 55.71, 174.72, 194.23, 198.59.

G. 2-Isobutyl-4-Acetylthiol-Butanoyl-(L)-β-Cyclohexylalanine-Phenethylamide The above carboxylic acid (11 mg, 0.047 mmol) was dissolved in 1 mL DCM and cooled to 0° C.

Cyclohexylalanine-phenethylamide (14 mg, 0.051 mmol, 1.05 equiv.), DIEA (9 µL, 0.051 mmol, 1.05 equiv.), HOBt (7 mg, 0.051 mmol, 1.05 equiv.), and EDCI (10 mg, 0.051 mmol, 1.05 equiv.) were added sequentially. The reaction was then stirred at room temperature for 5 hours, diluted with EtOAc (50 mL), washed with pH 4 phosphate buffer (0.5 M, 30 mL×2) and brine (30 mL×3), dried over sodium sulfate, concentrated under vacuum, and purified by flash column chromatography on silica gel with 0–20% EtOAc/DCM to yield 6 mg (26%) of the desired di-peptide. $R_f$=0.8 (40% EtOAc/DCM). $^1$H NMR (400 MHz, CDCl$_3$) δ=0.92 (3 H, d, J=6.6 Hz), 0.93 (3 H, d, J=6.6 Hz), 1.20–1.80 (16 H, m), 2.38 (3 H, s), 2.77–2.83 (2 H, m), 3.40–3.71 (3 H, m), 3.72–3.90 (2 H, m), 4.15–4.41 (1 H, m), 6.18–6.38 (2 H, m), 7.15–7.30 (5 H, m).

H. 2-Isobutyl-4-Mercapto-Butanoyl-(L)-β-Cyclohexylalanine-Phenethylamide

The above thioacetate (3.0 mg, 0.0061 mmol) was treated with 0.1N NaOH (0.12 mL, 0.012 mmol, 2 equiv.) in degassed dioxane (1 mL) in the presence of EDT (50 µL, 0.6 mmol, 100 equiv.) under argon at room temperature for 2 hours. The reaction was acidified with 0.5% HCl to pH 3 and extracted with DCM (10 mL×5). The extracts were combined, dried over MgSO$_4$, and concentrated under vacuum to dryness. The residue was then triturated with degassed petroleum ether (5 mL×5, until no apparent thiol smell) and lyophilized from benzene to give 2.5 mg (92%) of the title compound as a white solid. $R_f$=0.6 (40% ether/petroleum ether). $^1$H NMR (400 MHz, CDCl$_3$) δ=0.92 (3 H, d, J=6.5 Hz), 0.93 (3 H, d, J=6.6 Hz), 1.21–1.95 (16 H, m), 2.88–2.94 (2 H, m), 3.42–3.84 (5 H, m), 4.15–4.40 (1 H, m), 5.95–6.04 (1 H, m), 6.28–6.38 (1 H, m), 7.15–7.34 (5 H, m). LRMS calculated for $C_{25}H_{38}N_2O_3S$ (M +H) 469.6, found 469.2.

Example 3

Figure 3:
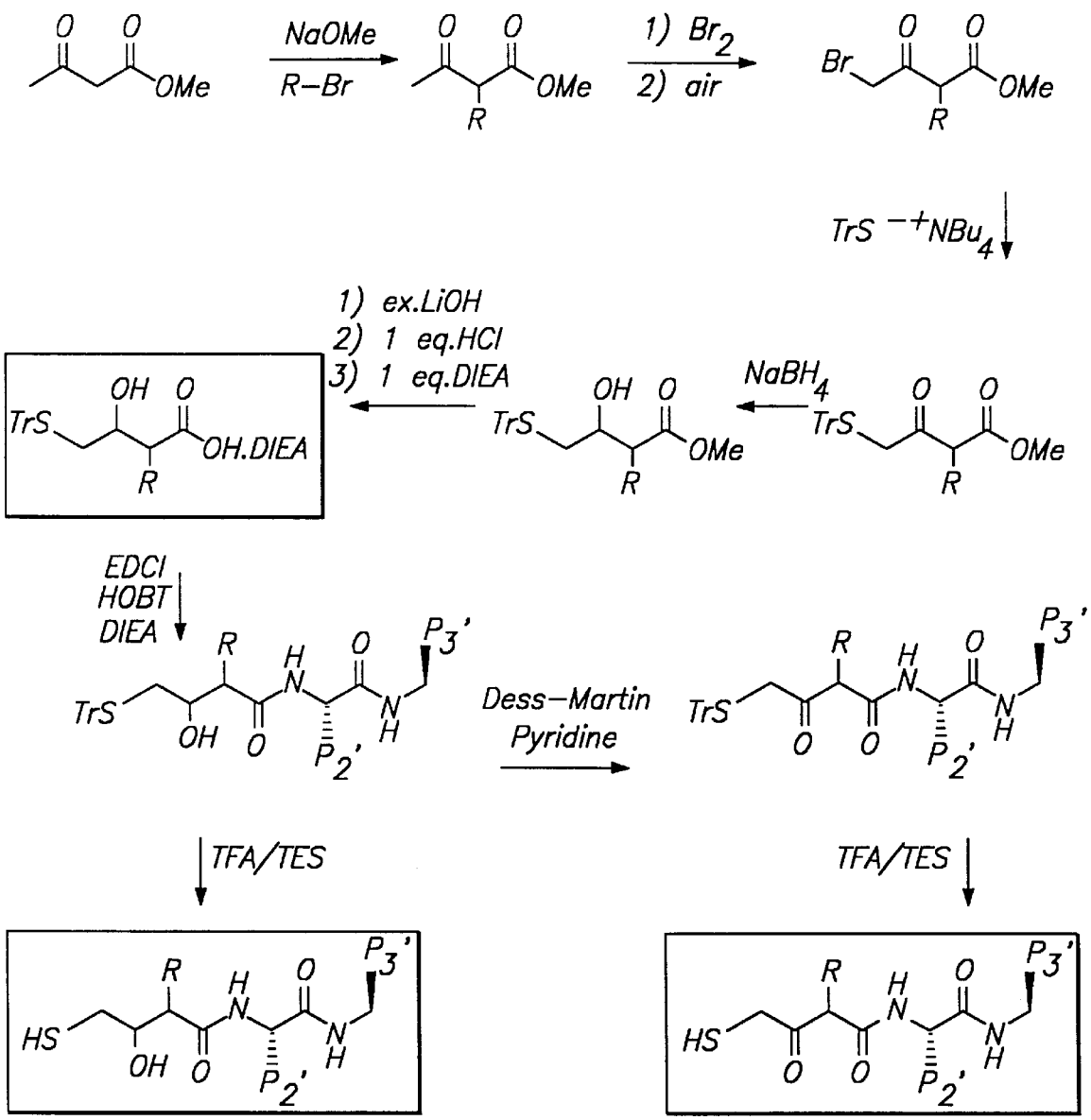

Synthesis of 2-n-Heptyl-3-Hydroxy-4-Mercapto-Butanoyl(L)-Leu-(L)-Leu-Ethylamide and 2-n-Heptyl-3-Oxy-4-Mercapto-Butanoyl-(L)-Leu-(L)-Leu-Ethylamide The synthesis of the title compound is illustrated in the attached FIG. 3.

A. Methyl-2-n-Heptyl Acetoacetate (a, R=n-heptyl)

Methyl acetoacetate (20.00 g, 172.2 mmol) was treated with sodium methoxide (NaOMe)/MeOH (freshly prepared by dissolving 4.00 g sodium in 200 mL anhydrous MeOH at 0° C.) at room temperature for 20 minutes. n-Heptyl bromide (24.60 mL, 156.6 mmol, 0.9 equiv.) was added and the solution was refluxed for 24 hours. Methanol was evaporated and the residue was treated with 5% hydrogen sulfate (H$_2$SO$_4$) (100 mL) in acetone (200 mL) at room temperature for 2 hours. Acetone was evaporated and the aqueous layer was extracted with ether (400 mL). The ether extract was then quickly washed with 1N NaOH (100 mL×3), water (100 mL×2), and brine (100 mL×1), and dried over MgSO$_4$. Evaporation of the solvents yielded 33.56 g (78%) crude product as an oil. $R_f$=0.6 (10% ether/petroleum ether). $^1$H NMR (400 MHz, CDCl$_3$) δ 0.88 (3 H, t, J=6.7 Hz), 1.20–1.45 (10 H, br m), 1.78–1.91 (2 H, m), 2.22 (3 H, s), 3.42 (1 H, t, J=7.4 Hz), 3.73 (3 H, s).

B. Methyl-2-n-Heptyl-4-Bromo Acetoacetate (b, R=n-heptyl)

A solution of bromine (18.56 g, 116.15 mmol, 0.95 equiv.) in 50 mL chloroform was slowly added, via an addition funnel, to a solution of the above acetoacetate a (26.14 g, 121.96 mmol) in 125 mL chloroform at 0° C. within a period of 8 hours. The reaction was stirred another 1 hour after addition of bromine. Two drops of water were then added and air was bubbled into the solution at room temperature for 2 hours. The reaction was diluted with 500 mL ether, washed with water (125 mL×2) and brine (125 mL×1), dried over MgSO$_4$, and evaporated to give a yellow oil as crude product (34.18 g, 95%). $R_f$=0.4 (10% ether/petroleum ether).

C. Methyl-2-n-Heptyl-4-Tritylthio Acetoacetate (c, R=n-heptyl)

A solution of the above acetoacetate b (3.66 g, 12.44 mmol) in toluene (30 mL, degassed) was treated with TS$^{-+}$NBu$_4$ (18.66 mmol, 1.5 equiv. freshly prepared from triphenylmethyl mercaptan (trityl-SH) and tetrabutylammonium hydroxide (Bu$_4$NOH) in 75 mL degassed toluene), in accordance with the procedure set forth in Blanc-Muesser et al, U.C.S., Perkin I, 15 (1982), at room temperature for 3 hours. Toluene was evaporated and ether (400 mL) was added to the residue. This solution was then washed with water (200 mL×3) and brine (200 mL×1), dried over MgSO$_4$, concentrated under vacuum, and column chromatographed on silica gel with 5–10% ether/petroleum ether to yield 1.98 g (33%, overall) of pure product as an oil, $R_f$=0.35 (10% ether/petroleum ether). $^1$H NMR (400 MHz, CDCl$_3$) δ=0.87 (3 H, t, J=6.8 Hz), 1.10–1.30 (10 H, m), 1.55–1.90 (2 H, m), 3.19 (2 H, s), 3.29 (1 H, t, J=7.0 Hz), 3.61 (3 H, s), 7.20–7.49 (15 H, m).

D. Methyl-2-n-Heptyl-3-Hydroxy-4-Tritylthio Butyrate (d, R=n-heptyl)

Ketone c (1.981 g, 4.049 mmol) was dissolved in 25 mL anhydrous methanol and treated with sodium borohydride (NaBH$_4$) (0.170 g, 4.490 mmol, 1.1 equiv.) at 0° C. for 30 minutes. The reaction was then diluted with ether (200 mL), washed with brine (300 mL×1, 50 mL×20), dried over MgSO$_4$, and concentrated to yield 2.25 g of crude product, which consisted of about a 1:1 ratio of the racemic threo and erythro isomers. The two pairs of isomers were separated by silica gel column chromatography with 10% ether/petroleum ether. Pair d$_A$: $R_f$=0.6 (30% ether/petroleum ether); $^1$H NMR (400 MHz, CDCl$_3$) δ=0.96 (3 H, t, J=6.8 Hz), 1.15–1.75 (12 H, m), 2.38 (1 H, dd, J=4.5, 12.9 Hz), 2.45–2.51 (1 H, m), 2.59 (1 H, dd, J=8.4, 12.9 Hz), 3.47–3.55 (1 H, m), 3.68 (3 H, s), 7.24–7.52 (15 H, m). Pair d$_B$: $R_f$=0.5 (30% ether/petroleum ether); $^1$H NMR (400 MHz, CDCl$_3$) δ=0.88 (3 H, t, J=6.9 Hz), 1.10–1.70 (12 H, m), 2.32–2.49 (3 H, m), 3.28–3.34 (1 H, m), 3.63 (3 H, s), 7.19–7.46 (15 H, m).

E. 2-n-Heptyl-3- Hydroxy-4-Tritylthio-Butyric Acid, DIEA Salt (e, R=n-heptyl)

Hydroxy ester d$_B$ (1.98 g, 4.30 mmol) was dissolved in 40 mL methanol and treated with aqueous LiOH (1.69 g, 40.3 mmol, 10 equiv., in 15 mL water) at room temperature overnight. The methanol was evaporated and more water (400 mL) was added to the residue. The resulting white suspension was washed with 20% ether/petroleum ether (200 mL×2), slowly acidified with 0.5% HCl to pH 4, and extracted with EtOAc (80 mL×4). The extracts were combined, dried over MgSO$_4$, and concentrated under vacuum. The resulting oil was redissolved in DCM and treated with 1 equivalent of DIEA. Evaporation of the solvent and lyophilization from benzene yielded a white foam (1.97 g, quantitative). e$_B$: $R_f$=0.5 (10% MeOH/DCM/ trace HOAc). $^1$H NMR (400 MHz, CDCl$_3$) δ=0.95 (3 H, t, J=6.8 Hz), 1.24–1.70 (15 H, m), 1.40 (6 H, d, J=6.7 Hz), 2.20–2.24 (1 H, m), 2.41 (1 H, dd, J=5.4, 12.4 Hz), 2.54 (1 H, dd, J=7.7, 12.4 Hz), 3.08 (2 H, q, J=7.4 Hz), 3.40–3.43 (1 H, m), 3.67 (2 H, h, J=6.7 Hz), 7.20–7.52 (15 H, m).

F. 2-n-Heptyl-3-Hydroxy-4-Tritylthio-Butanoyl-(L)-Leu-(L)-Leu-Ethylamide (f, R=n-heptyl, P$_2$–P$_3$=Leu-Leu-Ethyl)

DIEA salt e$_B$ (80 mg, 0.13 mmol) was dissolved in 4 mL DCM. Leu-Leu NHEtHCl salt (46 mg, 0.15 mmol, 1.1 equiv.), DIEA (28 μL, 0.16 mmol, 1.2 equiv.), HOBt (20 mg, 0.15 mmol, 1.1 equiv.), and EDCI (28 mg, 0.15 mmol, 1.1 equiv.) were added sequentially at room temperature. The reaction was stirred at room temperature for 14 hours, diluted with EtOAc (100 mL), washed with phosphate buffer (pH 4, 0.5M, 30 mL×3), saturated sodium bicarbonate (30 mL×3) and brine (30 mL×1), dried over MgSO$_4$, concentrated under vacuum to yield 90 mg crude peptide (93%). f$_B$: R$_f$=0.55 (40% EtOAc/DCM). $^1$H NMR (400 MHz, CDCl$_3$) δ=0.92–1.05 (15 H, m), 1.15–1.90 (21 H, m), 2.64 (1 H, dd, J=8.0, 13.2 Hz), 2.86 (1 H, dd, J=5.8, 13.2 Hz), 3.06–3.12 (1 H, m), 3.26–3.38 (2 H, m), 3.67–3.74 (1 H, m), 4.35–4.52 (2 H, m), 5.90–6.70 (3 H, several m's), 7.38–7.52 (15 H, m).

H. 2-n-Heptyl-3-Hydroxy-4-Mercapto-Butanoyl-(L)-Leu-(L)-Leu-Ethylamide (h, R=n-heptyl, P$_2$–P$_3$=Leu-Leu-Ethyl)

Trityl mercapto ether f$_B$ (50 mg, 0.068 mmol) was dissolved in degassed DCM (4 mL). TES (55 μL, 0.34 mmol, 5 equiv.) and TFA (1 mL) were added sequentially at room temperature. The reaction was stirred at room temperature for 30 minutes. Volatiles were evaporated and the residue was purified by flash column chromatography on silica gel with 5–10% EtOAc/DCM (degassed) under argon pressure, yielding 26 mg of pure product as a white solid (78%). H$_B$: R$_f$=0.3 (10% EtOAc/DCM). $^1$H NMR (400 MHz, CDCl$_3$) δ=0.90–1.08 (15 H, m), 1.21 (3 H, t, J=7.2 Hz), 1.26–1.90 (18 H, m), 2.50–2.78 (2 H, m), 2.90–3.00 (1 H, m), 3.28–3.42 (2 H, m), 3.78–3.97 (1 H, m), 4.40–4.57 (2 H, m), 6.52–7.62 (3 H, several m's). LRMS calculated for C$_{25}$H$_{49}$N$_3$O$_4$S (M–H) 486.7, found 486.5.

G. 2-n-Heptyl-3-Oxo-Tritylthio-Butanoyl-(L)-Leu-(L)-Leu-Ethylamide (g, R =n-heptyl, P$_2$–P$_3$=Leu-Leu-Ethyl)

Alcohol h$_B$ (45 mg, 0.061 mmol, crude) and pyridine (20 μL, 0.25 mmol, 4 equiv.) were dissolved in 3 mL DCM. Dess-Martin reagent (53 mg, 0.12 mmol, 2 equiv.) was quickly added to the solution at room temperature. The initially clear solution was stirred 1 hour at room temperature and it became milky. The reaction was diluted with EtOAc (30 mL), vigorously stirred with 25% sodium thiosulfate (Na$_2$S$_2$O$_3$)/saturated sodium bicarbonate (NaHCO$_3$) (5 mL) at room temperature for 20 minutes, washed with saturated NaHCO$_3$ (20 mL×2) and brine (20 mL×1), dried over MgSO$_4$, concentrated under vacuum, yielding 44 mg crude product with reasonable purity, although this crude product was further purified by preparative TLC (0.5 mm silica gel, 40% EtOAc/DCM, degassed) before the critical final deprotection. g$_B$: R$_f$=0.6 (40% EtOAc/DCM). $^1$H NMR (400 MHz, CDCl$_3$) δ=0.80–1.08 (15 H, m), 1.13–1.90 (21 H, m), 2.95–3.01 (1 H, m), 3.20–3.31 (4 H, m), 4.29–4.50 (2 H, m), 6.08–6.70 (3H, several m's), 7.25–7.60 (15 H, m).

I. 2-n-Heptyl-3-Oxo-4-Mercapto-Butanoyl-(L)-Leu-(L)-Leu-Ethylamide (i, R=n-heptyl, P$_2$–P$_3$=Leu-Leu-Ethyl)

Tritylmercapto ether g$_B$ (6 mg, 0.0082 mmol) was dissolved in 1 mL degassed DCM and treated with TES (7 μL, 0.044 mmol, 5 equiv.) and TFA (0.25 mL) under argon at room temperature for 30 minutes. Volatiles were evaporated, and the residue was purified by silica gel column chromatography with 20–40% EtOAc/DCM (degassed) under argon pressure, yielding 3 mg (76%) of pure product as a white solid. I$_B$: R$_f$=0.25 (40% EtOAc/DCM). $^1$H NMR (400 MHz, CDCl$_3$) δ=0.93–1.08 (15 H, m), 1.18–1.25 (3 H, m), 1.28–2.00 (18 H, m), 3.30–3.40 (2 H, m), 3.53–3.59 (1 H, m), 3.70–3.77 (1 H, m), 4.40–4.50 (2 H, m), 6.05–6.68 (3 H, several m's). LRMS calculated for C$_{25}$H$_{47}$N$_3$O$_4$S (M+H) 486.7, found 486.2.

Example 4

Other Analogs With a General Structure of h or i Were Synthesized Following the Examples Above The characterization data obtained for such compounds were as follows:

A. 2-n-Heptyl-3-Hydroxy-4-Tritylthio-Butyric Acid, DIEA Salt (e, R=n-heptyl)

e$_A$: R$_f$=0.5 (10% MeOH/DCM/trace HOAc). Product was confirmed by $^1$H NMR (400 MHz, CDCl$_3$).

B. 2-n-Heptyl-3-Hydroxy-4-Tritylthio-Butanoyl-(L)-Leu-(L)-Leu-Ethylamide (f, R=n-heptyl, P$_2$–P$_3$=Leu-Leu-Ethyl)

f$_A$: R$_f$=0.6 (40% EtOAc/DCM/trace HOAc). Product was confirmed by $^1$H NMR (400 MHz, CDCl$_3$).

C. 2-n-Heptyl-3-Hydroxy-4-Mercapto-Butanoyl-(L)-Leu-(L)-Leu-Ethylamide (h, R=n-heptyl, P$_2$–P$_3$=Leu-Leu-Ethyl)

H$_A$: R$_f$=0.2 (40% EtOAc/DCM). Product was confirmed by $^1$H NMR (400 MHz, CDCl$_3$). LRMS calculated for C$_{25}$H$_{49}$N$_3$O$_4$S (M+H) 488.7, found 488.3.

D. 2-n-Heptyl-3-Hydroxy-4-Tritylthio-Butanoyl-(L)-β-Cyclohexylalanine-Phenethylamide (f, R=n-heptyl, P$_2$–P$_3$=Cyclohexylala-Phenethyl f$_A$: R$_f$=0.8 (20% EtOAc/DCM/trace HOAc). $^1$H NMR (400 MHz, CDCl$_3$). Two diastereomers (1 and 2) were separated in reaction of pair B. f$_{B1}$: R$_f$=0.7 (20% EtOAc/DCM/trace HOAc). $^1$H NMR (400 MHz, CDCl$_3$). f$_{B2}$: R$_f$=0.5 (20% EtOAc/DCM/trace HOAc). Product was confirmed by $^1$H NMR (400 MHz, CDCl$_3$).

E. 2-n-Heptyl-3-Hydroxy-4-Mercapto-Butanoyl-(L)-β-Cyclohexylalanine-Phenethylamide (h, R=n-heptyl, P$_2$–P$_3$=Cyclohexylala-Phenethyl H$_A$: R$_f$=0.2 (10% EtOAc/DCM). $^1$H NMR (400 MHz, CDCl$_3$). LRMS calculated for C$_{28}$H$_{46}$N$_2$O$_3$S (M+H) 491.7, found 491.2. R$_f$=0.2 (10% EtOAc/DCM). $^1$H NMR (400 MHz, CDCl$_3$). LRMS calculated for C$_{28}$H$_{46}$N$_2$O$_3$S (M+H) 491.7, found 491.2. R$_f$=0.2 (20% EtOAc/DCM). Product was confirmed by $^1$H NMR (400 MHz, CDCl$_3$). LRMS calculated for C$_{28}$H$_{46}$N$_2$O$_3$S (M+H) 491.7 found 491.3.

F. 2-n-Heptyl-3-Oxo-4-Tritylthio-Butanoyl-(L)-β-Cyclohexylalanine-Phenethylamide (g, R=n-heptyl, P$_2$–P$_3$=Cyclohexylala-Phenethyl)

From f$_A$: R$_f$=0.7 (10% EtOAc/DCM). Product was confirmed by $^1$H NMR (400 MHz, CDCl$_3$).

G. 2-n-Heptyl-3-Oxo-4-Mercapto-Butanoyl-(L)-β-Cyclohexylalanine-Phenethylamide (i, R=n-heptyl, P$_2$–P$_3$=Cyclohexylala-Phenethyl R$_f$=0.3 (10% EtOAc/DCM). Product was confirmed by $^1$H NMR (400 MHz, CDCl$_3$). LRMS calculated for C$_{28}$H$_{44}$N$_2$O$_3$S (M+H) 489.7 found 489.3.

H. Methyl-2-(3-Phenylpropyl) Acetoacetate (a, R=3-phenylpropyl).

$R_f$=0.3 (20% ether/petroleum ether). Product was confirmed by $^1$H NMR (400 MHz, CDCl$_3$).

I. Methyl-2-(3-Phenylpropyl)-4-Bromo Acetoacetate (b, R=3-phenylpropyl)

$R_f$=0.4 (20% ether/petroleum ether).

J. Methyl-2-(3-Phenylpropyl)-4-Tritylthio Acetoacetate (c, R=3-phenylpropyl)

$R_f$=0.3 (10% ether/petroleum ether). Product was confirmed by $^1$H NMR (400 MHz, CDCl$_3$).

I. Methyl-2-(3-Phenylpropyl)-3-Hydroxy-4-Tritylthio Butyrate (d, R=3-phenylpropyl)

$d_A$: $R_f$=0.2 (20% ether/petroleum ether). $^1$H NMR (400 MHz, CDCl$_3$)
$d_B$: $R_f$=0.1 (20% ether/petroleum ether). Product was confirmed by $^1$H NMR (400 MHz, CDCl$_3$).

J. 2-(3-Phenylpropyl)-3-Hydroxy-4-Tritylthio Butyric Acid, DIEA salt (e, R=3-phenylpropyl)

$e_A$: $R_f$=0.6 (10% MeOH/DCM/trace HOAC). $E_B$: $R_f$=0.6 (10% MeOH/DCM/trace HOAc). Products were confirmed by $^1$H NMR (400 MHz, CDCl$_3$).

K. 2-(3-Phenylpropyl)-3-Hydroxy-4-Tritylthio-Butanoyl-(L)-Leu-(L)Leu-Ethylamide (f, R=3-phenylpropyl, P$_2$–P$_3$=Leu-Leu-Ethyl)

$f_A$: $R_f$=0.4 (40% EtOAc/DCM/trace HOAc). $f_B$: $R_f$=0.4 (40% EtOAc/DCM/trace HOAc). Products were confirmed by $^1$H NMR (400 MHz CDCl$_3$).

L. 2-(3-Phenylpropyl)-3-Hydroxy-4-Mercapto-Butanoyl-(L)-Leu-(L)Leu-Ethylamide (h, R=3-phenylpropyl, P$_2$–P$_3$=Leu-Leu-Ethyl)

$h_A$: $R_f$=0.2 (30% EtOAc/DCM). LRMS calculated for C$_{27}$H$_{45}$N$_3$O$_4$S (M+H) 508.7 found 508.3. $h_B$: $R_f$=0.1 (30% EtOAc/DCM). LRMS calculated for C$_{27}$H$_{45}$N$_3$O$_4$S (M+H) 508.7 found 508.3. Products were confirmed by $^1$H NMR (400 MHz CDCl$_3$).

M. 2-(3-Phenylpropyl)-3-Oxo-4-Tritylthio-Butanoyl-(L)-Leu-(L)-Leu-Ethylamide (g, R=3-phenylpropyl, P$_2$–P$_3$=Leu-Leu-Ethyl)

$R_f$=0.6 (40% EtOAc/DCM). Product was confirmed by $^1$H NMR (400 MHz CDCl$_3$).

N. 2-(3-Phenylpropyl)-3-Oxo-4-Mercapto-Butanoyl-(L)-Leu-(L)-Leu-Ethylamide (i, R=3-phenylpropyl, P$_2$–P$_3$=Leu-Leu-Ethyl)

$R_f$=0.3 (40% EtOAc/DCM). LRMS calculated for C$_{27}$H$_{43}$N$_3$O$_4$S (M+H) 506.7 found 506.2. Product was confirmed by $^1$H NMR (400 MHz CDCl$_3$).

O. 2-(3-Phenylpropyl)-3-Hydroxy-4-Tritylthio-Butanoyl-(L)-β-Cyclohexylalanine-Phenethylamide (f, R=3-phenylpropyl, P$_2$–P$_3$=Cyclohexylala-Phenethyl $f_A$: $R_f$=0.8 (25% EtOAc/DCM/trace HOAc). Product was confirmed by $^1$H NMR (400 MHz CDCl$_3$). Two diastereomers (1 and 2) were separated in reaction of pair B. $f_{B1}$: $R_f$=0.7 (20% EtOAc/DCM/trace HOAc). $f_B$: $R_f$=0.5 (20% EtOAc/DCM/trace HOAc). Products were confirmed by $^1$H NMR (400 MHz CDCl$_3$).

P. 2-(3-Phenylpropyl)-3-Hydroxy-4-Mercapto-Butanoyl-(L)-β-Cyclohexylalanine-Phenethylamide (h, R=3-phenylpropyl, P$_2$–P$_3$=Cyclohexylala-Phenethyl $h_A$: $R_f$=0.4 (10% EtOAc/DCM). LRMS calculated for C$_{30}$H$_{42}$N$_2$O$_3$S (M+H) 511.7, found 511.2. $h_{B2}$: $R_f$=0.3 (20% EtOAc/DCM). LRMS calculated for C$_{30}$H$_{42}$N$_2$O$_3$S (M+H) 511.7 found 511.3. $h_{B1}$: $R_f$=0.2 (20% EtOAc/DCM). LRMS calculated for C$_{30}$H$_{42}$N$_2$O$_3$S (M+H) 511.7 found, 511.3. Products were confirmed by $^1$H NMR (400 MHz CDCl$_3$).

Q. 2-(3-Phenylpropyl)-3-Oxo-4-Butanoyl-(L)-β-Cyclohexylalanine-Phenethylamide (g, R=3-phenylpropyl, P$_2$–P$_3$=Cyclohexylala-Phenethyl)

From $f_A$: $R_f$=0.6 (10% EtOAc/DCM). Products were confirmed by $^1$H NMR (400 MHz CDCl$_3$).

R. 2-(3-Phenylpropyl)-3-Oxo-4-Mercapto-Butanoyl-(L)-β-Cyclohexylalanine-Phenethylamide (i, R=3-phenylpropyl, P$_2$–P$_3$=Cyclohexylala-Phenethyl)

$R_f$=0.2 (10% EtOAc/DCM). LRMS calculated for C$_{30}$H$_{40}$N$_2$O$_3$S (M+H) 509.7, found 509.2. Products were confirmed by $^1$H NMR (400 MHz CDCl$_3$).

S. Methyl-2-Isobutyl Acetoacetate (a, R=isobutyl)

$R_f$=0.6 (20% ether/petroleum ether). Products were confirmed by $^1$H NMR (400 MHz CDCl$_3$).

T. Methyl-2-Isobutyl-4-Bromo Acetoacetate (b, R=isobutyl)

$R_f$=0.5 (20% ether/petroleum ether). Products were confirmed by $^1$H NMR (400 MHz CDCl$_3$).

U. Methyl-2-Isobutyl-4-Tritylthio Acetoacetate (c, R=isobutyl)

$R_f$=0.4 (10% ether/petroleum ether). Products were confirmed by $^1$H NMR (400 MHz CDCl$_3$).

V. Methyl-2-Isobutyl-3-Hydroxy-4-Butyrate (d, R=isobutyl)

$d_A$: $R_f$=0.2 (20% ether/petroleum ether). $d_B$: $R_f$=0.1 (20% ether/petroleum ether). Products were confirmed by $^1$H NMR (400 MHz CDCl$_3$).

W. Methyl-2-Isobutyl-3-Hydroxy-4-Tritylthio Butyric Acid, DIEA salt (e, R=isobutyl)

$e_A$: $R_f$=0.7 (10% MeOH/DCM/trace HOAc). $e_B$: $R_f$=0.7 (10% MeOH/DCM/trace HOAc). Products were confirmed by $^1$H NMR (400 MHz CDCl$_3$).

X. 2-Isobutyl-3-Hydroxy-4-Tritylthio-Butanoyl-(L)-β-Cyclohexylalanine-Phenethylamide (f, R=isobutyl, P$_2$–P$_3$=Cyclohexylala-Phenethyl)

Two diastereomers (1 and 2) were separated in reaction of pair A. $f_{A1}$: $R_f$=0.7 (20% EtOAc/DCM/trace HOAC). $f_{A2}$: $R_f$=0.5 (20% EtOAc/DCM/trace HOAc). $f_B$: $R_f$=0.7 (20% EtOAc/DCM/trace HOAc). Products were confirmed by $^1$H NMR (400 MHz CDCl$_3$).

Y. 2-Isobutyl-3-Hydroxy-4-Mercapto-Butanoyl-(L)-β-Cyclohexylalanine-Phenethylamide (h, R=3-isobutyl, P$_2$–P$_3$=Cyclohexylala-Phenethyl)

$h_{A1}$: $R_f$=0.2 (10% EtOAc/DCM). Product was confirmed by $^1$H NMR (400 MHz CDCl$_3$). LRMS calculated for C$_{25}$H$_{40}$N$_2$O$_3$S (M+H) 449.7, found 449.2. $h_{A2}$ $R_f$=0.2 (20% EtOAc/DCM). Product was confirmed by $^1$H NMR (400 MHz CDCl$_3$). LRMS calculated for C$_{25}$H$_{40}$N$_2$O$_3$S (M+H) 449.7, found 449.1. $h_B$ $R_f$=0.1 (10% EtOAc/DCM). Product was confirmed by $^1$H NMR (400 MHz CDCl$_3$). LRMS calculated for C$_{25}$H$_{40}$N$_2$O$_3$S (M+H) 449.7, found 449.1.

Example 5

Synthesis of 2-Isobutyl-3-Oxo-4-Mercapto-Butanoyl-(L)-Leu-(L)-Leu Ethylamide through PNP-Ester.

Figure 4:
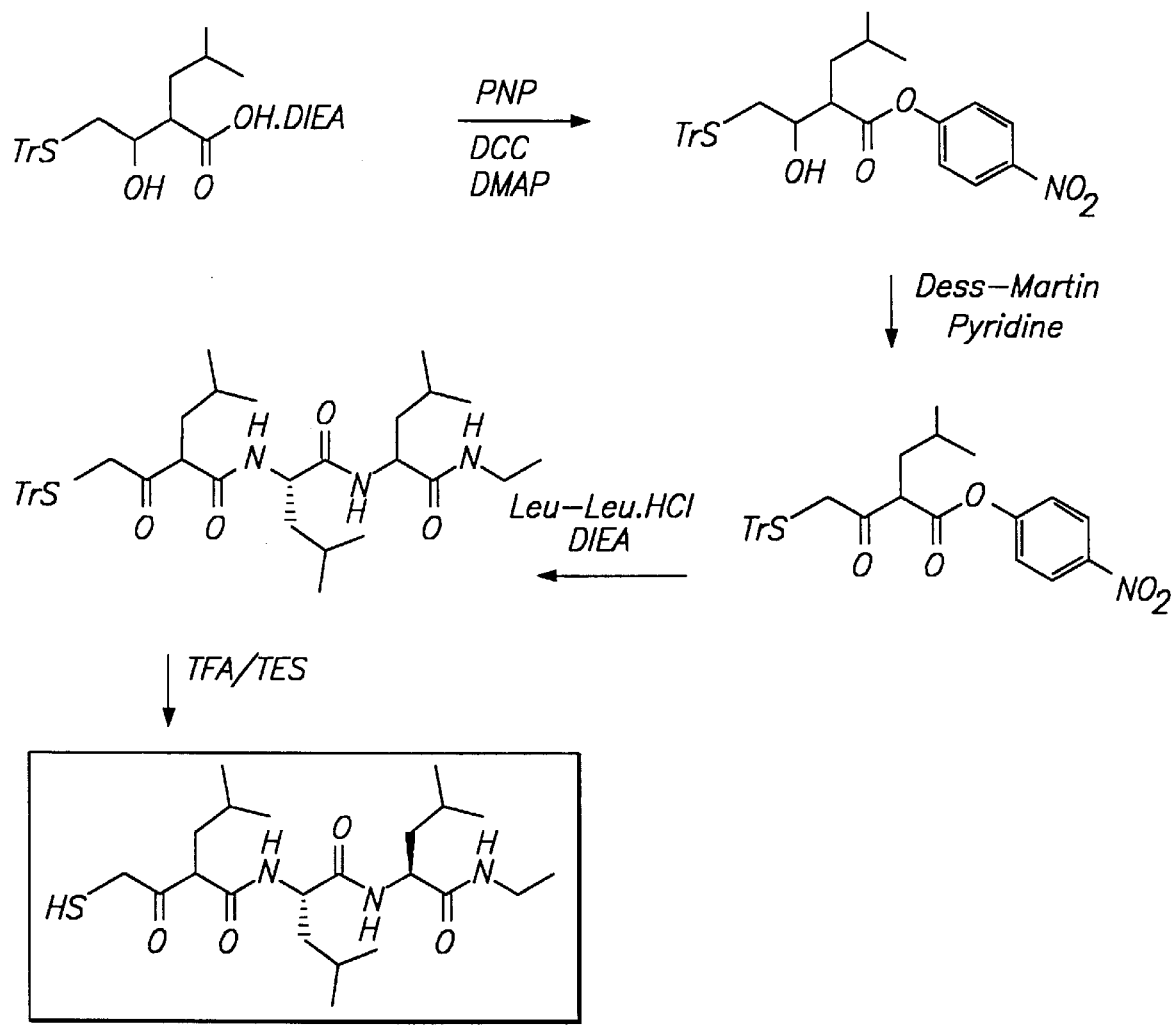

The synthesis of the title compound is illustrated in the attached FIG. 4.

A. p-Nitrophenyl-2-Isobutyl-3-Hydroxy-4-Tritylthio Butyrate

Carboxylic acid DIEA salt (100 mg, 0.177 mmol) was dissolved in 5 mL DCM at room temperature. DMAP (11 mg, 0.09 mmol, 0.5 equiv.), PNP (50 mg, 0.36 mmol, 2 equiv.), and DCC (48 mg, 0.23 mmol, 1.3 equiv.) were added sequentially. The resulting yellow solution was stirred at room temperature for 15 hours, diluted with ether (100 mL), quickly washed with saturated sodium bicarbonate (50 mL×2), pH 4 phosphate buffer (0.5M, 50 mL×1) and brine (50 mL×1), dried over $MgSO_4$, concentrated under vacuum, and column chromatographed on silica gel with 10–30% ether/petroleum ether yield 95 mg of the desired PNP-ester as a white foam (96%). $R_f$=0.25 (20% ether/petroleum ether). Product was confirmed by $^1H$ NMR (400 MHz, $CDCl_3$).

B. Nitrophenyl-p-2-Isobutyl-3-Oxo-4-Tritylthio Butyrate

The above alcohol (95 mg, 0.171 mmol) was dissolved in 5 mL DCM at room temperature. Pyridine (55 µL, 0.68 mmol, 4 equiv.) and Dess-Martin reagent (145 mg, 0.342 mmol, 2 equiv.) were added sequentially. The reaction was stirred for 30 minutes, diluted with ether (100 mL), added with 25% $Na_2S_2O_3$ in saturated sodium bicarbonate (10 mL), and vigorously stirred for 10 minutes. The organic layer was separated, quickly washed with saturated sodium bicarbonate (50 mL×2) and brine (50 mL×1), dried over $MgSO_4$, concentrated under vacuum, and column chromatographed on silica gel with 10% ether/petroleum to give 60 mg (64%) of the desired ketone as a white solid. $R_f$=0.70 (30% ether/petroleum). Products were confirmed by $^1H$ NMR (400 MHz, $CDCl_3$).

C. 2-Isobutyl-3-Oxo-4-Tritylthio-Butanoyl-(L)-Leu-(L)-Leu-Ethylamide

The above PNP-ester (55 mg, 0.099 mmol) was dissolved in 5 mL anhydrous DMF. DIEA (35 µL, 0.20 mmol, 2 equiv.) and HCl-Leu-Leu-ethylamide (31 mg, 0.10 mmol, 1 equiv.) were added at room temperature. The solution was stirred at room temperature for 20 hours, diluted with EtOAc (100 mL), washed with 10% LiCl (50 mL×3), pH 4 phosphate buffer (0.5M, 50 mL×3), saturated sodium bicarbonate (50 mL×3), and brine (50 mL×1), dried over $MgSO_4$, concentrated under vacuum to yield light-yellow solid (63 mg, 93%, crude). This crude peptide was further purified with preparative TLC (20% EtOAc/DCM) to afford 12 mg white solid. $R_f$=0.50 (40% EtOAc/DCM). Product was confirmed by $^1H$ NMR (400 MHz, $CDCl_3$).

D. 2-Isobutyl-3-Oxo-4-Mercapto-Butanoyl-(L)-Leu-(L)-Leu-Ethylamide

The above tritylthio-peptide (10 mg, 0.0146 mmol) was dissolved in 1 mL DCM. TES (12 µL, 0.075 mmol, 5 equiv.) and TFA (0.3 mL) were added sequentially at room temperature. The colorless solution was stirred at room temperature for 30 minutes, concentrated under vacuum, and column chromatographed on silica gel with 40% EtOAc/DCM to yield 5 mg of the desired mercapto peptide as a white solid (78%). $R_f$=0.30 (40% EtOAc/DCM). Products were confirmed by $^1H$ NMR (400 MHz, $CDCl_3$). LRMS calculated for $C_{22}H_{41}N_3O_4S$ (M+H) 444.6, found 444.3.

Example 6

More Efficient Synthesis of γ-Mercapto-β-Hydroxy Building Blocks.

Figure 5:
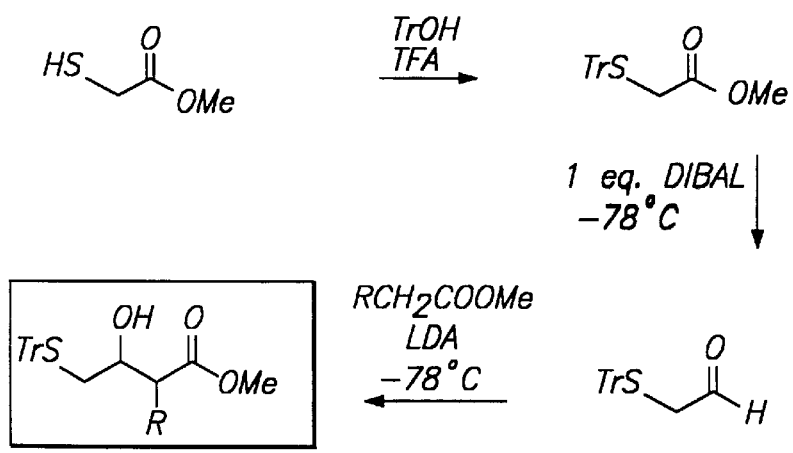

The synthesis of the title compound is illustrated in the attached FIG. 5.

A. Methyl Tritylthioglycolate

Methyl thioglycolate (0.50 g, 4.71 mmol) was dissolved in 5 mL anhydrous TFA. Triphenylmethanol (1.23 g, 4.71 mmol, 1 equiv.) was added and the deep-red solution was stirred at room temperature for 2 hours. TFA was evaporated and the residue was dissolved in ether (100 mL), washed with saturated sodium bicarbonate (50 mL×2) and brine (50 mL×1), dried over $MgSO_4$, and concentrated to dryness, yielding a white solid (1.64 g, quantitative). $R_f$=0.45 (20% ether/petroleum ether). Products were confirmed by $^1H$ NMR (400 MHz, $CDCl_3$).

B. Tritylthioglycoaldehyde

Methyl tritylthioglycolate (2.00 g, 5.74 mmol) was dissolved in 20 mL anhydrous toluene and cooled to −78° C. DIBAL (4.02 mL, 1.5M in toluene, 6.03 mmol, 1.05 equiv.) was added slowly within 2 hours while the bath temperature was maintained at −78° C. The reaction was stirred another 2 hours and quenched with saturated ammonium chloride (20 mL) at this temperature, diluted with ether (200 mL), warmed to room temperature with vigorous stirring. The organic layer was separated, washed with saturated ammonium chloride (100 mL×3) and brine (100 mL×1), dried over $MgSO_4$, concentrated under vacuum to yield a light-yellow oil (2.06 g, quantitative), which was used in the next step without further purification. $R_f$=0.40 (20% ether/petroleum ether).

C. Methyl-2-n-Heptyl-3-Hydroxy-4-Tritylthio Butyrate

Methyl nonanoate (0.59 g, 3.44 mmol, 1.2 equiv.) was dissolved in 7 mL THF and cooled to −78° C. Freshly prepared LDA (6.88 mL, 0.5M in THF, 3.44 mmol, 1.2 equiv.) was added dropwise to the solution. After stirring for 2 hours at −78° C., tritylthioglycoaldehyde (10.3 g, 2.87 mmol, crude, in 5 mL THF) was added dropwise to the resulting enolate solution. The reaction was stirred for 4 hours at −78° C. and 16 hours at from −78° C. to room temperature, diluted with ether (200 mL), washed with water (200 mL×2) and brine (100 mL×1), dried over $MgSO_4$, concentrated under vacuum, and column chromatographed on silica gel with 10–20% ether/petroleum ether, yielding two isomers with a combined yield of 66%. A: 0.55 g, $R_f$=0.30 (20% ether/petroleum ether); B: 0.38 g, $R_f$=0.20 (20% ether/petroleum ether). Products were confirmed by $^1H$ NMR (400 MHz, $CDCl_3$). They are identical with the material prepared in Example 4 ($d_A$ and $d_B$, R=n-heptyl).

Similar building blocks with other side-chains in Example 4 can also be synthesized more efficiently by this procedure.

Example 7

Non-Oxidative Synthesis of Mercapto-ketone Inhibitors:

Use of MOM Enol Ethers as Masked Ketones Suitable for Solid-Support Synthesis Malonyl mercaptoketones have proven to be highly potent inhibitors for collagenase-1 and stromelysin-I. Since the use of unprotected mercapto ketone building blocks lacked the desired efficiency to be applicable in solid supports library synthesis, a masked mercaptoketone is highly desirable.

Figure 6:
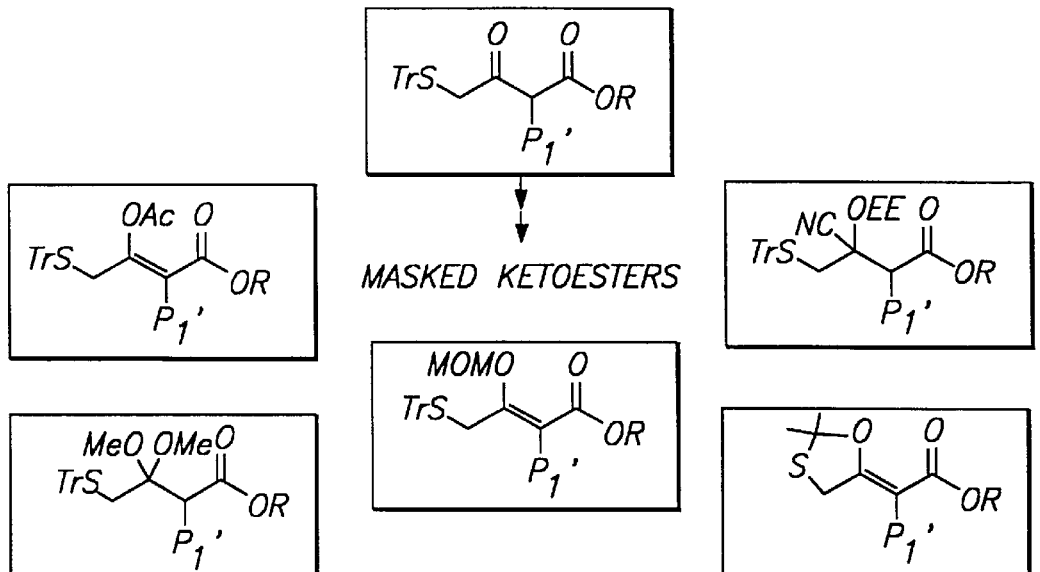
Figure 7:
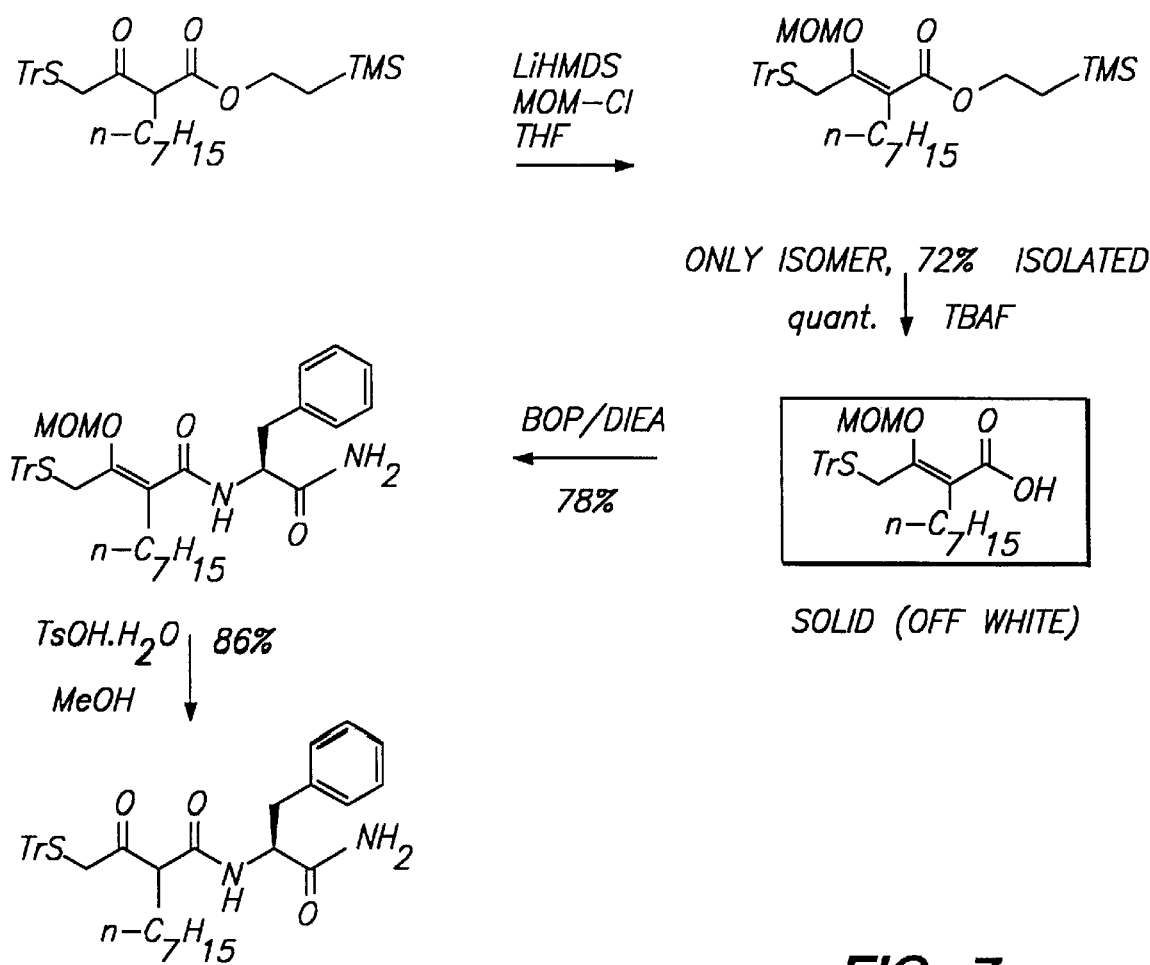

Several forms of masked ketones are possible candidates for this purpose, as shown in FIG. 6. Upon trying these, the MOM enol ether proved to be the best form of masked ketones for use in solid phase synthesis of mercaptoketones (FIG. 7).

The desired building block, namely, β-MOM enol ether carboxylic acid, can be conveniently prepared by two steps from the readily available β-keto TMS-ethyl ester. Coupling of this stable carboxylic acid with an amine using BOP/DIEA gave the right product in 78% isolated yield. Most importantly, the unmasking of the ketone functionality was readily effected with dilute tosylic acid in wet methanol at room temperature.

Example 8

Figure 8:
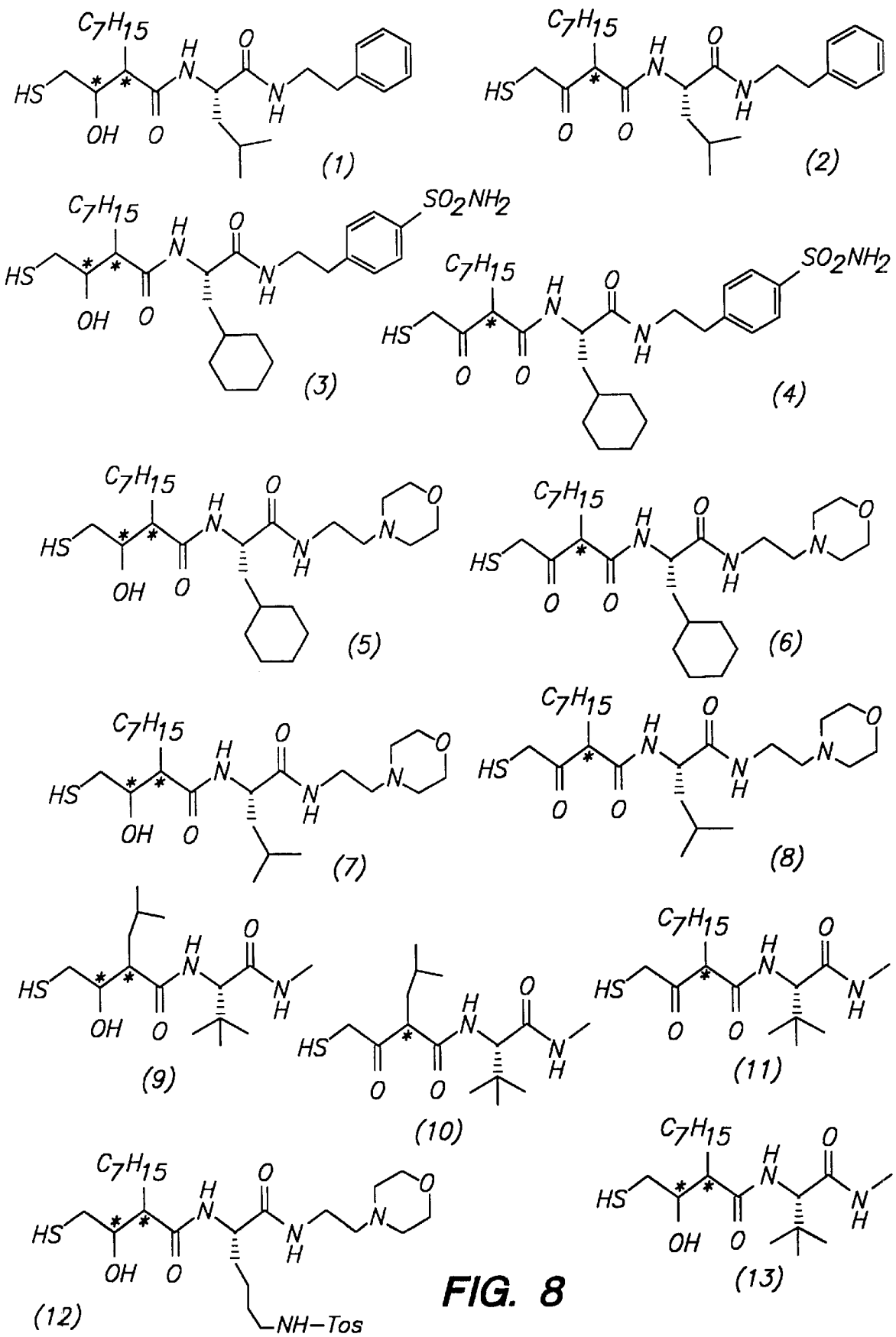

Synthesis of More Mercapto-ketone and Mercapto-alcohol Inhibitors with other $P_2'P_3'$'s Additional malonyl mercapto-ketone and mercapto-alcohol inhibitors of collagenase-1 and stromelysin-I have been synthesized using a heptyl building block (Pair B) and various reported good $P_2'$–$P_4'$'s. Several of the inhibitors are shown in FIG. 8.

Example 9

Diphenyl Acetonides as Protected Forms of 1,2-Mercapto-Alcohols

Figure 9:
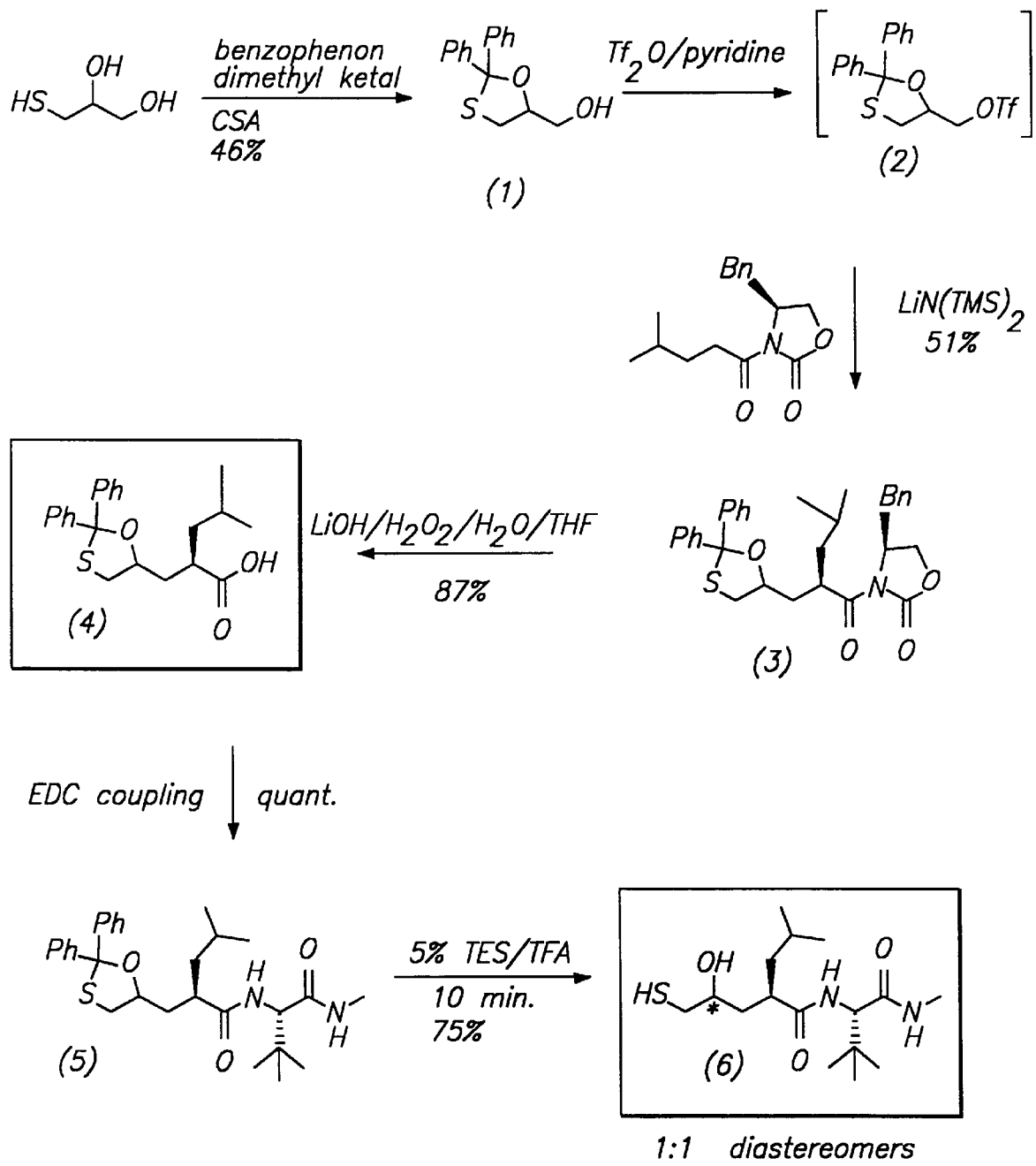

As disclosed herein, succinyl mercapto-alcohols are also very good inhibitors of collagenase-1 and stromelysin-I. However, the building blocks used in the solution synthesis (i.e., tritylmercaptoketone succinic acids) are not efficient for solid phase synthesis. A simultaneous protection of both the hydroxy and mercapto groups would be very desirable. A number of acetonides/ketals were examined for this purpose. Among them, are dimethyl acetonide, benzylidene, and diphenyl acetonide. Diphenyl acetonid worked the best. This protecting group was then used in carrying out the reaction scheme shown in FIG. 9 as described below.

A. 2,2-Diphenyl-5-hydroxyinethyl-1,3-oxathiolane (1)

3-Mercapto-1,2-propanediol(3.26 g, 30.00 mmol) was dissolved in benzene (60 mL). Benzophenone dimethyl ketal (13.48 g, 60.0 mmol, 2 equiv.) and CSA (0.70 mg, 3.00 mmol, 0.1 equiv.) were added. The solution was heated with an oil bath to reflux. Benzene/methanol was collected and removed while more benzene was added to the refluxing reaction. After about 200 mL benzene/methanol was distilled out, the reaction was cooled to room temperature, applied directly onto a silica gel column. The column was then eluted was 20%–40% ether/petroleum ether to afford a thick oil as the desired product (3.78 g, 46). $R_f$=0.25, 20% ether/petroleum ether. $^1$H NMR (400 MHz, $C_6D_6$) δ=2.56 (dd, J=6.3, 10.2 Hz, 1 H), 2.83 (dd, J=7.7, 10.2 Hz, 1 H), 3.35 (br dd, J=5.3, 11.6 Hz, 1 H), 3.44 (br dd, J=3.5, 11.6 Hz, 1 H), 3.88–3.95 (m, 1 H), 6.94–7.20 (m, 6 H), 7.54 (d, J=7.5 Hz, 2 H), 7.70 (d, J=7.5 Hz, 2 H). $^{13}$C NMR (100 MHz, $C_6D_6$) δ=35.90, 63.97, 83.29, 100.20, 126–129 (m).

B. (3(2R) ,4S)-3-(2-isobutyl-3-(2,2-diphenyl-1,3-oxathiolane-5-yl)-1-oxopropyl)-4-benzyl-2-oxazolidinone (3)

The above alcohol (0.817 g, 3.00 mmol, 3 equiv.) was dissolved in benzene (6 mL). Pyridine (0.74 mL, 9.00 mmol, 9 equiv.) and Tf$_2$O (0.76 mL, 4.50 mmol, 4.5 equiv.) were added sequentially at room temperature. After stirring for 10 minutes, 5% sodium bicarbonate (60 mL) was added. The reaction was vigorously stirred for another 10 minutes, quickly filtered through a short silica gel pad. The filtrate was concentrated at room temperature until most of the benzene was gone (do not dry the triflate completely because of the risk of decomposition) and immediately redissolved in dry THF. This triflate/THF solution was then added dropwise to a THF solution (–78° C.) of the lithium enolate of (4S)-3-(4-methyl-1-oxopentyl)-4-benzyl-2-oxazolidinone (2, 0.276 g, 1.00 mmol, 1 equiv., prepared according to procedures of Evans et al., *supra*.) pre-formed by treatment with 1.5 equivalent of LiN(TMS)$_2$/THF (1.5 mL, 1.0M/THF) in THF (5 mL) at –78° C. The reaction was stirred while slowly warmed up to 0° C. in 2 hours, and kept at 0° C. for another 3 hours, and quenched with acetic acid (0.2 mL), diluted with ether (150 mL), washed with water (50 mL×3) and brine (50 mL×1), dried over magnesium sulfate, concentrated, and subjected to flash chromatography with 10%–20% ether/petroleum ether to yield 0.271 g (51%) desired product as a white solid. $R_f$=0.3, 20% ether/petroleum ether. $^1$H NMR (400 MHz, $C_6D_6$) δ=0.80–1.15 (m, 6 H), 1.25–2.02 (m, 5 H), 2.30–2.53 (m, 1 H), 2.70–2.80 (m, 2 H), 2.95–3.13 (m 2 H), 3.34–3.42 (m, 1 H), 4.05–4.23 (m, 2 H), 4.40–4.65 (m, 1 H), 6.70–7.20 (m, 11 H), 7.50–7.89 (m, 4 H). LRMS calcd. for $C_{32}H_{35}NNaO_4S$ (M+Na) 552.7, found 552.3.

C. (2R)-2-Isobutyl-3-(2,2-diphenyl-1,3-oxathiolane-5-yl)-propionic acid (4)

The above oxazolidinone (0.250 g, 0.47 mmol) was dissolved in THF/water (8 mL, 3:1) and cooled to 0° C. Hydrogen peroxide (0.21 mL, 31% in water, 1.88 mmol, 4 equiv.) and solid LiOH (23 mg, 0.95 mmol, 2 equiv.) were added sequentially. The reaction was stirred at 0° C. for 30 minutes, sodium sulfite (300 mg, in 2 mL water) was then added and the system vigorously stirred for another 10 minutes, acidified carefully with 0.5% HCl to pH=3, extracted with EtOAC (20 mL×4). The extracts were combined, dried over magnesium sulfate, concentrated, and subjected to flash chromatography using 20%–40% ether/petroleum ether to yield the acid as a white solid (131 mg, 87%). $R_f$=0.4, 40% ether/petroleum. $^1$H NMR (400 MHz, $C_6D_6$) δ=0.70–0.90 (m, 6 H), 1.00–2.18 (m, 5 H), 2.55–2.98 (m, 3 H), 3.82–4.15 (m, 1 H), 6.90–7.20 (m, 6 H), 7.60 (br d, J=7.3 Hz, 2 H), 7.80 (br d, J=7.3 Hz, 2 H). LRMS calcd. for $C_{22}H_{27}O_3S$ (M+H) 371.5, found 371.0

D. (2R )-2-Isobutyl-3-(2,2-diphenyl-1,3-oxathiolane-5-yl)-propionyl-Butylglycine-NHMe (5)

The above carboxylic acid (42 mg, 0.11 mmol) was dissolved in DCM (5 mL). DIEA (48 mL, 0.28 mmol, 2.5 equiv.), t-butylglycine-NHMe-HCl (31 mg. 0.17 mmol, 1.5 equiv.), HOBt 18 mg, 0.13 mmol, 1.2 equiv.), and EDC (25 mg, 0.13 mmol, 1.2 equiv.) were added sequentially. The reaction was then stirred at room temperature for 4 hours, diluted with EtOAc (50 mL), washed with phosphate buffer (0.5M, pH=4, 20 mL×3), saturated sodium bicarbonate (20 mL×3), and brine (20 mL×1), dried over sodium sulfate, and concentrated to yield 55 mg (quantitative) white solid as the crude product. $R_f$=0.5, 40% EtOAc/DCM. $^1$H NMR (400 MHz, CDCl$_3$) δ=0.80–1.00 (m, 15 H), 1.25–1.95 (m, 5 H), 2.00–2.25 (m, 1 H), 2.50–2.65 (m, 1 H), 2.75-2.83 (m, 3 H), 2.90–3.04 (m, 1 H), 3.15–3.22 (m, 1 H), 4.08–4.17 (m, 1 H), 4.18–4.25 (m, 1 H), 5.85–6.05 (m, 1 H), 6.25–6.32 (m, 1 H), 7.20–7.65 (m, 10 H).

E. 2-Isobutyl-4-hydroxy-5-mercapto-pentanoyl-t-butylglycine-NHMe (6)

The above diphenyl acetonide (50 mg, 0.10 mmol) was treated with 5% TES/TFA (5 mL) at room temperature for 20 minutes. A bright yellow color appeared immediately upon contact and disappeared quickly in a few minutes. The reaction was concentrated under vacuum. The resulting residue was subjected to flash chromatography using 20%–40% EtOAc/DCM to yield 25 mg of white solid as the desired product (75%). $R_f$=0.2, 40% EtOAc/DCM. $^1$H NMR (400 MHz, CDCl$_3$) δ=0.84–0.91 (m, 6 H), 1.00 (s, 9 H/2), 1.01 (S, 9 H/2), 1.25–1.85 (m, 5 H), 2.43–2.55 (m, 2 H), 2.65–2.74 (m, 1 H), 2.80 (s, 3 H/2), 2.82 (2, 3 H/2), 3.55–3.69 (m, 1 H), 4.19 (d, J=2.8 Hz, 1 H/2) 4.22 (d, J=2.8 Hz, 1 H/2), 5.82–5.90 (m, 1 H), 6.40–6.52 (m, 1 H). LRMS cald. for $C_{16}H_{33}O_3N_2S$ (M+H) 333.5, found 333.0

Example 10

Figure 10:
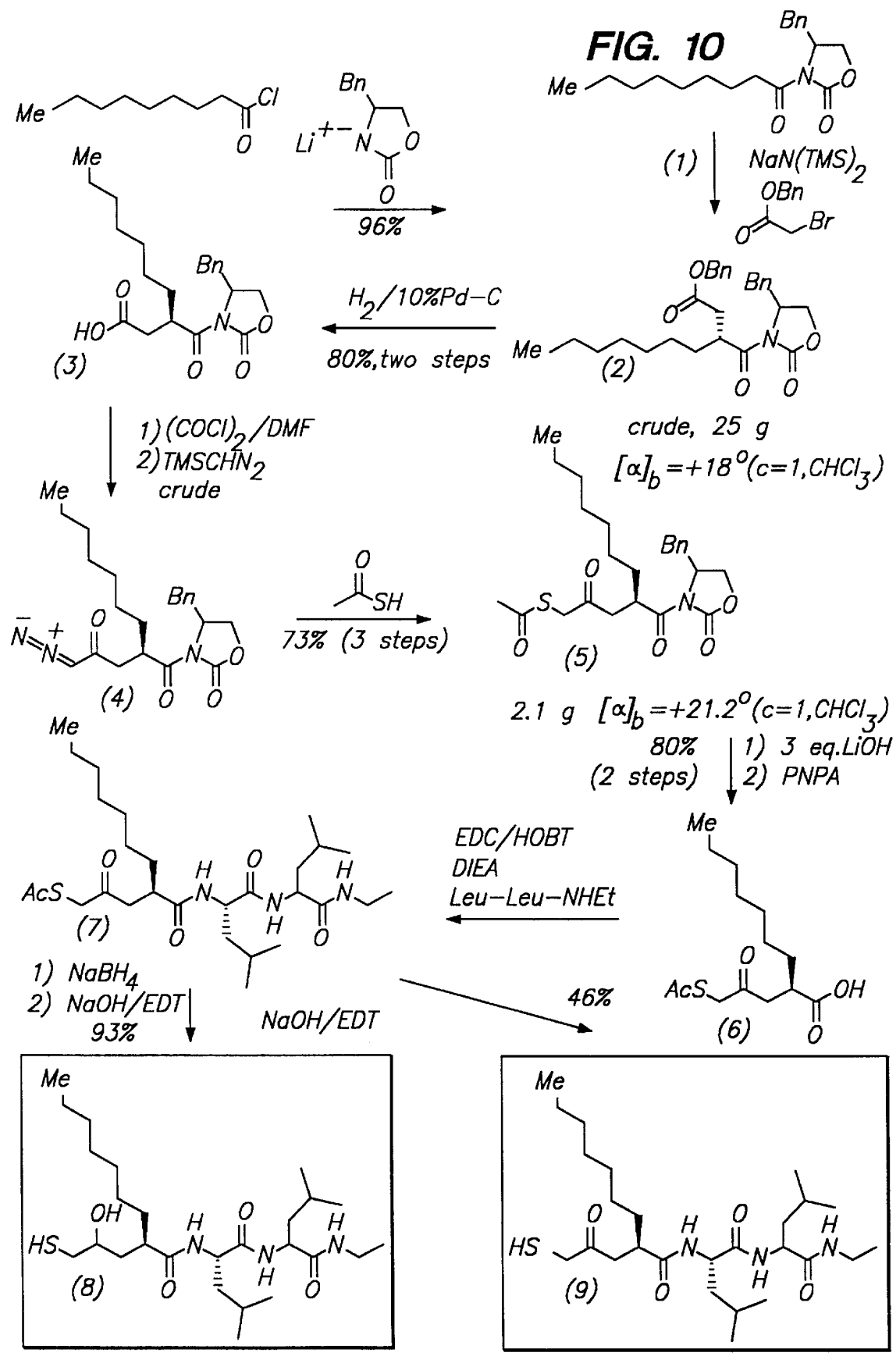

Synthesis of Succinyl Mercaptoketone and Mercaptoalcohol Inhibitors of Collagenase-1 and/or Stromelysin-I Succinyl mercaptoketones and mercaptoalcohols were synthesized according to the scheme shown in FIG. 10. Briefly, the synthesis started with nonanoyl chloride. The Evans method (Evans et al., *J. Am. Chem. Soc.* 112:4011–4030 (1990)) was used to prepare the 2-R-2-heptyl succinic acid (3) in greater than 75% overall isolated yield. This carboxylic acid was then transformed to acetyl-mercapto-ketone (5) through the acid chloride and the diazoketone in 73% yield. The oxazolidinone was then hydrolyzed with excess LiOH and the simultaneously freed thiol was reacetylated by p-nitrophenol acetate, yielding the acetylmercaptoketone building block (6) in 80% isolated yield. Regular EDC coupling of the building block with Leu-Leu-NHEt gave the protected mercapto-ketonepeptide (7). De-acetylation with NaOH/excess EDT in dioxane yielded the desired mercapto-ketone inhibitor (9), while reduction followed by deacetylation gave the alcohol (8).

Figure 11:
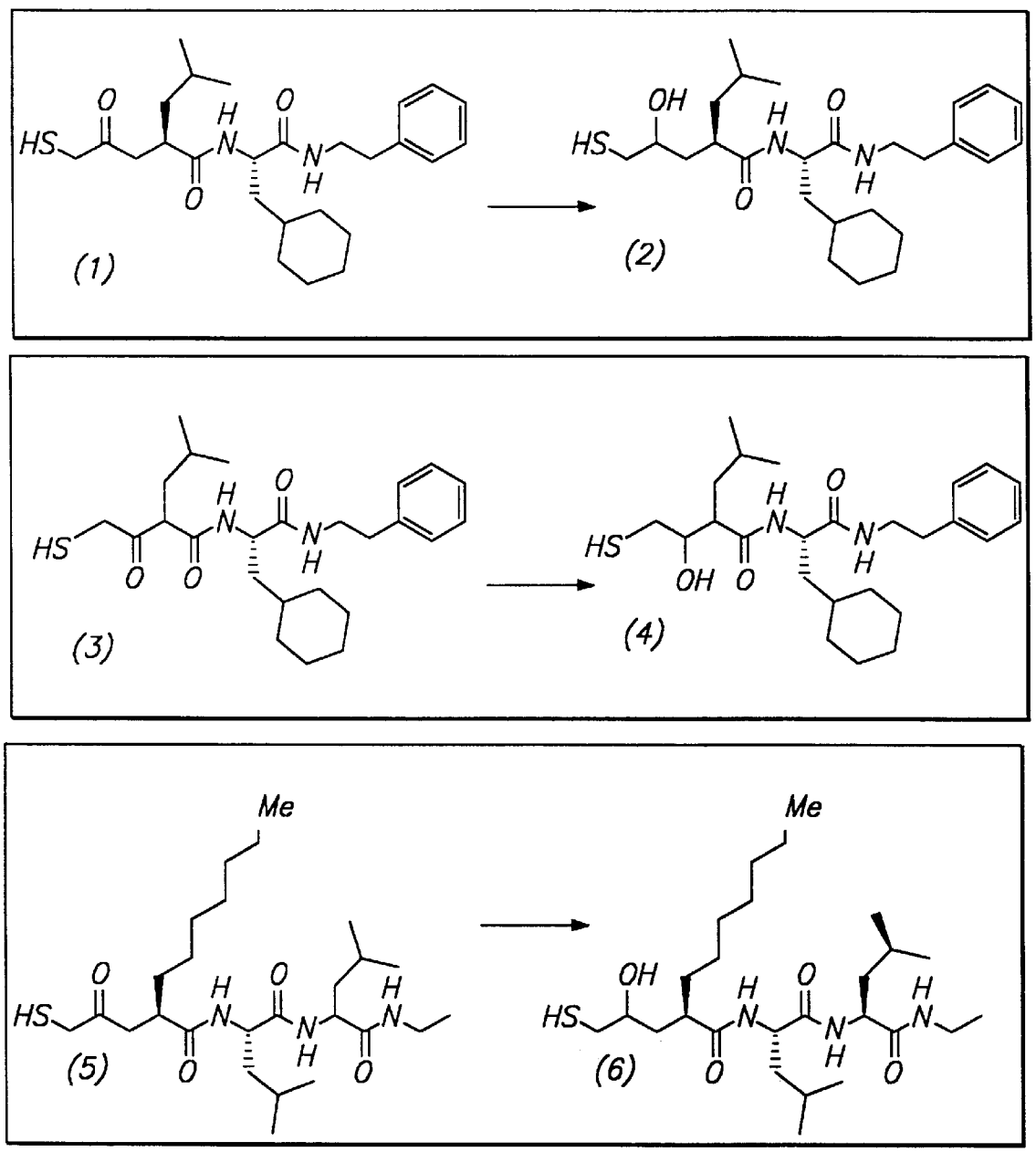

The succinyl mercaptoketone and mercaptoalcohol inhibitors were compared to the corresponding malonyl mercapto inhibitors in their ability to inhibit stromelysin. The malonyl mercaptoalcohol shown in FIG. 11 (1) is significantly less potent against stromelysin than the corresponding mercaptoketone (2). In contrast, the succinyl mercaptoalcohol (3) is more than twice as potent as the corresponding mercaptoketone (4). Because mercaptoalcohols are easier to handle than mercaptoketones, this result indicates that succinyl mercaptoalcohols may be preferred for therapeutic use.

Example 11

Synthesis of β-Mercapto-α-Heptyl-proprionyl-Leu-Leu-NHEt

Figure 12:
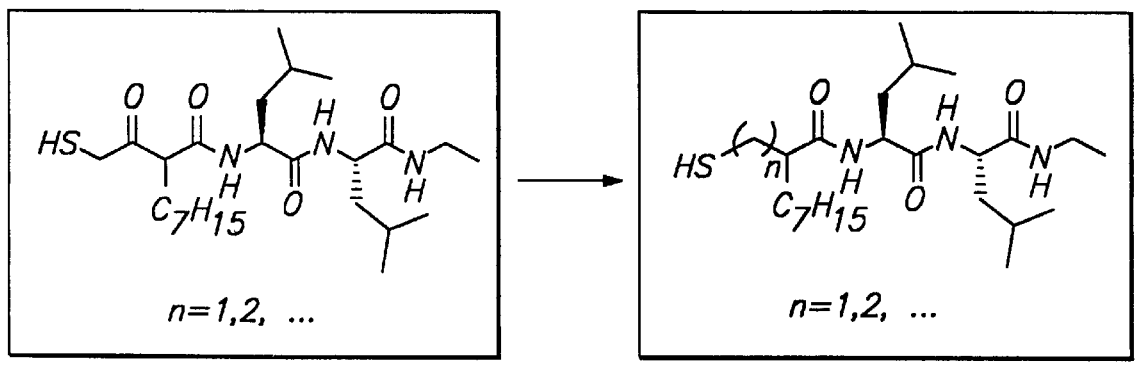
Figure 13:
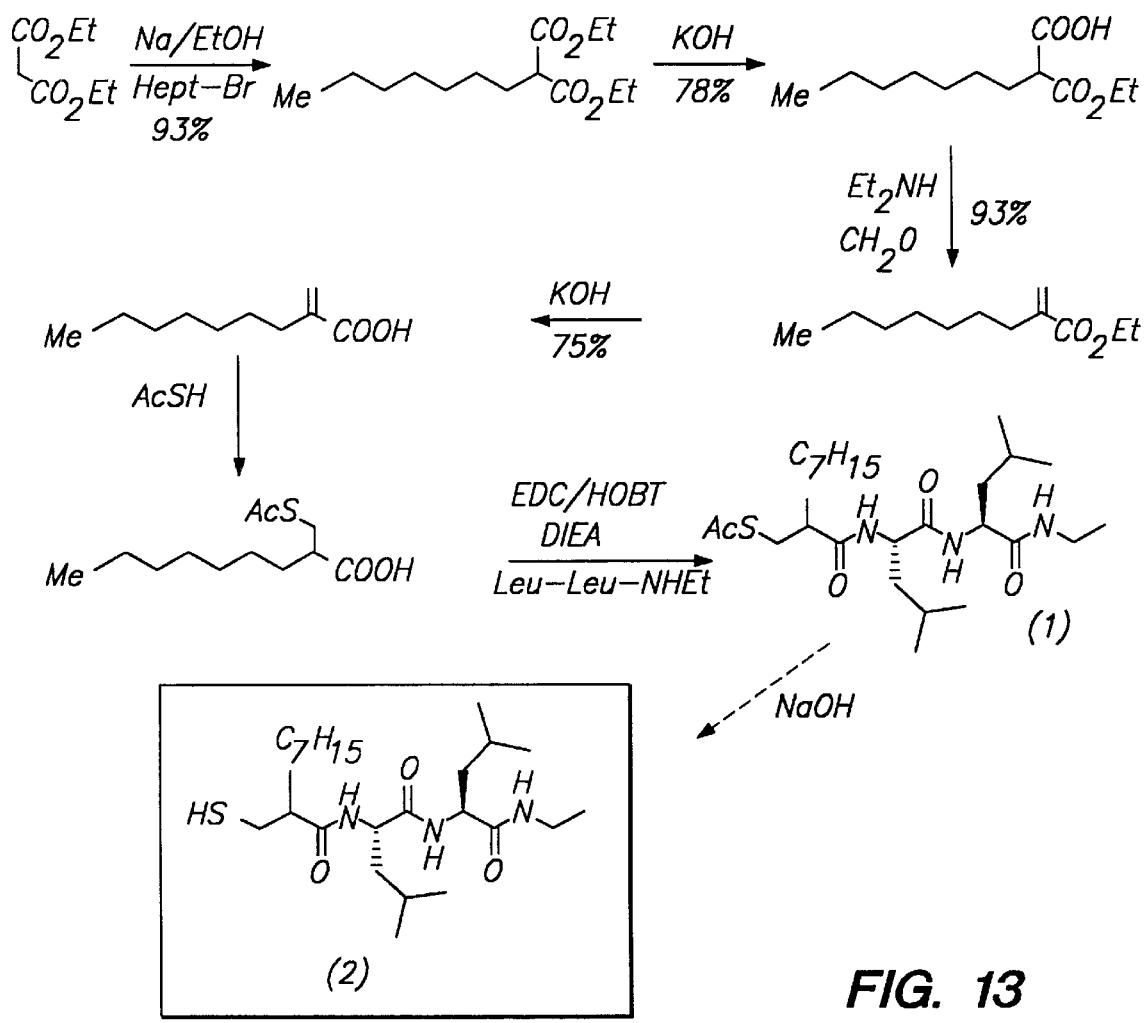

A series of deoxy mercaptanes with different chain-lengths between the thiol and P$_1$' (n=1,2,3, FIG. 12) are required to probe the source of inhibitory properties of the mercapto-ketones and alcohols. The compound with n=2 was synthesized and strongly inhibited stromelysin. The synthesis of the mercaptane with n=1 is currently being synthesized as shown in FIG. 13.

Alkylation of diethyl malonate with heptyl bromide in ethanol followed by saponification with 1 equivalent KOH in ethanol yielded the monoester. Treatment of this monoester with diethyl amine and formaldehyde gave the α, β-unsaturated ester, which was hydrolyzed with excess KOH to the carboxylic acid. Michael addition of thioacetic acid to this α, β-unsaturated carboxylic acid in toluene yielded the desired 2-acetylthiomethyl nonanoic acid. EDC coupling with Leu-Leu-NHEt gave the acetylated peptide. The compound is then deprotected to obtain the free mercaptan.

Example 12

Synthesis of Mercapto-Derivatives of Hydroxymate Inhibitors

Figure 14:
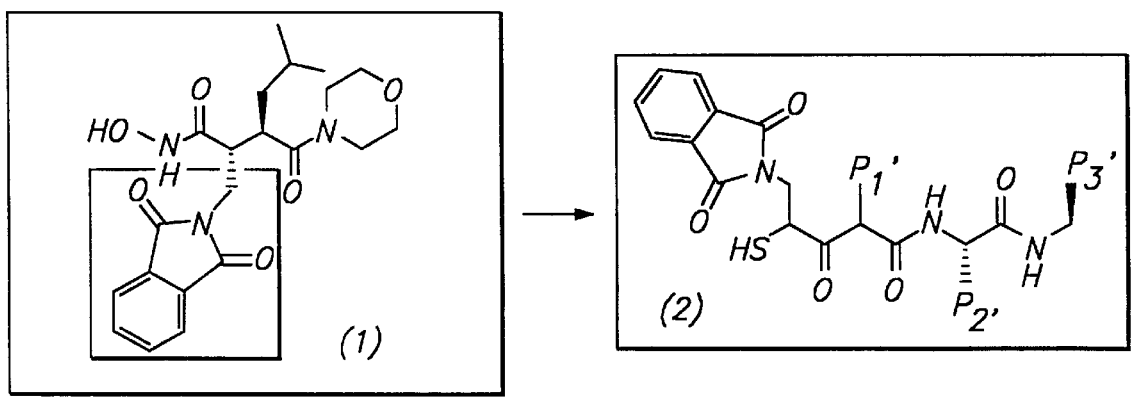

Certain hydroxymate compounds, such as that shown as compound (1) in FIG. 14, are effective inhibitors of collagenase-1 and stromelysin-I metalloproteases. However, because hydroxymates are toxic, they have not found use in the clinic. This Example teaches how one of skill in the art can synthesize less toxic mercaptoalcohol and mercaptoketone derivatives of hydroxymate metalloprotease inhibitors, for example compound (2) in FIG. 14.

Figure 15A:
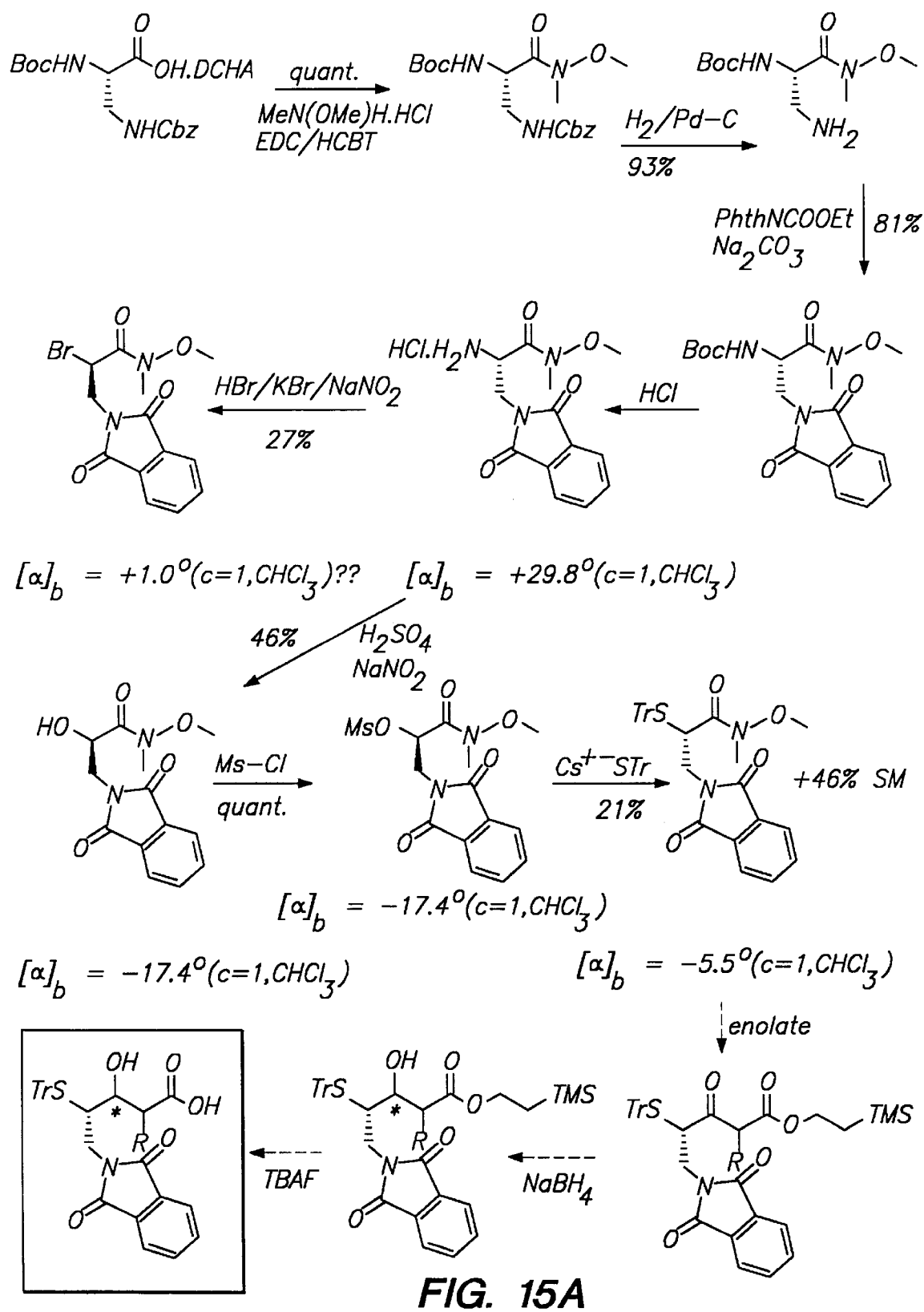
FIGS. 15A and 15B illustrate a strategy for synthesizing optically active mercapto derivatives of hydroxymate metalloprotease inhibitor compounds. The dashed arrows indicate synthesis steps not yet completed.
Figure 15B:
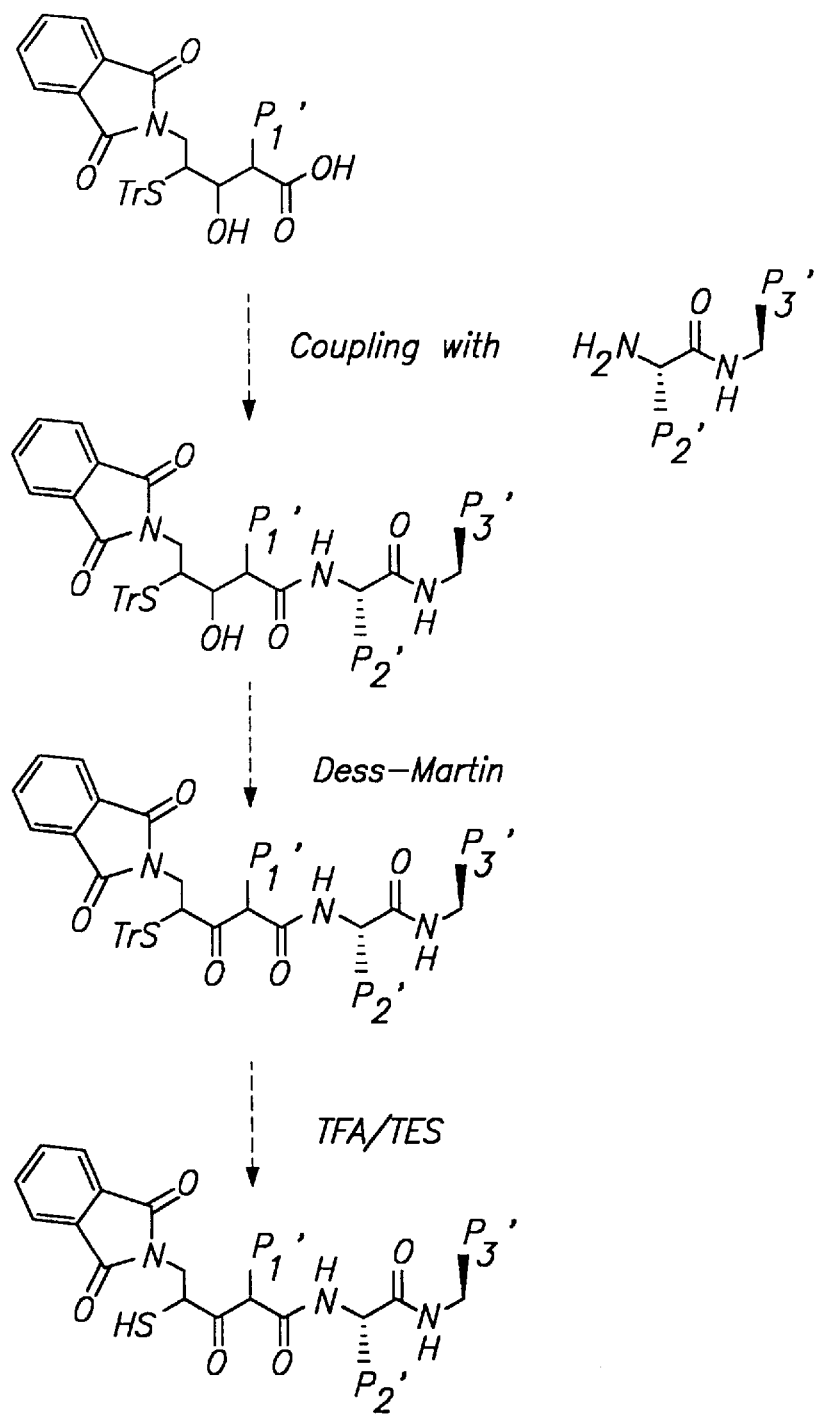
Figure 16:
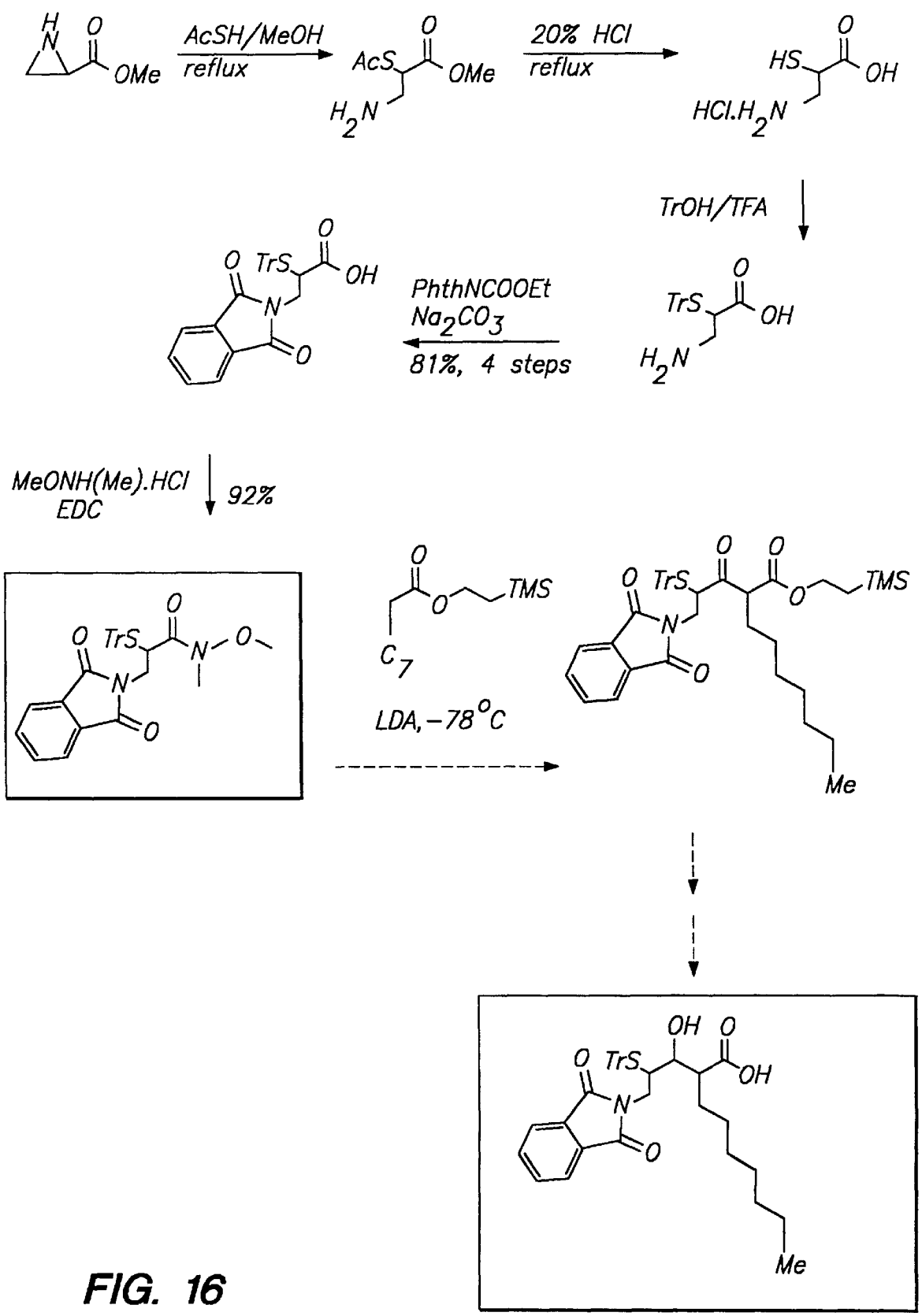

FIGS. 15A and 15B provide a strategy for synthesizing optically active mercaptoalcohol and mercaptoketone derivatives of hydroxymate compounds of the type shown in FIG. 14(1). FIG. 16 provides a strategy for synthesizing racemic building blocks for use in synthesizing mercapto derivatives of hydroxymate metalloprotease inhibitors.

Unless defined otherwise, all technical and scientific terms used herein have the same meaning as commonly understood by one of ordinary skill in the art to which this invention belongs. Although any methods and materials similar or equivalent to those described can be used in the practice of testing of the present invention, the preferred methods and materials are now described. All publications and patent documents referenced in this application are incorporated herein by reference in their entirety as though each and every publication and patent document was specifically incorporated herein by reference in its entirety.

It is understood that the examples and embodiments described herein are for illustrative purposes only and the various modifications or changes in light thereof will be suggested to persons skilled in the art and are to be included within the spirit and purview of this application and scope of the appended claims.

What is claimed is:
1. A compound comprising a formula:

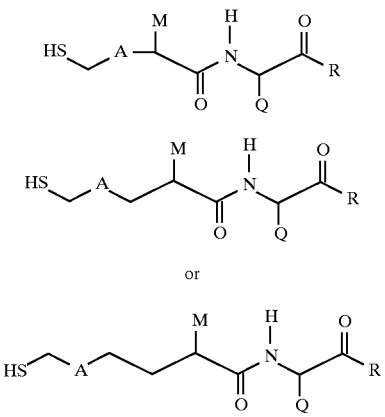

or wherein
A is selected from the group consisting of >C=O and >CHOH;
M and Q are each independently selected from the group consisting of hydrogen, alkyl, substituted alkyl, aryl, and heteroaryl;
R is selected from the group consisting of —NR$^1$R$^2$ and —NHCH(Q')C(O)NR$^1$R$^2$;

$R^1$ is selected from the group consisting of hydrogen, alkyl, substituted alkyl, aryl, heteroaryl, arylalkyl, heteroarylalkyl, heterocyclic and heterocyclicalkyl;

$R^2$ is hydrogen, or $R^1$ and $R^2$ together with the nitrogen atom to which they are attached form a heterocyclic or heteroaryl ring;

Q' is selected from the group consisting of hydrogen, alkyl, substituted alkyl, aryl, and heteroaryl;

or pharmaceutically acceptable salts thereof.

2. The compound according to claim 1, wherein M is alkyl.

3. The compound according to claim 2, wherein M is heptyl or isobutyl.

4. The compound according to claim 2, wherein Q is alkyl.

5. The compound according to claim 4, wherein Q is isobutyl or cyclohexylmethyl.

6. The compound according to claim 2, wherein R is —NHCH(Q')C(O)NR$^1$R$^2$ and Q and Q' are each independently alkyl.

7. The compound according to claim 6, wherein Q is isobutyl or cyclohexylmethyl, and Q' is isobutyl.

8. The compound according to claim 1, wherein M is substituted alkyl wherein said alkyl substitution is an aryl substitution.

9. The compound according to claim 8, wherein M is phenylpropyl.

10. The compound according to claim 8, wherein Q is alkyl.

11. The compound according to claim 10, wherein Q is isobutyl or cyclohexylmethyl.

12. The compound according to claim 10, wherein R is —NHCH(Q')C(O)NR$^1$R$^2$ and Q and Q' are each independently alkyl.

13. The compound according to claim 12, wherein Q is isobutyl or cyclohexylmethyl, and Q' is isobutyl.

14. A compound according to claim 1 wherein said compound is selected from the group consisting of 2-iso-butyl-4-oxo-5-mercapto-pentanoyl-(L)-β-cyclohexylalanine-phenethylamide;

2-iso-butyl-3-oxo-4-mercapto-butanoyl-(L)-β-cyclohexylalanine-phenethyl amide;

2-iso-butyl-3-hydroxy-4-mercapto-butanoyl-(L)-β-cyclohexylalanine-phenethylamide;

2-iso-butyl-3-oxo-4-mercapto-butanoyl-(L)-Leu-(L)-Leu-ethylamide;

2-n-heptyl-3-hydroxy-4-mercapto-butanoyl-(L)-Leu-(L)-Leu-ethylamide;

2-n-heptyl-3-oxo-4-mercapto-butanoyl-(L)-Leu-(L)-Leu-ethylamide;

2-n-heptyl-3-hydroxy-4-mercapto-butanoyl-(L)-β-cyclohexylalanine-phenethylamide;

2-n-heptyl-3-oxo-4-mercapto-butanoyl-(L)-β-cyclohexylalanine-phenethylamide;

2-(3-phenylpropyl)-3-hydroxy-4-mercapto-butanoyl-(L)-Leu-(L)-Leu-ethylamide;

2-(3-phenylpropyl)-3-oxo-4-mercapto-butanoyl-(L)-Leu-(L)-Leu-ethylamide;

2-(3- phenylpropyl)-3-hydroxy-4-mercapto-butanoyl-(L)-β-cyclohexylalanine-phenethylamide;

2-(3-phenylpropyl)-3-oxo-4-mercapto-butanoyl-(L)-β-cyclohexylalanine-phenethylamide;

2-iso-butyl-4-oxo-5-mercapto-pentanoyl-(L)-β-t-butylglycine-(2-pyridyl)amide;

2-iso-butyl-4-hydroxy-5-mercapto-pentanoyl-(L)-β-t-butylglycine-(2-pyridyl)amide;

2-iso-butyl-4-hydroxy-5-mercapto-pentanoyl-(L)-β-cyclohexylalanine-phenethylamide;

2-iso-butyl-3-hydroxy-4-mercapto-butanoyl-(L)-t-butylglycine-methylamide;

2-iso-butyl-3-oxo-4-mercapto-butanoyl-(L)-t-butylglycine-methylamide;

2-iso-butyl-4-hydroxy-5-mercapto-pentanoyl-(L)-t-butylglycine-methylamide;

2-n-heptyl-4-hydroxy-5-mercapto-pentanoyl-(L)-Leu-(L)-Leu-ethylamide;

2-n-heptyl-4-oxo-5-mercapto-pentanoyl-(L)-Leu-(L)-Leu-ethylamide;

2-n -heptyl-3-hydroxy-4-mercapto-butanoyl-(L)-t-butylglycine-methylamide;

2-n-heptyl-3-oxo-4-mercapto-butanoyl-(L)-t-butylglycine-methylamide;

2-n-heptyl-4-hydroxy-5-mercapto-pentanoyl-(L)-t-butylglycine-methylamide;

2-n-heptyl-4-oxo-5-mercapto-pentanoyl-(L)-t-butylglycine-methylamide;

2-n-heptyl-3-hydroxy-4-mercapto-butanoyl-(L)-Leu-phenethylamide;

2-n-heptyl-3-oxo-4-mercapto-butanoyl-(L)-Leu-phenethylamide;

2-n-heptyl-3-oxo-4-mercapto-butanoyl-(L)-Leu-2-N-morpholino-ethylamide;

2-n-heptyl-3-hydroxy-4-mercapto-butanoyl-(L)-Leu-2-N-morpholino-ethylamide;

2-n-heptyl-3-hydroxy-4-mercapto-butanoyl-(L)-β-cyclohexylalanine-2-(4-sulphonamide-phenyl)ethylamide; and 2-n-heptyl-3-hydroxy-4-mercapto-butanoyl-(L)-ε-N-tosyl-Lysine-(L)-Leu-ethylamide.

* * * * *